(12) United States Patent
Sabirova et al.

(10) Patent No.: US 8,623,632 B2
(45) Date of Patent: Jan. 7, 2014

(54) EXTRACELLULAR POLYHYDROXYALKANOATES PRODUCED BY GENETICALLY ENGINEERED MICROORGANISMS

(75) Inventors: Julia Sabirova, Brauschweig (DE); Peter Golyshin, Wolfenbuttel (DE); Manuel Ferrer, Madrid (ES); Heinrich Lunsdorf, Erkerode (DE); Wolf-Rainer Abraham, Hillerse (DE); Kenneth Timmis, Wolfenbuttel (DE)

(73) Assignee: Helmholtz-Zentrum fur Infektionsforschung GmbH, Braunschweig (DE)

( * ) Notice: Subject to any disclaimer, the term of this patent is extended or adjusted under 35 U.S.C. 154(b) by 653 days.

(21) Appl. No.: 11/989,909

(22) PCT Filed: Aug. 9, 2006

(86) PCT No.: PCT/EP2006/007888
§ 371 (c)(1),
(2), (4) Date: Jul. 30, 2010

(87) PCT Pub. No.: WO2007/017270
PCT Pub. Date: Feb. 15, 2007

(65) Prior Publication Data
US 2011/0183388 A1 Jul. 28, 2011

(30) Foreign Application Priority Data
Aug. 9, 2005 (EP) ..................................... 05017308

(51) Int. Cl.
*C12N 1/20* (2006.01)
(52) U.S. Cl.
USPC ................................... 435/252.34; 435/252.3
(58) Field of Classification Search
None
See application file for complete search history.

(56) References Cited

U.S. PATENT DOCUMENTS

| | | |
|---|---|---|
| 2002/0037587 A1 | 3/2002 | Gentz et al. |
| 2003/0017576 A1* | 1/2003 | Aquin et al. ............... 435/252.3 |

FOREIGN PATENT DOCUMENTS

| | | |
|---|---|---|
| JP | 2003-144180 | 5/2003 |
| WO | 00/17343 | 3/2000 |
| WO | 01/83786 | 11/2001 |
| WO | 2004/065556 | 8/2004 |

OTHER PUBLICATIONS

Nelson et al. (2003) Uniport accession No. Q88K12.*
Rhem et al. J. Biol. Chem. (1998) 273(37, 24044-2051.*
DeLorenzo, V et al (1990) Mini-Tn5 Transposon Derivatives for Insertion Mutagenesis, Promoter Probing, and Chromosomal Insertion of Cloned DNA in Gram-Negative Eubacteria Journal of Bacteriology 172(11):6568-6572.
Langenbach et al., Functional expression of the PHA synthase gene phaC1 from *Pseudomonas aeruginosa* in *Escherichia coli* results in poly(3-hydroxyalkanoate) synthesis, FEMS Microbiology Letters, 1997, vol. 150, No. 2, pp. 303-309.
Tsuge et al., "Molecular characterization and properties of (R)-specific enoyl-CoA hydratases from *Pseudomonas aeruginosa*: metabolic tools for synthesis of polyhydroxyalkanoates via fatty acid beta-oxidation", International Journal of Biological Macromolecules, 2003, vol. 31, No. 4-5, pp. 195-205.
Fiedler et al., "The role of the fatty acid beta-oxidation multienzyme complex from *Pseudomonas oleovorans* in polyhydroxyalkanoate biosynthesis: molecular characterizaton of the fadBA operon from *P. oleovorans* and of the enoyl-CoA hydratase genes phaJ from *P. oleovorans* and *Pseudomonas putida*", Archives of Microbiology, 2002, vol. 178, No. 2, pp. 149-160.
Hou et al., "Genome sequence of the deep-sea gamma-proteobacterium *Idiomarina loihiensis* reveals amino acid fermentation as a source of carbon and energy", Proceedings of the National Academy of Sciences of the United States of America, 2004, vol. 101, No. 52, pp. 18036-18041.
Golyshin et al., "Genome sequence completed of *Alcanivorax borkumensis*, a hydrocarbon-degrading bacterium that plays a global role in oil removal from marine systems", Journal of Biotechnology, 2003, vol. 106, No. 2-3, pp. 215-220.
De Lorenzo et al., Database EDatabase EMBL (Online), "*Escherichia coli* mini-Tn5 kanamycin transposon", Accession No. EC32991, 1995.
Nierman et al., Database EMBL (Online), "*Caulobacter crescentus* CB15 section 189 of 359 of the complete genome", Accession No. AE005863, 2001.
Nierman et a., Database EMBL (Online), "*Caulobacter crescentus* CB15 section 242 of 359 of the complete genome", Accession No. AE005916, Mar. 22, 2001.
Barbe et al., Database UNIPROT (Online), "Putative acyl-CoA thioesterase II (EC 3.1.2-)", Accession No. Q6FF63, Jul. 5, 2004.
Barbe et al., Database EMBL (Online), "*Acinetobacter* sp. ADP1 complete genome", Accession No. CR543861, Jun. 30, 2004.
Stover et al., Database EMBL. (Online), "*Pseudomonas aeruginosa* PAO1, section 274 of 529 of the complete genome", Accession No. AE004713, Sep. 1, 2000.
Stover et al., Database EMBL (Online), "Hypothetical protein", Accession No. Q9HZX5, Mar. 1, 2001.
Nierman et al., Database UNIPROT (Online), "Hypothetical protein CC2472", Accession No. Q9A5H5, Jun. 1, 2001.
Feil et al., Database EMBL (Online), "*Pseudomonas syringae* pv. B728a, complete genome", Accession No. CP000075, May 13, 2005.

(Continued)

*Primary Examiner* — Nashaat Nashed
(74) *Attorney, Agent, or Firm* — Klauber & Jackson LLC

(57) ABSTRACT

The present invention is in the field of biosynthesis of polyhydroxyalkanoates (PHA). The invention relates to a genetically engineered microorganism having at least one gene involved in the metabolism, preferably in the production, of polyhydroxyalkanoates (PHA). This microorganism is useful in commercial production of polyhydroxyalkanoates. The present invention further relates to a method for the production of polyhydroxyalkanoates (PHA).

15 Claims, 33 Drawing Sheets

(56) References Cited

OTHER PUBLICATIONS

Zhong Zheng et al., "Thioesterase II of *Escherichia coli* Plays an Important Role in 3-Hydroxydecanoic Acid Production", vol. 70, No. 70, (2004). pp. 3807-3813.

K.E. Nelson et al., Complete Genome Sequence and Comparative Analysis of the Metabolically Versatile *Pseudomonas putida* KT2440, vol. 4, No. 12, (2002) pp. 799-808; Database.

Chen et al., "Microbial Production and Applications of Chiral Hydroxyalkanoates," Appl Microbio Biotechnol, 67:592-299 (2005).

Schneiker et al., "Genome Sequence of the Ubiquitous Hydrocarbon-Degrading Marine Bacterium *Alcanivorax borkumensis*," Nature Biotechnology, 24(8):997-1004, (Aug. 2006).

Rock et al., "Phospholipid Synthesis in *Escherichia coli*", The Journal of Biological Chemistry, 1981, vol. 256, No. 2, pp. 736-742.

Poirier et al., "Increased flow of fatty acids toward beta-oxidation in developing seeds of *Arabidopsis* deficient in diacylglycerol acyltransferase activity or synthesizing medium-chain-length fatty acids", Plant Physiology, 1999, vol. 121, pp. 1359-1366.

\* cited by examiner

PHA production in *A.borkumensis* SK2 and the mutant strain on either 2% pyruvate or 1.5% octadecane as carbon sources.

Electron microscopy images of the ultrathin sections of *A.borkumensis* SK2

Scanning electron microscopy images (A and B) and electron microscopic images of the shadow-casted cells (C and D) of the wild type (left) and the mutant (right) prepared as it is described in the Materials and Methods. Cells were cultivated in ONR7a containing 1.5% (w/v) octadecane and 0.27 g/l of $NH_4Cl$ (storage conditions) and were harvested in the stationary phase of growth..

Growth characteristics of *A.borkumensis* wild type and mini-Tn5 mutant grown on pyruvate or octadecane under the conditions of high C:N ratio.

Table 1. *In silico* analysis of sequence data on the genes for polyhydroxyalkanoate production and mobilization in Alcanivorax borkumensis SK2

| Gene number in Alcanivorax | Annotated as | Homologous to | Closest homolog % similarity, % identity | Function |
|---|---|---|---|---|
| Abo_1335 | phaC synthase | PhaC synthase | *Acinetobacter sp.* ADP1 30% identity, 53% similarity | PHA synthesis, last step |
| Abo_2062 | phaC synthase | PhaC synthase | *Acinetobacter sp.* ADP1 34% identity, 56% similarity | PHA synthesis, last step |
| Abo_1526 | dienelactone hydrolase family protein | poly(3-hydroxyalkanoate) synthase | *Thiocystis violacea* 29% identity 45% similarity | PHA synthesis, last step |
| Abo_2240 | Conserved hypotetical protein | poly(3-hydroxybutyrate) depolymerase | *Alcaligenes faecalis* 29% identity 41% similarity | PHA depolymerization |
| Abo_1424 | Conserved hypotetical protein | D(-)-3-hydroxybutyrate oligomer hydrolase | *Ralstonia pickettii* 24% identity 46% similarity | Intracellular PHA depolymerization |
| Abo_1041 | transglutaminase-like superfamily domain protein | polyhydroxyalkanoate depolymerase precursor | *Rhodopirellula baltica* SH 1 36% identity 59% similarity | PHA depolymerization |
| Abo_915 | Conserved hypotetical protein | PhaF, poly(hydroxyalcanoate) granule associated protein | *Acinetobacter sp.* ADP1 37% identity 60% similarity | Granule formation, regulation of PHA synthesis |
| Abo_425 | Hypotetical protein | PhaF, polyhydroxyalkanoate synthesis protein | *Pseudomonas aeruginosa* PAO1 26% identity; 52% similarity | Granule formation, regulation of PHA synthesis |

Figure 5

Table 2. Polyhydroxyalkanoate composition in cells of *Alcanivorax borkumensis*

| Sample | Amount PHAs (mg/l) | PHA monomer composition of hydroxyalkanoates (mol%) | | | |
|---|---|---|---|---|---|
| | | (C6) | (C8) | (C10) | (C12) |
| SK2 pyruvate | 6.5 | 2 | 24 | 46 | 28 |
| SK2 cells octadecane | 18 | 2 | 20 | 48 | 30 |
| C9 mutant cells octadecane | n.d | n.d. | n.d. | n.d. | n.d. |
| C9 mutant supernatant octadecane | 2960 | 9 | 15 | 35 | 41 |
| C9 mutant cells pyruvate | n.d | n.d. | n.d. | n.d. | n.d. |
| C9 mutant supernatant pyruvate | 134 | 4 | 18 | 37 | 39 | n.d. not determined. The amount of PHA was too low for quantification.

Results indicate the average of two independent analyses. The standard deviation did not exceed 5%.

Figure 6

Table 3. Molecular weight of PHA from *A. borkumenis*

| Sample[1] | MW PHA (kDa) | | | |
|---|---|---|---|---|
| | Hydroxyhexanoate (MW monomer: 132.2 Da) | Hydroxyoctanoate (MW monomer: 160.2 Da) | Hydroxydecanoate (MW monomer: 188.3 Da) | Hydroxydodecanoate (MW monomer: 216.3 Da) |
| C9 Mutant octadecane | 330 | 325 | 207 | 540 |
| C9 Mutant pyruvate | 316 | 327 | 217 | 549 |
| Wild type octadecane | 250 | 247 | 180 | 432 |
| Wild type pyruvate | 258 | 241 | 189 | 426 |

[1]Supernantants were used when analyzing C9 mutant, and cells when using wild type strains.

Figure 7

Hypothetical pathway of A. borkumensis SK2 grown hydrocarbons/pyruvate

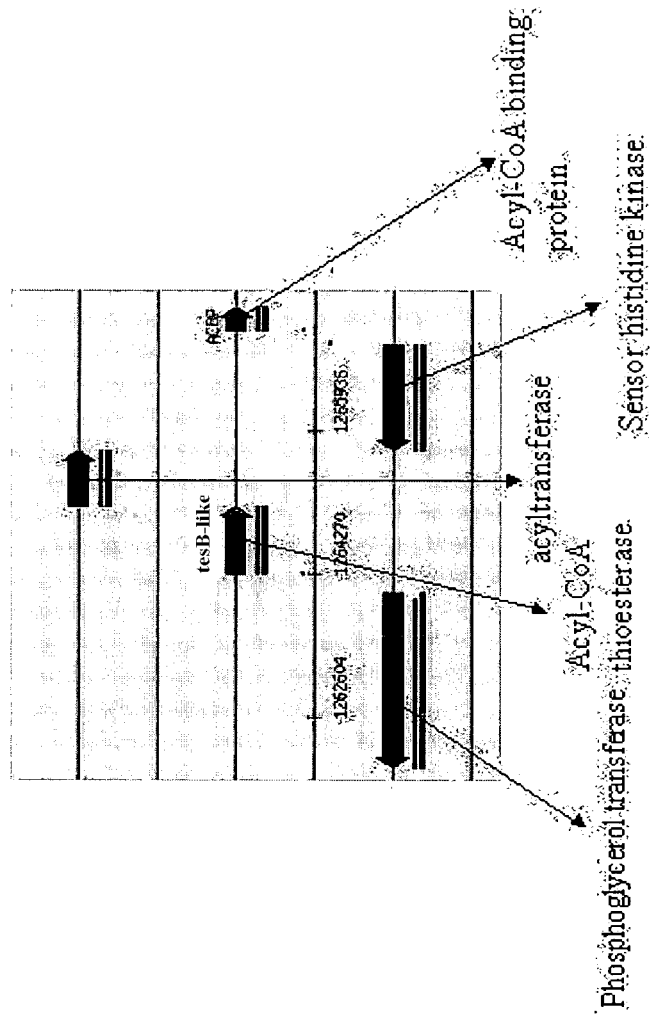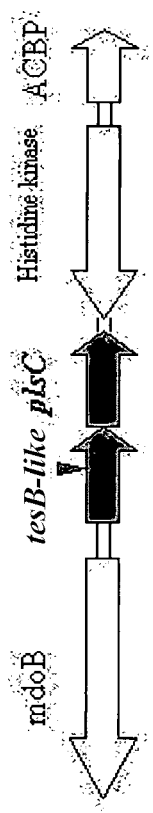
Figure 9

Table 4. Putative Acyl-CoA thioesterase proteins in other gram-negative bacteria encoded by genes homologous of the tesB-like gene of *A. borkumensis* SK2 (Abo_1044)

| Species | Name of the homologous gene | % Identity (% similarity) to Abo_1044 |
|---|---|---|
| *Pseudomonas putida* KT2440 | putative acyl-CoA thioesterase II | 40 (60) |
| *Pseudomonas aeruginosa* PA01 | hypothetical protein PA2871 | 41 (56) |
| *Pseudomonas syringae* pv B728a | acyl-CoA thioesterase II, putative | 42 (59) |
| *Pseudomonas fluorescens* PfO-1 | Acyl-CoA thioesterase | 42 (59) |
| *Idiomarina loihiensis* L2TR | tesB-like acyl-CoA thioesterase | 42 (57) |
| *Acinetobacter sp.* ADP1 | putative acyl-CoA thioesterase II | 36 (54) |
| *Caulobacter crescentus* CB15 | hypothetical protein CC2472 | 29 (47) |

Figure 10

Nucleic sequences of the two genes *tesB-like* (underlined) and „putative acetyltransferase" (black colour) consisting an operon. The first line is the region upstream from the *tesB-like* gene. The start codon of the *tesB-like* gene is atg and marked in bold letters. The Tn5 insertion took place at position 527 within *tesB-like* gene and marked with //. Downstream from the *tesB-like* gene is „putative acetyltransferase" gene. There is overlap in 3 bp.

```
ggcttcgcag gaatggtaaa taaagcaccg caaattcaaa acacgcagaa gtgagagacc
atgacattcg atgagattct agccacgatt gatggccagg gtaacgccac gtttccagaa
gggtgggggc agggccggac cttatttggt ggcctggtgg gggcggtgct gtttgaacat
ttagaaaaaa ccgtggctcg cgggaggttt ctacgtagtt tttctctctc ttttgtcgcc
cctgcggtgc cgggtccggt ggcactagac gagactgtgt ttcgggaagg caaatccgtt
atgcaggcca tggtctccgc ccgtcaagga gggcaggtgg tggcggttat gttggccagc
tttggggcca gtcgccaatc cagtgtagtg gtagaagggc catcggcccc agtgatgaaa
tctccagagc agagtatttc ggtaccgttt atcaaaggat tgacgccgga ttttttttcc
cattttaata tccattacgc agaaggcatg ccgccgttca gtggcagttc tgagcccgat
tacggtggtt acatggggtt tactgtgccg ccggaaacca tgagcac//cgc agcgctgatt
gcattggtgg atacctgggc gccttcagtt ttacctctgc tcaaagggcc agcacccgcc
agttccttga cctggaccat ggagctcttg gatgaccta gtgtccactc gccggagact
ttatggcaat atcgggtaaa cacggaccaa tgcagtgatg gctatggtca aagtcaggcg
gtggtttggg atgctgcggg taaggctgtg gcgttgagtc gacaaacctt tacggtattt
gcatgaaatc ggaactggtg ccactcacgg cgcggacttt aggtaagcaa gtgcctcgtc
gtgggcactg gctgttggcg gcgctagggc ggctgatttt gactgttatg gggtggcgta
ttgttggtga tttgcccgat acgcctcggg cagttttggc ggtggcgcca cacacgtcga
acatagacgg ggtcattggt atcagtgcta ttcagtcttt gcgcttggat gtgcgcttca
tgggtaagca cacgttgttt aaaggtcgtc ttgggcggtt catgtactgg ctgggcggca
tccctgtgaa tcgagaaagt gccagggatg tggtggacca gacgacgtcg gtgatggggg
aaacaccatt ttggcttggg ctaacgccgg aggggacgcg taaaggcgcc aagcgttgga
aaaccgggtt ttaccgtatt gctgagcaaa tgcaggtgcc gattgtcgtg ttaggtttct
gttaccggcg ccggcaggtc cggattgtag attgctttct gccgacgggc gatattgatg
ctgatatggc gcgaatgacc gcgtcgttgg cggatattgt tccgcgcaaa cctgcgcagt
tatccgcccc gctgaaagcg gaaaaagctg ctcgcggcat tgattgattc agacgttggc
agttttgccg gactgatcaa ggagatgctg gcggtgctgg gcggat
```

Figure 11

Nucleotide sequence of tesB-like acyl-CoA thioesterase (Abo_1044), start and stop codons are marked in bold. The Tn5 insertion took place at position 557 and is marked //.

```
atgacattcg atgagattct agccacgatt gatggccagg gtaacgccac gtttccagaa
gggtggggc agggccggac cttatttggt ggcctggtgg gggcggtgct gtttgaacat
ttagaaaaaa ccgtggctcg cgggaggttt ctacgtagtt tttctctctc ttttgtcgcc
cctgcggtgc cgggtccggt ggcactagac gagactgtgt ttcgggaagg caaatccgtt
atgcaggcca tggtctccgc ccgtcaagga gggcaggtgg tggcggttat gttggccagc
tttggggcca gtcgccaatc cagtgtagtg gtagaagggc catcggcccc agtgatgaaa
tctccagagc agagtatttc ggtaccgttt atcaaaggat tgacgccgga tttttttttcc
cattttaata tccattacgc agaaggcatg ccgccgttca gtggcagttc tgagcccgat
tacggtggtt acatggggtt tactgtgccg ccggaaacca tgagcaccgc agcgctgatt
gcattggtgg atacctg//ggc gccttcagtt ttacctctgc tcaaagggcc agcacccgcc
agttccttga cctggaccat ggagctcttg gatgacccta gtgtccactc gccggagact
ttatggcaat atcgggtaaa cacggaccaa tgcagtgatg gctatggtca aagtcaggcg
gtggtttggg atgctgcggg taaggctgtg gcgttgagtc gacaaacctt tacggtattt
gcatga
```

Figure 12

Amino acid sequence of the tesB-like acyl-CoA thioesterase

```
MTFDEILATI DGQGNATFPE GWGQGRTLFG GLVGAVLFEH LEKTVARGRF LRSFSLSFVA
PAVPGPVALD ETVFREGKSV MQAMVSARQG GQVVAVMLAS FGASRQSSVV VEGPSAPVMK
SPEQSISVPF IKGLTPDFFS HFNIHYAEGM PPFSGSSEPD YGGYMGFTVP PETMSTAALI
ALVDTWAPSV LPLLKGPAPA SSLTWTMELL DDPSVHSPET LWQYRVNTDQ CSDGYGQSQA
VVWDAAGKAV ALSRQTFTVF A
```

Figure 13

Nucleotide sequence of miniTn5 Km coding repeats functional in transposition and neomycin phosphotransferase, responsible for neomycin and kanamycin resistance. The repeats functional in transposition are marked in bold. The first repeat (1.....19) is called Tn5 I end, the second repeat (2338...2356) is called Tn5 O end. In the case of Tn5 Str/Sp element the kanamycin resistance gene is replaced by streptomycin resistance gene.

CTGTCTCTTGATCAGATCTGGCCACCTAGGCCGAATTCCCGGGGATCCGGTGATTGATTGAGCAAGCTTT
ATGCTTGTAAACCGTTTTGTGAAAAAATTTTTAAAATAAAAAAGGGGACCTCTAGGGTCCCCAATTAATT
AGTAATATAATCTATTAAAGGTCATTCAAAAGGTCATCCACCGGATCACCTTACCAAGCCCTCGCTAGAT
TGTTAATGCGGATGTTGCGATTACTTCGCCCAACTATTGCGATAACAAGAAAAGCGCCTTTCATGATATA
TCTCCCAATTTTGTGTAGGGCTTATTATGCACGCTTAAAAATAATAAAAGCGACTTGACCTGATAGTTTG
GCTGTGAGCAATTATGTGCTTAGTGCATCTAACGCTTGAGTTAACCGCGCCGCGAAGCGGCGTCGGCTTG
AACGAATTGTTAGACATTATTTGCCGACTACCTTGGTGATTCGCCTTTCACGTAGTGGACAAAATCAACC
AACTGATCTGCGCGAGCTTCACGCTGCCGCAAGCATCAGGGCGCAAGGGCTGCTAAAGGAAGCGGAACAC
GTAGAAAGCCAGTCCGCAGAAACGGTGCTACCCCGGATGAATGTCAGCTACTGGGCTATCTGGACAAGGG
AAAACGCAAGCGCAAAGAGAAAGAGGTAGCTTGCAGTGGGCTTACATGACGATAGCTAGACTGGGCGGTT
TTATGGACAGCAAGCGAACCGGAATTGCCAGCTGGGGCGCCCTCTGGTAAGGTTGGGAAGCCCTGCAAAG
TAAACTGGATGGCTTTCTTGCCGCCAAGGATCTGATGGCGCAGGGGATCAAGATCTGATCAAGAGACAGG
ATGAGGATCGTTTCGCATGATTGAACAAGATGGATTGCACGCAGGTTCTCCGGCCGCTTGGGTGGAGAGG
CTATTCGGCTATGACTGGGCACAACAGACAATCGGCTGCTCTGATGCCGCCGTGTTCCGGCTGTCAGCGC
AGGGGCGCCCGGTTCTTTTTGTCAAGACCGACCTGTCCGGTGCCCTGAATGAACTGCAGGACGAGGCAGC
GCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGA
AAGTATCCATCATGGCTGATGCAATGCGGCGGCTGCATACGCTTGATCCGGCTACCTGCCCATTCGACCA
CCAAGCGAAACATCGCATCGAGCGAGCACGTACTCGGATGGAAGCCGGTCTTGTCGATCAGGATGATCTG
GACGAAGAGCATCAGGGGCTCGCGCCAGCCGAACTGTTCGCCAGGCTCAAGGCGCGCATGCCCGACGGCG
AGGATCTCGTCGTGACCCATGGCGATGCCTGCTTGCCGAATATCATGGTGGAAAATGGCCGCTTTTCTGG
ATTCATCGACTGTGGCCGGCTGGGTGTGGCGGACCGCTATCAGGACATAGCGTTGGCTACCCGTGATATT
GCTGAAGAGCTTGGCGGCGAATGGGCTGACCGCTTCCTCGTGCTTTACGGTATCGCCGCTCCCGATTCGC
AGCGCATCGCCTTCTATCGCCTTCTTGACGAGTTCTTCTGAGCGGGACTCTGGGGTTCGAAATGACCGAC
CAAGCGACGCCCAACCTGCCATCACGAGATTTCGATTCCACCGCCGCCTTCTATGAAAGGTTGGGCTTCG
GAATCGTTTTCCGGGACGCCGGCTGGATGATCCTCCAGCGCGGGGATCTCATGCTGGAGTTCTTCGCCCA
CCCCGGGCTCGATCCCCTCGCGAGTTGGTTCAGCTGCTGCCTGAGGCTGGACGACCTCGCGGAGTTCTAC
CGGCAGTGCAAATCCGTCGGCATCCAGGAAACCAGCAGCGGCTATCCGCGCATCCATGCCCCCGAACTGC
AGGAGTGGGGAGGCACGATGGCCGCTTTGGTCGACCCGGACGGGACGGATCAGTGAGGGTTGCAACTGT
GGGTCAAGGATCTGGATTTCGATCACGGCACGATCATCGTCGGGAGGGCAAGGGCTCCAAGGATCGGCC
TTGATGTTACCGAGAGCTTGGTACCCAGTCTGTGTGAGCAGGGGAATTGATCCGGTGGATGACCTTTTGA
ATGACCTTTAATAGATTATATTACTAATTAATTGGGGACCCAGAGGTCCCCTTTTTTATTTTAAAAATT
TTTTCACAAAACGGTTTACAAGCATAAAGCTTGCTCAATCAATCACCGGATCCCCGGGAATTCGTCGACA
AGCTGCGGCCGCCTAGGCCGTGGCCGAACTTGTGTATAAGAGTCAG

Figure 14

Amino acid sequence of neomycin phosphotransferase responsible for neomycin and kanamycin resistance.

MIEQDGLHAGSPAAWVERLFGYDWAQQTIGCSDAAVFRLSAQGRPVLFVKTDLSGA
LNELQDEAARLSWLATTGVPCAAVLDVVTEAGRDWLLLGEVPGQDLLSSHLAPAEK
VSIMADAMRRLHTLDPATCPFDHQAKHRIERARTRMEAGLVDQDDLDEEHQGLAPA
ELFARLKARMPDGEDLVVTHGDACLPNIMVENGRFSGFIDCGRLGVADRYQDIALAT
RDIAEELGGEWADRFLVLYGIAAPDSQRIAFYRLLDEFF

Figure 15

Nucleotide sequence of a putative acyltransferase (Abo_1045), start and stop codons are marked in bold. There is a 4 nucleotides overlap with the previous open reading frame of tesB-like acyl-CoA thioesterase (Abo_1044)

```
atgaaatcgg aactggtgcc actcacggcg cggactttag gtaagcaagt gcctcgtcgt
gggcactggc tgttggcggc gctagggcgg ctgattttga ctgttatggg gtggcgtatt
gttggtgatt tgcccgatac gcctcgggca gttttggcgg tggcgccaca cacgtcgaac
atagacgggg tcattggtat cagtgctatt cagtctttgc gcttggatgt gcgcttcatg
ggtaagcaca cgttgtttaa aggtcgtctt gggcggttca tgtactggct gggcggcatc
cctgtgaatc gagaaagtgc cagggatgtg gtggaccaga cgacgtcggt gatgggggaa
acaccatttt ggcttgggct aacgccggag gggacgcgta aggcgccaa gcgttggaaa
accgggtttt accgtattgc tgagcaaatg caggtgccga ttgtcgtgtt aggtttctgt
taccggcgcc ggcaggtccg gattgtagat tgctttctgc cgacgggcga tattgatgct
gatatggcgc gaatgaccgc gtcgttggcg gatattgttc cgcgcaaacc tgcgcagtta
tccgccccgc tgaaagcgga aaagctgct cgcggcattg attga
```

Figure 16

Amino acid sequence of "putative acyltransferase".

```
MKSELVPLTA RTLGKQVPRR GHWLLAALGR LILTVMGWRI VGDLPDTPRA VLAVAPHTSN
IDGVIGISAI QSLRLDVRFM GKHTLFKGRL GRFMYWLGGI PVNRESARDV VDQTTSVMGE
TPFWLGLTPE GTRKGAKRWK TGFYRIAEQM QVPIVVLGFC YRRQVRIVD CFLPTGDIDA
DMARMTASLA DIVPRKPAQL SAPLKAEKAA RGID
```

Figure 17

Nucleotide sequence of putative acyl-CoA thiosterase II of *Pseudomonas putida* KT2440 (GeneID:1045294)

```
ATGACTTTCAACCAACTGCTCGACGCCGTGCGGGCCAACCCGGATTCCGTCAGCATTCCGCCCAGCTGGG
CCCAGGGGCGCGCTGCCTTTGGCGGGCTGATGGCGGCCATGGTCTATGAAACCATGCGCCTCAAGATCAG
CGACAACCGCCCGGTACGCTCATTGGCCATCAGCTTCGTGGCACCCGCGGCGGCGGATGTGCCCATCCGC
TTCGAGGTGGAGGTTTTGCGCGAAGGCAAGGCGGTTAGCACGTTGCTGGGCCGCGCTGTTCAGGATGGCC
AGGTGGTGACTTTGGTGCAGGGCAATTTCGGTGCGGGCCGCCCTTCGGTGGTCGAAGTGCCGGCGTTGCC
GGCCATCGAAATGCCTGCGCTCGATGAGGCGGCCCCGGAGTTGCCCTATATCAAAGGCGTTACCCCTGAG
TTCATGCGGCACGTGGCCCTGCGCTGGGCAGTAGGTGGGCTGCCGTTCAGTGGCAATCAGTCGCGCAAGA
TGGGCGGCTGGGTGCGCTTGCGGGATGTGGTGGAAGAACAGGTGAACGAGGCGCACCTGTTGGCGTTGGT
CGATGCCTGGCCGCCCAGCCTCATGCCGTTTCTCAAGCAGCCCGCTGCGGGCAGTACGTTGACCTGGACC
ATCGAGTTCATCCAGCCAACGGCGAAGCTGTCGACCCTGGATTGGTGCCGGTACTGTGTGGAGACCGAGC
ATGCGCGGGATGGCTATGGGCATGCTGCTGCGGCGTTGTGGACGGCGCAGGGCGAGTTGTTGGCGTTGAG
CCGGCAGACCGTCACCGTTTTCGCCTGA
```

Figure 18

**Nucleotide sequence of hypothetical protein PA2871 of *Pseudomonas aeruginosa* PA01 (GeneID:882599)**

```
ATGAATTTTTCCGAATTGATCCAGGCGGTCCGCCGCGACCCTTCCTCGGTGGTAGTACCGGCCAGTTGGG
GCCAGGGCCGCGCCACCTTCGGTGGCCTGGTGGTGGCGTTGGCCTACGAGGCCATGCTTGCGGTGGTCGA
GGCGGGGCGTCCGTTGCGCTCCATCGGCGTCAGCTTCGTCGGACCGCTGGCCCCCGAGCAGCCGGCGAGC
TTCAGCGCCCGGTTGTTGCGCGAGGGCAAGGCGGTGAGCCAGGTCCAGGTCGAGGTCCGTCAGGGCGAGC
AGGTGGTGACGCTGGTCCAGGCCAGTTTCGGCGTCGCCCGCGCATCGGCGGTGGCGGTGGAAGCGTTGCC
GGCGGCCGGGATGAAGGGCCCCGAAGAGAGCCAGGAGCTGCCCTATATCCGTAACGTGACCCCGGAGTTC
ACTCGCTACATCGCCATGCGCTGGGCAGTGGGCGGCCTGCCGTTCTCTTCGAACAAGTCGCGCCAGATGG
GCGGCTGGATGCGTTTCCGCGACGAACCCGAGGGAGAGCCCATGGAGGTTTCCCACCTGCTGGCGCTGCT
CGACTCCTGGCCGCCGGCGCTGTTGCCGCACCTGGGCACCCCGGCGATGGCCAGCTCGCTGACCTGGACC
GCCGAGTTCCTCCAGCCGCTGCCGCAGCAAGGCAGCGGCGACTGGTGCCGTTACCTGGCGGAGATCGAGG
AGGCGCGTGACGGCTACGGCCACGTGGCGGCGCGGATGTGGAGCGCCGACGGCCAGTTGCTGGCGATCAG
CCGGCAGATGGTCACGGTGTTCGGCTGA
```

Figure 19

**Nucleotide sequence of acyl-CoA thioesterase II, putative of *Pseudomonas syringae* pv B728a (GeneID:3367571)**

```
ATGACCTTTTCTGAACTGATCGATGCGCTGCGTCGCGATCCGCGCTCTGTCACGATCCCTGCCGAATGGT
CTCAAGGGCGTGCCTGCTTCGGCGGGCTGATGGCTGCGCTGACCTACGAAGCGATGCGTGCACAGGTGCC
GGAAGGGCGGCCGGTTCGTTCGTTGGCGATCACCTTTGTCGGGCCGGCCGCGCCCGGTGTGCCGATTGCT
TTCGAGGTCGACACCCTGCGCCATGGCAAGGCAGTCAGTCAGGTGCTGGGACGCGCCATGCAGAACGGTC
AGGTCATGACCCTGATACAAGGCAGCTTCGGTGCCCCTCGGGAATCGATGATCACCGTTGCCGCAGAGGC
CGCGCCGGTCCTTAAACCGGTTGATCAATGTCCGGAGCTGCCGTTCGCCAGCGGCGTGATGCCTGATTAC
CTGCGCTTCATGGACATCCGCTGGGCGTTGGGCGGCATGCCATTCAGTAATACCCGATCACCGGCGATTG
GCGGCTACGTGCGCTTTCGCGATACGCCGCACGCCACGCCCATGAGCGAAGCGCACATTCTGGCGCTGGT
GGACACCTGGCCGCCTGCGGTACTGCCGCACCTGGACAAACCGGCCCCCGGCAGCTCACTGACCTGGACC
ATTGAGTTCGTCCAGCCCCAGCCGTCGCTCGATACCCTGCAGTGGTGCAGCTACCGCGCAGTCATCGAGC
ATGCCCGCGATGGCTATGGCCATACCGCCGCGGCATTGTGGAGCCCCGACGGCGAGCTGATCGCAATCAG
CCGCCAGACGGTTACCGTATTTGGCTGA
```

Figure 20

**Nucleotide sequence of acyl-CoA thiosterase of *Pseudomonas fluorescens* PfO-1 (locus_tag=Pflu02003109)**

ATGCGCTTTTGCGATCTGATCGATGCTGTCCGTCGTCAACCGGAGGTCACGATTCCGGCGGAGTGGGGCC
AGGGCCGGGCCAGTTTTGGCGGGCTGGTGGCCGCGCTGCAATTTGAAGTGATGCGCACCAAGGTTCCGAC
CGATCGGCCGGTACGTTCGCTGGCGATCACCTTCGTCGGCCCGGTCGAGCCCGAAGTGCCGGTGAGTTTT
GAAGTCGAGGTACTACGCGAAGGCAAAGCGGTCAGCCAGGTGCTGGGGCGTGCTGTGCAGAACGGTCAGG
TGGTGACGATGGTGCAAGGCAGCTTCGGGGCTTCGCGGCCATCGGAAGTGGCGGTTGAAGCCTATCCCGC
GCCGGAAATGAAGCACTGGGACGATTGCCAGGAACTGCCGTACATCAAAGGCGTAACCCCCGAGTTCATG
CGTCATCTGGCGATGCGCTGGAGCGTTGGCGGGATGCCGTTCACCGGCAATCAATCGCGGCTGATGGGTG
GCTGGGTGCGCCTGCGTGGGGATGTGAAGGAAGAGTCGGTCAACGAAGCGCACCTGCTGGCGCTGGTCGA
TGCCTGGCCACCAGCGCTGTTGCCGTACCTGAAGAAACCGGCACCGGGCAGTACGCTGACCTGGACCATC
GAATTCGTTCAGCCGTTACGCGATTTGAGTACGCTGGATTTTTGCCAATACCTGGCGGACATCGAGTATG
CCGCCGACGGTTACGGCCACGTCGCCGCCAAGCTGTGGAGTGCGAAGGGTGAACTGATTGCCATGAGTCG
GCAGACGGTGACGATCTTCGCCTGA

Figure 21

**Nucleotide sequence of tesB-like acyl-CoA thiosterase of *Idiomarina loihiensis* L2TR (locus_tag="IL0656")**

```
ATGAACTTCCACACAGCTGTAGAACAAATCGTTGCGGATAAGAACAATCAAGTCATTGAACTACCTTCCG
GCTGGGCTCAGGGACGCGCGTTTTTCGGCGGATTCAGCGGAGCATTGGCTGCTCAGTTTTTGTTGAAACA
ATTTCCGATTGAATATCATCTTCGTTCCATGAGTATCTCTTTTGTCGCGCCTGCTGAACCGGGTGAGGCT
GAGTTAAATTACCGAATTTTGCGCGAGGGAAAATCGGTTATTCAGGTTGCTGTCGAACTGCAGCAGCAAG
GGCAGATTATGTTGTCTTGTCTGGCGAGCCTGGGCAAAGGCCGAAGTTCAACGGTTACAGTGGTAAGTGA
AACGCCACCCGATCTTAAAACCATCAACGACGGACCAGGTTTACCTGAAGCGGATATTGTCCCAGAGTTT
GCGAAAAACTTCGATTACCGTATTACGTCAGGTGGTATGCCATTTAGCGGACAACCGGGAAGAACTTTTG
GTGGCTGGATACGTTTTCGTGAAGAACAACAGCCGCTGACAACGGCAACTATACTGGCTTTAGTTGACGC
CTGGCCACCGGCAGTCTTGCCTCATCTGGACAGCCCTGCGCCGGCCTCGTCTTTAACCTGGACTATTGAG
TTTCCCGATATTCCTCTACAAAGTTTCAGTAGCCACGACTGGTTTCAGTACGAAGCTTTTATTGAGCATG
CTGAAAATGGTTATGGGCACAGCCGCGCGGGTCTGTGGAGTGAGAAGGGCGAGTTATTAGCTATAAGTCG
ACAGACTTTTACGGTATTTGCGTAA
```

Figure 22

**Nucleotide sequence of putative acyl-CoA thioesterase II of *Acinetobacter sp.* ADP1 (locus_tag="ACIAD0341)**

```
ATGAGTGATGCTATGCCTTTAGATCAGACATTGGAACAACTGACGCAAGATGAATGGATTGATATTCCCC
AAGGCTGGTCGCAGGGAAGAACGATTTATGGTGGATTGGTTGCAGGCTTGCTCATGCATAAAGCATTAAG
TGTGATGAATGATGAGTCCAAAAATCTGTTAAGTACCAGCATTACTTTTGTGGGACCAGTGAATGAAGGG
CGGGTACGACTAACAGTTGAAATCTTGCGGCAGGGTAAATCTGTCACCACAATTGAGGCACGTTTATGGC
AGGACCAGGCTGTTCAAACCATCTTGATCGCAAGTTTCGGACAGCCGCGTTCTTCTGAAATTTTTGTGCT
TAACTTACCCGAGGCACCAGACTATTTGTCTCCCGAGCAGTTCTCAAGAATGCCTTTTGTAAAAATGATG
CCAGAATGCTATCAACAATTCGATCTGCGATGGGCAGAAGGTCATTATCCCATGACTCAACAAGCTCCAG
ATTTTGGTGGCTGGTGCCGTTACGATATCCAAAAACATTCACCGCGAGCATTGAATGTGGCTGATTTGTT
AATTTTGATGGATATCTGGCCACCAGGGGTACTGCCCATGTTTCAAACCATCGCACCTGCCAGTTCTCTA
ACATGGCATCTCACTTTTGTTCGTCCCGTTGCTTATGAGTTACATGATTGGTTTAAGTATCAGGTCGTCA
CGCAGCATGCTGCCTTTGGCTATGCTACAGAATATGCGCATTTATGGGATGCTCAAAACCGTCTGATTGC
TATTTCGAGGCAGACAGTTACTGTTTTTGCCTAG
```

Figure 23

**Nucleotide sequence of hypothetical protein CC2472 of *Caulobacter crescentus* CB15 (GeneID:943632)**

```
ATGACGCTCTACACCGACCTCGTCGCGGCCATCGCCTCGACCGAAACTGGCTTTTCCGCCCATGTCTCCG
ACGACTGGAAGCAAGGCCGCACCACCTATGGCGGCTTGAGCGGCGCCTTGTGCGTCGAGGCCGCCCTGCG
AGCCTTTCCCGAGGCCCCTCCTCTGCGCTCGGCGCAATTCGCCTTTGTCGGCCCGGCGGCCGGCGAGTTG
GCGATCTCGGTGCGGCCGCTGCGGCAGGGCAAGTCGACGCTTTTCGTCGCCGTCGATCTGATCGGCGAAC
AGGGCGTGGCCACCCACGGCGTGCTGACCTTCGGCGCGGCGCGGACCTCAGCCATCTCGTACGAAGAAGT
CCTCTGCCCGCCCGTGGCGCCGGCCGGCGCCTGTGAGCTGTTCTTCCCCGAAAATCGCCAGGGCGCGCCG
CACTTCTCGGCGCAGTTCGAGGTGCGCAAGGCCGGCGGCACGCGCCCCCTGGCCGGGGGTGAGCCGGAAT
ATCTGCTGTGGATCCGCCACCGCGATCCGGCCGCGACCTCGATCTCGGCCCTGGTGGCGTTGGCCGACAT
GCCGCCGCCCCGGCCATGGCGCTGTTCCCGCAGTTTGGGCCGATCTCGACCATGACCTGGTCGCTGGAT
ATCGTGGGCCTGCCCGAGGCGGACGACGACGGCTGGCGGCTGCTGCGCACCCGGGCCGAGACCATCGGCG
ACGGCTACTCGACCCAGGAGATGCATCTGTGGGACGCCAAGGGCCGCCCGCTGGTCCTGGCGCGACAGAA
CGTGGCGATCTTCGTCTGA
```

**Nucleotide sequence of hypothetical protein ELI0992 of *Erythrobacter litoralis* HTCC2594**
(locus_tag=ELI0992)

```
ATGTCCGTTTCCGATCTTCGTGCGCCGATCACGTCCGAAGGTGGCGCTGTCACTCTTCCAGCCGACAAAT
GGCTGCAGGGCCGCACGCTCTTTGGCGGAGCCTCGGCGCTTGTCGCCTACACCGCCGCGGTGCGCGCTTT
CCCCGATCTCCCGCCCTTGCGCGCAGCGCAGATCGGATTTGTCGCGCCGGTCGGAAAGGACGTGGAGACG
CGGGCCGCAATGGTCCGACAGGGTCGCAACGTCGCGCAGGTGCGCAGCGAACTGCTGGTCGAAGGCAAGG
TCGCGCTCACCGCATTCTGGCTGTTCGGAACCGGTCGCGAGGCCAACGCCGTACATGCCGCTGCCAAGGC
CGATCCCTGGCCCGGCGCACCGGAAGAGAACGATTCCGCGATGACCGACAAGGGCCCGCCTTTCATCGTC
AACAATTTCGACATTCGCCGCGCGCAGGAAACGCAAGGCCCCGGCGAACCGATCGTCCGGCGCTGGTTCA
GGCTGACCGATCGGGGCGAGCTCGATCGCGTATCGGAGCTGATCCTGGTGGGCGATACGCTGCCCCCGGG
CGCCATGCGCGCGATGCAGCGCCAGGGCCCGATCAGCTCGATCAACTGGTCGTTCAATATTCTCGATGCG
GAACTCGGCACGCGCGACGGCTGGTGGCTCGGCGAGACCGCCAGCCAGCATGCCGGTGCAGGCTATTCGA
GCGAGCGGCTACGGCTCTGGAATGCCGACGGCGTGCAGGTGATGGACGGATTGCAATCCGTTGCCGTCTT
CGGCTGA
```

Figure 25

**Amino acid sequence of putative acyl-CoA thiosterase II of *Pseudomonas putida* KT2440 (protein_id="NP_744457.1)**

```
MTFNQLLDAVRANPDSVSIPPSWAQGRAAFGGLMAAMVYETMRLKISDNRPVRSLAISFVAPAAADVPIRFEVEV
LREGKAVSTLLGRAVQDGQVVTLVQGNFGAGRPSVVEVPALPAIEMPALDEAAPELPYIKGVTPEFMRHVALRWA
VGGLPFSGNQSRKMGGWVRLRDVVEEQVNEAHLLALVDAWPPSLMPFLKQPAAGSTLTWTIEFIQPTAKLSTLDW
CRYCVETEHARDGYGHAAAALWTAQGELLALSRQTVTVFA
```

Figure 26

**Amino acid sequence of hypothetical protein PA2871 of *Pseudomonas aeruginosa* PA01 (protein_id="NP_251561.1)**

```
MNFSELIQAVRRDPSSVVVPASWGQGRATFGGLVVALAYEAMLAVVEAGRPLRSIGVSFVGPLAPEQPASFSARL
LREGKAVSQVQVEVRQGEQVVTLVQASFGVARASAVAVEALPAAGMKGPEESQELPYIRNVTPEFTRYIAMRWAV
GGLPFSSNKSRQMGGWMRFRDEPEGEPMEVSHLLALLDSWPPALLPHLGTPAMASSLTWTAEFLQPLPQQGSGDW
CRYLAEIEEARDGYGHVAARMWSADGQLLAISRQMVTVFG
```

Figure 27

Amino acid sequence of acyl-CoA thioesterase II, putative of *Pseudomonas syringae* pv B728a (protein_id="YP_235138.1)

```
MTFSELIDALRRDPRSVTIPAEWSQGRACFGGLMAALTYEAMRAQVPEGRPVRSLAITFVGPAAPGVPIAFEVDT
LRHGKAVSQVLGRAMQNGQVMTLIQGSFGAPRESMITVAAEAAPVLKPVDQCPELPFASGVMPDYLRFMDIRWAL
GGMPFSNTRSPAIGGYVRFRDTPHATPMSEAHILALVDTWPPAVLPHLDKPAPGSSLTWTIEFVQPQPSLDTLQW
CSYRAVIEHARDGYGHTAAALWSPDGELIAISRQTVTVFG
```

Figure 28

Amino acid sequence of acyl-CoA thiosterase of *Pseudomonas fluorescens* PfO-1 (protein_id="ZP_00264181.1)

```
MRFCDLIDAVRRQPEVTIPAEWGQGRASFGGLVAALQFEVMRTKVPTDRPVRSLAITFVGPVEPEVPVSF
EVEVLREGKAVSQVLGRAVQNGQVVTMVQGSFGASRPSEVAVEAYPAPEMKHWDDCQELPYIKGVTPEFM
RHLAMRWSVGGMPFTGNQSRLMGGWVRLRGDVKEESVNEAHLLALVDAWPPALLPYLKKPAPGSTLTWTI
EFVQPLRDLSTLDFCQYLADIEYAADGYGHVAAKLWSAKGELIAMSRQTVTIFA
```

Figure 29

**Amino acid sequence of tesB-like acyl-CoA thiosterase of *Idiomarina loihiensis* L2TR (protein_id=AAV81497.1)**

```
MNFHTAVEQIVADKNNQVIELPSGWAQGRAFFGGFSGALAAQFLLKQFPIEYHLRSMSISFVAPAEPGEAELNYR
ILREGKSVIQVAVELQQQGQIMLSCLASLGKGRSSTVTVVSETPPDLKTINDGPGLPEADIVPEFAKNFDYRITS
GGMPFSGQPGRTFGGWIRFREEQQPLTTATILALVDAWPPAVLPHLDSPAPASSLTWTIEFPDIPLQSFSSHDWF
QYEAFIEHAENGYGHSRAGLWSEKGELLAISRQTFTVFA
```

Figure 30

**Amino acid sequence of putative acyl-CoA thioesterase II of *Acinetobacter sp.* ADP1 (protein_id=CAG67294.1)**

```
MSDAMPLDQTLEQLTQDEWIDIPQGWSQGRTIYGGLVAGLLMHKALSVMNDESKNLLSTSITFVGPVNEGRVRLT
VEILRQGKSVTTIEARLWQDQAVQTILIASFGQPRSSEIFVLNLPEAPDYLSPEQFSRMPFVKMMPECYQQFDLR
WAEGHYPMTQQAPDFGGWCRYDIQKHSPRALNVADLLILMDIWPPGVLPMFQTIAPASSLTWHLTFVRPVAYELH
DWFKYQVVTQHAAFGYATEYAHLWDAQNRLIAISRQTVTVFA
```

Figure 31

Amino acid sequence of hypothetical protein CC2472 of *Caulobacter crescentus* CB15 (protein_id="NP_421275.1)

```
MTLYTDLVAAIASTETGFSAHVSDDWKQGRTTYGGLSGALCVEAALRAFPEAPPLRSAQFAFVGPAAGELAISVR
PLRQGKSTLFVAVDLIGEQGVATHGVLTFGAARTSAISYEEVLCPPVAPAGACELFFPENRQGAPHFSAQFEVRK
AGGTRPLAGGEPEYLLWIRHRDPAATSISALVALADMPPPPAMALFPQFGPISTMTWSLDIVGLPEADDDGWRLL
RTRAETIGDGYSTQEMHLWDAKGRPLVLARQNVAIFV
```

Figure 32

**Amino acid sequence of hypothetical protein ELI0992 of *Erythrobacter litoralis* HTCC2594**
(protein_id=ZP_00375750.1)

```
MSVSDLRAPITSEGGAVTLPADKWLQGRTLFGGASALVAYTAAVRAFPDLPPLRAAQIGFVAPVGKDVET
RAAMVRQGRNVAQVRSELLVEGKVALTAFWLFGTGREANAVHAAAKADPWPGAPEENDSAMTDKGPPFIV
NNFDIRRAQETQGPGEPIVRRWFRLTDRGELDRVSELILVGDTLPPGAMRAMQRQGPISSINWSFNILDA
ELGTRDGWWLGETASQHAGAGYSSERLRLWNADGVQVMDGLQSVAVFG
```

Figure 33

SEQUENCE LISTING

<160> NUMBER OF SEQ ID NOS: 31

<210> SEQ ID NO 1
<211> LENGTH: 1546
<212> TYPE: DNA
<213> ORGANISM: Alcanivorax borkumensis
<220> FEATURE:
<223> OTHER INFORMATION: Nucleotide sequences of the genes tesB-like
     (Abo_1044) and plsC (Abo_1045) consisting of an operon in
     Alcanivorax borkumensis (fig. 11)

```
<220> FEATURE:
<221> NAME/KEY: misc_feature
<222> LOCATION: (1)..(60)
<223> OTHER INFORMATION: Region upstream from the tesB-like gene
<220> FEATURE:
<221> NAME/KEY: misc_feature
<222> LOCATION: (61)..(63)
<223> OTHER INFORMATION: Start codon of tesB-like gene
<220> FEATURE:
<221> NAME/KEY: gene
<222> LOCATION: (61)..(847)
<223> OTHER INFORMATION: tesB-like acyl-CoA thioesterase (Abo_1044)
<220> FEATURE:
<221> NAME/KEY: misc_feature
<222> LOCATION: (844)..(847)
<223> OTHER INFORMATION: 4 nucleotides overlap of the two genes
<220> FEATURE:
<221> NAME/KEY: misc_feature
<222> LOCATION: (844)..(846)
<223> OTHER INFORMATION: Start codon of plsC
<220> FEATURE:
<221> NAME/KEY: gene
<222> LOCATION: (844)..(1547)
<223> OTHER INFORMATION: plsC (Abo_1045)

<400> SEQUENCE: 1
```

| | | | | | |
|---|---|---|---|---|---|
| ggcttcgcag | gaatggtaaa | taaagcaccg | caaattcaaa | acacgcagaa | gtgagagacc | 60 |
| atgacattcg | atgagattct | agccacgatt | gatggccagg | gtaacgccac | gtttccagaa | 120 |
| gggtggggc | agggccggac | cttatttggt | ggcctggtgg | gggcggtgct | gttttgaacat | 180 |
| ttagaaaaaa | ccgtggctcg | cgggaggttt | ctacgtagtt | tttctctctc | ttttgtcgcc | 240 |
| cctgcggtgc | cgggtccggt | ggcactagac | gagactgtgt | tcgggaagg | caaatccgtt | 300 |
| atgcaggcca | tggtctccgc | ccgtcaagga | gggcaggtgg | tggcggttat | gttggccagc | 360 |
| tttggggcca | gtcgccaatc | cagtgtagtg | gtagaagggc | catcggcccc | agtgatgaaa | 420 |
| tctccagagc | agagtatttc | ggtaccgttt | atcaaaggat | tgacgccgga | ttttttttcc | 480 |
| catttttaata | tccattacgc | agaaggcatg | ccgccgttca | gtggcagttc | tgagcccgat | 540 |
| tacggtggtt | acatggggtt | tactgtgccg | ccggaaacca | tgagcaccgc | agcgctgatt | 600 |
| gcattggtgg | atacctgggc | gccttcagtt | ttacctctgc | tcaaagggcc | agcacccgcc | 660 |
| agttccttga | cctggaccat | ggagctcttg | gatgacccta | gtgtccactc | gccggagact | 720 |
| ttatggcaat | atcgggtaaa | cacggaccaa | tgcagtgatg | gctatggtca | aagtcaggcg | 780 |
| gtggtttggg | atgctgcggg | taaggctgtg | gcgttgagtc | gacaaacctt | tacggtattt | 840 |
| gcatgaaatc | ggaactggtg | ccactcacgg | cgcggacttt | aggtaagcaa | gtgcctcgtc | 900 |
| gtgggcactg | gctgttggcg | gcgctagggc | ggctgatttt | gactgttatg | gggtggcgta | 960 |
| ttgttggtga | tttgcccgat | acgctcgggc | cagttttggc | ggtggcgcca | cacacgtcga | 1020 |
| acatagacgg | ggtcattggt | atcagtgcta | ttcagtcttt | gcgcttggat | gtgcgcttca | 1080 |
| tgggtaagca | cacgttgttt | aaaggtcgtc | ttgggcggtt | catgtactgg | ctgggcggca | 1140 |
| tccctgtgaa | tcgagaaagt | gccagggatg | tggtggacca | gacgacgtcg | gtgatggggg | 1200 |
| aaacaccatt | ttggcttggg | ctaacgccgg | aggggacgcg | taaggcgcc | aagcgttgga | 1260 |
| aaaccgggtt | ttaccgtatt | gctgagcaaa | tgcaggtgcc | gattgtcgtg | ttaggttttct | 1320 |
| gttaccggcg | ccggcaggtc | cggattgtag | attgctttct | gccgacgggc | gatattgatg | 1380 |
| ctgatatggc | gcgaatgacc | gcgtcgttgg | cggatattgt | tccgcgcaaa | cctgcgcagt | 1440 |
| tatccgcccc | gctgaaagcg | gaaaaagctg | ctcgcggcat | tgattgattc | agacgttggc | 1500 |
| agttttgccg | gactgatcaa | ggagatgctg | gcggtgctgg | gcggat | 1546 |

<210> SEQ ID NO 2
<211> LENGTH: 786
<212> TYPE: DNA
<213> ORGANISM: Alcanivorax borkumensis
<220> FEATURE:
<223> OTHER INFORMATION: Nucleotide sequence of tesB-like acyl-CoA
thioesterase from Alcanivorax borkumensis (Abo_1044) (fig. 12)
<220> FEATURE:
<221> NAME/KEY: misc_feature
<222> LOCATION: (1)..(3)
<223> OTHER INFORMATION: Start codon
<220> FEATURE:
<221> NAME/KEY: misc_feature
<222> LOCATION: (785)..(787)
<223> OTHER INFORMATION: Stop codon

<400> SEQUENCE: 2

```
atgacattcg atgagattct agccacgatt gatggccagg gtaacgccac gtttccagaa      60
gggtggggc agggccggac cttatttggt ggcctggtgg gggcggtgct gtttgaacat     120
ttagaaaaaa ccgtggctcg cgggaggttt ctacgtagtt tttctctctc ttttgtcgcc     180
cctgcggtgc cgggtccggt ggcactagac gagactgtgt tcgggaagg caaatccgtt     240
atgcaggcca tggtctccgc ccgtcaagga gggcaggtgg tggcggttat gttggccagc     300
tttggggcca gtcgccaatc cagtgtagtg gtagaagggc atcggcccc agtgatgaaa     360
tctccagagc agagtatttc ggtaccgttt atcaaaggat tgacgccgga tttttttcc     420
cattttaata tccattacgc agaaggcatg ccgccgttca gtggcagttc tgagcccgat     480
tacggtggtt acatgggtt tactgtgccg ccggaaacca tgagcaccgc agcgctgatt     540
gcattggtgg ataccctggc gccttcagtt ttacctctgc tcaaagggcc agcacccgcc     600
agttccttga cctggaccat ggagctcttg gatgaccta gtgtccactc gccggagact     660
ttatggcaat atcgggtaaa cacgaccaa tgcagtgatg ctatggtca aagtcaggcg     720
gtggtttggg atgctgcggg taaggctgtg gcgttgagtc gacaaacctt acggtatttt     780
gcatga                                                                 786
```

<210> SEQ ID NO 3
<211> LENGTH: 261
<212> TYPE: PRT
<213> ORGANISM: Alcanivorax borkumensis
<220> FEATURE:
<223> OTHER INFORMATION: Amino acid sequence of tesB-like acyl-CoA
thioesterase (figure 13)

<400> SEQUENCE: 3

```
Met Thr Phe Asp Glu Ile Leu Ala Thr Ile Asp Gly Gln Gly Asn Ala
1               5                   10                  15

Thr Phe Pro Glu Gly Trp Gly Gln Gly Arg Thr Leu Phe Gly Gly Leu
            20                  25                  30

Val Gly Ala Val Leu Phe Glu His Leu Glu Lys Thr Val Ala Arg Gly
        35                  40                  45

Arg Phe Leu Arg Ser Phe Ser Leu Ser Phe Val Ala Pro Ala Val Pro
    50                  55                  60

Gly Pro Val Ala Leu Asp Glu Thr Val Phe Arg Glu Gly Lys Ser Val
65                  70                  75                  80

Met Gln Ala Met Val Ser Ala Arg Gln Gly Gly Gln Val Val Ala Val
                85                  90                  95

Met Leu Ala Ser Phe Gly Ala Ser Arg Gln Ser Ser Val Val Val Glu
            100                 105                 110

Gly Pro Ser Ala Pro Val Met Lys Ser Pro Glu Gln Ser Ile Ser Val
        115                 120                 125
```

```
Pro Phe Ile Lys Gly Leu Thr Pro Asp Phe Phe Ser His Phe Asn Ile
    130                 135                 140

His Tyr Ala Glu Gly Met Pro Pro Phe Ser Gly Ser Ser Glu Pro Asp
145                 150                 155                 160

Tyr Gly Gly Tyr Met Gly Phe Thr Val Pro Pro Glu Thr Met Ser Thr
                165                 170                 175

Ala Ala Leu Ile Ala Leu Val Asp Thr Trp Ala Pro Ser Val Leu Pro
            180                 185                 190

Leu Leu Lys Gly Pro Ala Pro Ala Ser Ser Leu Thr Trp Thr Met Glu
        195                 200                 205

Leu Leu Asp Asp Pro Ser Val His Ser Pro Glu Thr Leu Trp Gln Tyr
    210                 215                 220

Arg Val Asn Thr Asp Gln Cys Ser Asp Gly Tyr Gly Gln Ser Gln Ala
225                 230                 235                 240

Val Val Trp Asp Ala Ala Gly Lys Ala Val Ala Leu Ser Arg Gln Thr
                245                 250                 255

Phe Thr Val Phe Ala
            260
```

```
<210> SEQ ID NO 4
<211> LENGTH: 2356
<212> TYPE: DNA
<213> ORGANISM: Artificial Sequence
<220> FEATURE:
<223> OTHER INFORMATION: Nucleic acid sequence of miniTn5 Km element,
      coding repeats functional in transposition and
      neomycin phosphotransferase (figure 14)
<220> FEATURE:
<221> NAME/KEY: misc_feature
<222> LOCATION: (1)..(19)
<223> OTHER INFORMATION: Tn5 I end, functional in transposition
<220> FEATURE:
<221> NAME/KEY: misc_feature
<222> LOCATION: (2338)..(2356)
<223> OTHER INFORMATION: Tn5 O end, functional in transposition

<400> SEQUENCE: 4
ctgtctcttg atcagatctg gccacctagg ccgaattccc ggggatccgg tgattgattg      60
agcaagcttt atgcttgtaa accgttttgt gaaaaaattt ttaaaataaa aaggggacc     120 tctagggtcc ccaattaatt agtaatataa tctattaaag gtcattcaaa aggtcatcca    180
ccggatcacc ttaccaagcc ctcgctagat tgttaatgcg gatgttgcga ttacttcgcc    240
caactattgc gataacaaga aaagcgcctt tcatgatata tctcccaatt ttgtgtaggg    300
cttattatgc acgcttaaaa ataataaaag cgacttgacc tgatagtttg gctgtgagca    360
attatgtgct tagtgcatct aacgcttgag ttaaccgcgc cgcgaagcgg cgtcggcttg    420
aacgaattgt tagacattat ttgccgacta ccttggtgat tcgcctttca cgtagtggac    480
aaaatcaacc aactgatctg cgcgagcttc acgctgccgc aagcatcagg cgcaagggc    540 tgctaaagga agcggaacac gtagaaagcc agtccgcaga acggtgctaa ccccggatga    600
atgtcagcta ctgggctatc tggacaaggg aaaacgcaag cgcaaagaga agaggtagc    660 ttgcagtggg cttacatgac gatagctaga ctgggcggtt ttatggacag caagcgaacc    720
ggaattgcca gctggggcgc cctctggtaa ggttgggaag ccctgcaaag taaactggat    780
ggctttcttg ccgccaagga tctgatgcg caggggatca agatctgatc aagagacagg    840
atgaggatcg tttcgcatga ttgaacaaga tggattgcac gcaggttctc cggccgcttg    900
ggtggagagg ctattcggct atgactggc acaacagaca atcggctgct ctgatgccgc    960
cgtgttccgg ctgtcagcgc aggggcgccc ggttctttt gtcaagaccg acctgtccgg   1020
```

```
tgccctgaat gaactgcagg acgaggcagc gcggctatcg tggctggcca cgacgggcgt    1080
tccttgcgca gctgtgctcg acgttgtcac tgaagcggga agggactggc tgctattggg    1140
cgaagtgccg gggcaggatc tcctgtcatc tcaccttgct cctgccgaga agtatccat    1200 catggctgat gcaatgcggc ggctgcatac gcttgatccg gctacctgcc cattcgacca    1260
ccaagcgaaa catcgcatcg agcgagcacg tactcggatg aagccggtc ttgtcgatca     1320 ggatgatctg gacgaagagc atcaggggct cgcgccagcc gaactgttcg ccaggctcaa    1380
ggcgcgcatg cccgacggcg aggatctcgt cgtgacccat ggcgatgcct gcttgccgaa    1440
tatcatggtg aaaatggcc gcttttctgg attcatcgac tgtggccggc tgggtgtggc     1500
ggaccgctat caggacatag cgttggctac ccgtgatatt gctgaagagc ttggcggcga    1560 tgggctgac cgcttcctcg tgctttacgg tatcgccgct cccgattcgc agcgcatcgc     1620
cttctatcgc cttcttgacg agttcttctg agcgggactc tggggttcga atgaccgac     1680 caagcgacgc ccaacctgcc atcacgagat ttcgattcca ccgccgcctt ctatgaaagg    1740
ttgggcttcg gaatcgtttt ccgggacgcc ggctggatga tcctccagcg cggggatctc    1800
atgctggagt tcttcgccca ccccgggctc gatcccctcg cgagttggtt cagctgctgc    1860
ctgaggctgg acgacctcgc ggagttctac cggcagtgca aatccgtcgg catccaggaa    1920
accagcagcg gctatccgcg catccatgcc cccgaactgc aggagtgggg aggcacgatg    1980
gccgctttgg tcgacccgga cgggacggat cagtgagggt ttgcaactgt gggtcaagga    2040
tctggatttc gatcacggca cgatcatcgt cgggagggca agggctccaa ggatcgggcc    2100
ttgatgttac cgagagcttg gtacccagtc tgtgtgagca ggggaattga tccggtggat    2160
gaccttttga atgaccttta atagattata ttactaatta attggggacc ctagaggtcc    2220 cctttttat tttaaaaatt ttttcacaaa acggtttaca agcataaagc ttgctcaatc     2280
aatcaccgga tccccgggaa ttcgtcgaca agctgcggcc gcctaggccg tggccgaact    2340
tgtgtataag agtcag                                                     2356

<210> SEQ ID NO 5
<211> LENGTH: 264
<212> TYPE: PRT
<213> ORGANISM: Artificial Sequence
<220> FEATURE:
<223> OTHER INFORMATION: Amino acid sequence of neomycin
      phosphotransferase responsible for neomycin and kanamycin
      resistance (figure 15)

<400> SEQUENCE: 5

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110
```

```
Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 6
<211> LENGTH: 645
<212> TYPE: DNA
<213> ORGANISM: Alcanivorax borkumensis
<220> FEATURE:
<223> OTHER INFORMATION: Nucleotide sequence of putative acyltransfrase
      plsC (Abo_1045) (figure 16)
<220> FEATURE:
<221> NAME/KEY: misc_feature
<222> LOCATION: (1)..(3)
<223> OTHER INFORMATION: Start codon
<220> FEATURE:
<221> NAME/KEY: misc_feature
<222> LOCATION: (643)..(645)
<223> OTHER INFORMATION: Stop codon

<400> SEQUENCE: 6
atgaaatcgg aactggtgcc actcacggcg cggactttag gtaagcaagt gcctcgtcgt      60
gggcactggc tgttggcggc gctagggcgg ctgattttga ctgttatggg gtggcgtatt     120
gttggtgatt tgcccgatac gcctcgggca gttttggcgg tggcgccaca cacgtcgaac     180
atagacgggg tcattggtat cagtgctatt cagtctttgc gcttggatgt gcgcttcatg     240
ggtaagcaca cgttgtttaa aggtcgtctt gggcggttca tgtactggct gggcggcatc     300
cctgtgaatc gagaaagtgc cagggatgtg gtggaccaga cgacgtcggt gatgggggaa     360
acaccatttt ggcttgggct aacgccggag gggacgcgta aggcgccaa gcgttggaaa     420 accgggtttt accgtattgc tgagcaaatg caggtgccga ttgtcgtgtt aggtttctgt     480
taccggcgcc ggcaggtccg gattgtagat tgctttctgc cgacgggcga tattgatgct     540
gatatggcgc gaatgaccgc gtcgttggcg gatattgttc cgcgcaaacc tgcgcagtta     600
tccgccccgc tgaaagcgga aaaagctgct cgcggcattg attga                    645

<210> SEQ ID NO 7
<211> LENGTH: 214
<212> TYPE: PRT
<213> ORGANISM: Alcanivorax borkumensis
<220> FEATURE:
<223> OTHER INFORMATION: Amino acid sequence of putative acyltransferase
      plsC (figure 17)
```

<400> SEQUENCE: 7

| | | | | | | | | | | | | | | |
|---|---|---|---|---|---|---|---|---|---|---|---|---|---|---|
|Met|Lys|Ser|Glu|Leu|Val|Pro|Leu|Thr|Ala|Arg|Thr|Leu|Gly|Lys|Gln|
|1| | | |5| | | | |10| | | | |15|

Val Pro Arg Arg Gly His Trp Leu Leu Ala Ala Leu Gly Arg Leu Ile
20 25 30

Leu Thr Val Met Gly Trp Arg Ile Val Gly Asp Leu Pro Asp Thr Pro
35 40 45

Arg Ala Val Leu Ala Val Ala Pro His Thr Ser Asn Ile Asp Gly Val
50 55 60

Ile Gly Ile Ser Ala Ile Gln Ser Leu Arg Leu Asp Val Arg Phe Met
65 70 75 80

Gly Lys His Thr Leu Phe Lys Gly Arg Leu Gly Arg Phe Met Tyr Trp
85 90 95

Leu Gly Gly Ile Pro Val Asn Arg Glu Ser Ala Arg Asp Val Val Asp
100 105 110

Gln Thr Thr Ser Val Met Gly Glu Thr Pro Phe Trp Leu Gly Leu Thr
115 120 125

Pro Glu Gly Thr Arg Lys Gly Ala Lys Arg Trp Lys Thr Gly Phe Tyr
130 135 140

Arg Ile Ala Glu Gln Met Gln Val Pro Ile Val Val Leu Gly Phe Cys
145 150 155 160

Tyr Arg Arg Arg Gln Val Arg Ile Val Asp Cys Phe Leu Pro Thr Gly
165 170 175

Asp Ile Asp Ala Asp Met Ala Arg Met Thr Ala Ser Leu Ala Asp Ile
180 185 190

Val Pro Arg Lys Pro Ala Gln Leu Ser Ala Pro Leu Lys Ala Glu Lys
195 200 205

Ala Ala Arg Gly Ile Asp
210

<210> SEQ ID NO 8
<211> LENGTH: 798
<212> TYPE: DNA
<213> ORGANISM: Pseudomonas putida KT2440
<220> FEATURE:
<223> OTHER INFORMATION: Nucleotide sequence of putative acyl-CoA
      thioesterase II (GeneID:1045294) (figure 18)

<400> SEQUENCE: 8

| | | |
|---|---|---|
|atgactttca accaactgct cgacgccgtg cgggccaacc cggattccgt cagcattccg|  |60|
|cccagctggg cccaggggcg cgctgccttt ggcgggctga tggcggccat ggtctatgaa|  |120|
|accatgcgcc tcaagatcag cgacaaccgc ccggtacgct cattggccat cagcttcgtg|  |180|
|gcacccgcgg cggcggatgt gcccatccgc ttcgaggtgg aggttttgcg cgaaggcaag|  |240|
|gcggttagca cgttgctggg ccgcgctgtt caggatggcc aggtggtgac tttggtgcag|  |300|
|ggcaatttcg gtgcgggccg cccttcggtg gtcgaagtgc cggcgttgcc ggccatcgaa|  |360|
|atgcctgcgc tcgatgaggc gggccccgag ttgcccctata tcaaaggcgt taccccctgag|  |420|
|ttcatgcggc acgtggccct cgcgctgggca gtaggtgggc tgccgttcag tggcaatcag|  |480|
|tcgcgcaaga tgggcggctg ggtgcgcttg cgggatgtgg tggaagaaca ggtgaacgag|  |540|
|gcgcacctgt tggcgttggt cgatgcctgg ccgcccagcc tcatgccgtt tctcaagcag|  |600|
|cccgctgcgg gcagtacgtt gacctggacc atcgagttca tccagccaac ggcgaagctg|  |660|
|tcgaccctgg attggtgccg gtactgtgtg agacccgagc atgcgcggga tggctatggg|  |720|

| catgctgctg cggcgttgtg gacggcgcag ggcgagttgt tggcgttgag ccggcagacc | 780 |
| gtcaccgttt tcgcctga | 798 |

<210> SEQ ID NO 9
<211> LENGTH: 798
<212> TYPE: DNA
<213> ORGANISM: Pseudomonas aeruginosa PA01
<220> FEATURE:
<223> OTHER INFORMATION: Nucleotide sequence of hypothetical protein
    PA2871 (GeneID:882599) (figure 19)

<400> SEQUENCE: 9

| atgaatttt ccgaattgat ccaggcggtc cgccgcgacc cttcctcggt ggtagtaccg | 60 |
| gccagtgggg gccagggccg cgccaccttc ggtggcgtgg tggtggcgtt ggcctacgag | 120 |
| gccatgcttg cggtggtcga ggcggggcgt ccgttgcgct ccatcggcgt cagcttcgtc | 180 |
| ggaccgctgg cccccgagca gccggcgagc ttcagcgccc ggttgttgcg cgagggcaag | 240 |
| gcggtgagcc aggtccaggt cgaggtccgt cagggcgagc aggtggtgac gctggtccag | 300 |
| gccagtttcg gcgtcgcccg cgcatcggcg gtggcggtgg aagcgttgcc ggcggccggg | 360 |
| atgaagggcc ccgaagagag ccaggagctg ccctatatcc gtaacgtgac cccggagttc | 420 |
| actcgctaca tcgccatgcg ctgggcagtg gcggcctgc cgttctcttc gaacaagtcg | 480 |
| cgccagatgg gcggctggat gcgtttccgc gacgaacccg agggagagcc catggaggtt | 540 |
| tcccacctgc tggcgctgct cgactcctgg ccgccggcgc tgttgccgca cctgggcacc | 600 |
| ccggcgatgg ccagctcgct gacctggacc gccgagttcc tccagccgct gccgcagcaa | 660 |
| ggcagcggcg actggtgccg ttacctggcg gagatcgagg aggcgcgtga cggctacggc | 720 |
| cacgtggcgg cgcggatgtg gagcgccgac ggccagttgc tggcgatcag ccggcagatg | 780 |
| gtcacggtgt tcggctga | 798 |

<210> SEQ ID NO 10
<211> LENGTH: 798
<212> TYPE: DNA
<213> ORGANISM: Pseudomonas syringae pv B728a
<220> FEATURE:
<223> OTHER INFORMATION: Nucleotide sequence of acyl-CoA thioesterase
    II, putative of p. syringae pv B728a (GeneID:3367571) (figure 20)

<400> SEQUENCE: 10

| atgacctttt ctgaactgat cgatgcgctg cgtcgcgatc cgcgctctgt cacgatccct | 60 |
| gccgaatggt ctcaagggcg tgcctgcttc ggcgggctga tggctgcgct gacctacgaa | 120 |
| gcgatgcgtg cacaggtgcc ggaagggcgg ccggttcgtt cgttggcgat caccttttgtc | 180 |
| gggccggccg cgcccggtgt gccgattgct ttcgaggtcg acaccctgcg ccatggcaag | 240 |
| gcagtcagtc aggtgctggg acgcgccatg cagaacggtc aggtcatgac cctgatacaa | 300 |
| ggcagcttcg gtgccctcg ggaatcgatg atcaccgttg ccgcagaggc cgcgccggtc | 360 |
| cttaaaccgg ttgatcaatg tccggagctg ccgttcgcca gcggcgtgat gcctgattac | 420 |
| ctgcgcttca tggacatccg ctgggcgttg gcggcatgc cattcagtaa tacccgatca | 480 |
| ccggcgattg gcggctacgt gcgctttcgc gatacgccgc acgccacgcc catgagcgaa | 540 |
| gcgcacattc tggcgctggt ggacacctgg ccgcctgcgg tactgccgca cctggacaaa | 600 |
| ccggcccccg gcagctcact gacctggacc attgagttcg tccagcccca gccgtcgctc | 660 |
| gatacccctgc agtggtgcag ctaccgcgca gtcatcgagc atgcccgcga tggctatggc | 720 |

```
cataccgccg cggcattgtg gagccccgac ggcgagctga tcgcaatcag ccgccagacg    780
gttaccgtat ttggctga                                                 798
```

<210> SEQ ID NO 11
<211> LENGTH: 795
<212> TYPE: DNA
<213> ORGANISM: Pseudomonas fluorescens PfO-1
<220> FEATURE:
<223> OTHER INFORMATION: Nucleotide sequence of acyl-CoA thioesterase
      (locus_tag=Pflu02003109) (figure 21)

<400> SEQUENCE: 11

```
atgcgctttt gcgatctgat cgatgctgtc cgtcgtcaac cggaggtcac gattccggcg    60
gagtggggcc agggccgggc cagttttggc gggctggtgg ccgcgctgca atttgaagtg   120
atgcgcacca aggttccgac cgatcggccg gtacgttcgc tggcgatcac cttcgtcggc   180
ccggtcgagc ccgaagtgcc ggtgagtttt gaagtcgagg tactacgcga aggcaaagcg   240
gtcagccagg tgctggggcg tgctgtgcag aacggtcagg tggtgacgat ggtgcaaggc   300
agcttcgggg cttcgcggcc atcggaagtg gcggttgaag cctatcccgc gccggaaatg   360
aagcactggg acgattgcca ggaactgccg tacatcaaag gcgtaacccc cgagttcatg   420
cgtcatctgg cgatgcgctg gagcgttggc gggatgccgt tcaccggcaa tcaatcgcgg   480
ctgatgggtg gctgggtgcg cctgcgtggg gatgtgaagg aagagtcggt caacgaagcg   540
cacctgctgg cgctggtcga tgcctggcca ccagcgctgt tgccgtacct gaagaaaccg   600
gcaccgggca gtacgctgac ctggaccatc gaattcgttc agccgttacg cgatttgagt   660
acgctggatt tttgccaata cctggcggac atcgagtatg ccgccgacgg ttacggccac   720
gtcgccgcca agctgtggag tgcgaagggt gaactgattg ccatgagtcg gcagacggtg   780
acgatcttcg cctga                                                   795
```

<210> SEQ ID NO 12
<211> LENGTH: 795
<212> TYPE: DNA
<213> ORGANISM: Idiomarina loihiensis L2TR
<220> FEATURE:
<223> OTHER INFORMATION: Nucleotide sequence of tesB-like acyl-CoA
      thioesterase (locus_tag="IL0656") (figure 22)

<400> SEQUENCE: 12

```
atgaacttcc acacagctgt agaacaaatc gttgcggata gaacaatca agtcattgaa    60 ctaccttccg gctgggctca gggacgcgcg tttttcggcg gattcagcgg agcattggct   120
gctcagtttt tgttgaaaca atttccgatt gaatatcatc ttcgttccat gagtatctct   180
tttgtcgcgc ctgctgaacc gggtgaggct gagttaaatt accgaatttt gcgcgaggga   240
aaatcggtta ttcaggttgc tgtcgaactg cagcagcaag gcagattat gttgtcttgt   300 ctggcgagcc tgggcaaagg ccgaagttca acggttacag tggtaagtga acgccacccc   360
gatcttaaaa ccatcaacga cggaccaggt ttacctgaag cggatattgt cccagagttt   420
gcgaaaaact tcgattaccg tattacgtca ggtggtatgc catttagcgg acaaccggga   480
agaacttttg gtggctggat acgttttcgt gaagaacaac agccgctgac aacggcaact   540
atactggctt tagttgacgc ctgccaccg gcagtcttgc ctcatctgga cagccctgcg   600
ccggcctcgt ctttaacctg gactattgag tttcccgata ttcctctaca aagtttcagt   660
agccacgact ggtttcagta cgaagctttt attgagcatg ctgaaaatgg ttatgggcac   720
```

```
agccgcgcgg gtctgtggag tgagaagggc gagttattag ctataagtcg acagactttt    780
acggtatttg cgtaa                                                    795
```

<210> SEQ ID NO 13
<211> LENGTH: 804
<212> TYPE: DNA
<213> ORGANISM: Acinetobacter sp. ADP1
<220> FEATURE:
<223> OTHER INFORMATION: Nucleotide sequence of putative acyl-CoA
      thioesterase II (locus_tag="ACIAD0341) (figure 23)

<400> SEQUENCE: 13

```
atgagtgatg ctatgccttt agatcagaca ttggaacaac tgacgcaaga tgaatggatt     60
gatattcccc aaggctggtc gcagggaaga acgatttatg gtggattggt tgcaggcttg    120
ctcatgcata aagcattaag tgtgatgaat gatgagtcca aaaatctgtt aagtaccagc    180
attacttttg tgggaccagt gaatgaaggg cgggtacgac taacagttga atcttgcgg     240 cagggtaaat ctgtcaccac aattgaggca cgtttatggc aggaccaggc tgttcaaacc    300
atcttgatcg caagtttcgg acagccgcgt tcttctgaaa ttttgtgct taacttaccc     360 gaggcaccag actatttgtc tcccgagcag ttctcaagaa tgccttttgt aaaaatgatg    420
ccagaatgct atcaacaatt cgatctgcga tgggcagaag gtcattatcc catgactcaa    480
caagctccag attttggtgg ctggtgccgt tacgatatcc aaaaacattc accgcgagca    540
ttgaatgtgg ctgatttgtt aattttgatg gatatctggc caccaggggt actgcccatg    600 tttcaaaacca tcgcacctgc cagttctcta acatggcatc tcacttttgt tcgtcccgtt    660
gcttatgagt tacatgattg gtttaagtat caggtcgtca cgcagcatgc tgcctttggc    720
tatgctacag aatatgcgca tttatgggat gctcaaaacc gtctgattgc tatttcgagg    780
cagacagtta ctgttttttgc ctag                                          804
```

<210> SEQ ID NO 14
<211> LENGTH: 789
<212> TYPE: DNA
<213> ORGANISM: Caulobacter crescentus CB15
<220> FEATURE:
<223> OTHER INFORMATION: Nucleotide sequence of hypothetical protein
      CC2472 (GeneID:943632) (figure 24)

<400> SEQUENCE: 14

```
atgacgctct acaccgacct cgtcgcggcc atcgcctcga ccgaaactgg cttttccgcc     60
catgtctccg acgactggaa gcaaggccgc accacctatg cggcttgag cggcgccttg    120 tgcgtcgagg ccgccctgcg agcctttccc gaggcccctc ctctgcgctc ggcgcaattc    180
gcctttgtcg gcccggcggc cggcgagttg gcgatctcgg tgcggccgct gcggcagggc    240
aagtcgacgc ttttcgtcgc cgtcgatctg atcggcgaac agggcgtggc cacccacggc    300
gtgctgacct tcgcgcgcgg cgcggacctca gccatctcgt acgaagaagt cctctgcccg    360
cccgtggcgc cggccggcgc ctgtgagctg ttcttccccg aaaatcgcca gggcgcgccg    420
cacttctcgg cgcagttcga ggtgcgcaag gccgcggca cgcgccccct ggccgggggt    480
gagccggaat atctgctgtg gatccgccac cgcgatccgg ccgcgacctc gatctcggcc    540
ctggtcgcgt tggccgacat gccgccgccc ccggccatgg cgctgttccc gcagtttggg    600
ccgatctcga ccatgacctg gtcgctggat atcgtgggcc tgcccgaggc ggacgacgac    660
ggctggcggc tgctgcgcac ccgggccgag accatcggcg acggctactc gacccaggag    720
```

-continued

```
atgcatctgt gggacgccaa gggccgcccg ctggtcctgg cgcgacagaa cgtggcgatc    780
ttcgtctga                                                            789
```

<210> SEQ ID NO 15
<211> LENGTH: 777
<212> TYPE: DNA
<213> ORGANISM: Erythrobacter litoralis HTCC2594
<220> FEATURE:
<223> OTHER INFORMATION: Nucleotide sequence of hypothetical protein
    ELI0992 (locus_tag=ELI0992) (figure 25)

<400> SEQUENCE: 15

```
atgtccgttt ccgatcttcg tgcgccgatc acgtccgaag gtggcgctgt cactcttcca     60
gccgacaaat ggctgcaggg ccgcacgctc tttggcggag cctcggcgct tgtcgcctac    120
accgccgcgg tgcgcgcttt ccccgatctc ccgcccttgc gcgcagcgca gatcggattt    180
gtcgcgccgg tcggaaagga cgtggagacg cgggccgcaa tggtccgaca gggtcgcaac    240
gtcgcgcagg tgcgcagcga actgctggtc gaaggcaagg tcgcgctcac cgcattctgg    300
ctgttcggaa ccggtcgcga ggccaacgcc gtacatgccg ctgccaaggc cgatccctgg    360
cccggcgcac cggaagagaa cgattccgcg atgaccgaca agggcccgcc tttcatcgtc    420
aacaatttcg acattcgccg cgcgcaggaa cgcaaggcc ccggcgaacc gatcgtccgg     480
cgctggttca ggctgaccga tcggggcgag ctcgatcgcg tatcggagct gatcctggtg    540
ggcgatacgc tgcccccggg cgccatgcgc gcgatgcagc gccagggccc gatcagctcg    600
atcaactggt cgttcaatat tctcgatgcg gaactcggca cgcgcgacgg ctggtggctc    660
ggcgagaccg ccagccagca tgccggtgca ggctattcga gcgagcggct acggctctgg    720
aatgccgacg gcgtgcaggt gatggacgga ttgcaatccg ttgccgtctt cggctga      777
```

<210> SEQ ID NO 16
<211> LENGTH: 265
<212> TYPE: PRT
<213> ORGANISM: Pseudomonas putida KT2440
<220> FEATURE:
<223> OTHER INFORMATION: Amino acid sequence of putative acyl-CoA
    thioesterase II (protein_id="NP_744457.1") (figure
    26)

<400> SEQUENCE: 16

```
Met Thr Phe Asn Gln Leu Leu Asp Ala Val Arg Ala Asn Pro Asp Ser
1               5                   10                  15

Val Ser Ile Pro Pro Ser Trp Ala Gln Gly Arg Ala Ala Phe Gly Gly
            20                  25                  30

Leu Met Ala Ala Met Val Tyr Glu Thr Met Arg Leu Lys Ile Ser Asp
        35                  40                  45

Asn Arg Pro Val Arg Ser Leu Ala Ile Ser Phe Val Ala Pro Ala Ala
    50                  55                  60

Ala Asp Val Pro Ile Arg Phe Glu Val Glu Val Leu Arg Glu Gly Lys
65                  70                  75                  80

Ala Val Ser Thr Leu Leu Gly Arg Ala Val Gln Asp Gly Gln Val Val
                85                  90                  95

Thr Leu Val Gln Gly Asn Phe Gly Ala Gly Arg Pro Ser Val Val Glu
            100                 105                 110

Val Pro Ala Leu Pro Ala Ile Glu Met Pro Ala Leu Asp Glu Ala Ala
        115                 120                 125

Pro Glu Leu Pro Tyr Ile Lys Gly Val Thr Pro Glu Phe Met Arg His
    130                 135                 140
```

```
Val Ala Leu Arg Trp Ala Val Gly Gly Leu Pro Phe Ser Gly Asn Gln
145                 150                 155                 160

Ser Arg Lys Met Gly Gly Trp Val Arg Leu Arg Asp Val Val Glu Glu
                165                 170                 175

Gln Val Asn Glu Ala His Leu Leu Ala Leu Val Asp Ala Trp Pro Pro
            180                 185                 190

Ser Leu Met Pro Phe Leu Lys Gln Pro Ala Ala Gly Ser Thr Leu Thr
        195                 200                 205

Trp Thr Ile Glu Phe Ile Gln Pro Thr Ala Lys Leu Ser Thr Leu Asp
    210                 215                 220

Trp Cys Arg Tyr Cys Val Glu Thr Glu His Ala Arg Asp Gly Tyr Gly
225                 230                 235                 240

His Ala Ala Ala Leu Trp Thr Ala Gln Gly Glu Leu Leu Ala Leu
                245                 250                 255

Ser Arg Gln Thr Val Thr Val Phe Ala
                260                 265

<210> SEQ ID NO 17
<211> LENGTH: 265
<212> TYPE: PRT
<213> ORGANISM: Pseudomonas aeruginosa PA01
<220> FEATURE:
<223> OTHER INFORMATION: Amino acid sequence of hypothetical protein
      PA2871 (protein_id="NP_251561.1") (figure 27)

<400> SEQUENCE: 17

Met Asn Phe Ser Glu Leu Ile Gln Ala Val Arg Arg Asp Pro Ser Ser
1               5                   10                  15

Val Val Val Pro Ala Ser Trp Gly Gln Gly Arg Ala Thr Phe Gly Gly
                20                  25                  30

Leu Val Val Ala Leu Ala Tyr Glu Ala Met Leu Ala Val Val Glu Ala
            35                  40                  45

Gly Arg Pro Leu Arg Ser Ile Gly Val Ser Phe Val Gly Pro Leu Ala
        50                  55                  60

Pro Glu Gln Pro Ala Ser Phe Ser Ala Arg Leu Leu Arg Glu Gly Lys
65                  70                  75                  80

Ala Val Ser Gln Val Gln Val Glu Val Arg Gln Gly Glu Gln Val Val
                85                  90                  95

Thr Leu Val Gln Ala Ser Phe Gly Val Ala Arg Ala Ser Ala Val Ala
            100                 105                 110

Val Glu Ala Leu Pro Ala Ala Gly Met Lys Gly Pro Glu Glu Ser Gln
        115                 120                 125

Glu Leu Pro Tyr Ile Arg Asn Val Thr Pro Glu Phe Thr Arg Tyr Ile
    130                 135                 140

Ala Met Arg Trp Ala Val Gly Gly Leu Pro Phe Ser Ser Asn Lys Ser
145                 150                 155                 160

Arg Gln Met Gly Gly Trp Met Arg Phe Arg Asp Glu Pro Glu Gly Glu
                165                 170                 175

Pro Met Glu Val Ser His Leu Leu Ala Leu Leu Asp Ser Trp Pro Pro
            180                 185                 190

Ala Leu Leu Pro His Leu Gly Thr Pro Ala Met Ala Ser Ser Leu Thr
        195                 200                 205

Trp Thr Ala Glu Phe Leu Gln Pro Leu Pro Gln Gln Gly Ser Gly Asp
    210                 215                 220

Trp Cys Arg Tyr Leu Ala Glu Ile Glu Glu Ala Arg Asp Gly Tyr Gly
225                 230                 235                 240
```

```
His Val Ala Ala Arg Met Trp Ser Ala Asp Gly Gln Leu Leu Ala Ile
            245                 250                 255

Ser Arg Gln Met Val Thr Val Phe Gly
            260                 265
```

<210> SEQ ID NO 18
<211> LENGTH: 265
<212> TYPE: PRT
<213> ORGANISM: Pseudomonas syringae pv B728a
<220> FEATURE:
<223> OTHER INFORMATION: Amino acid sequence of acyl-CoA thioesterase
      II, putative of p. syringae pv B728a (protein_id="YP_235138.1)
      (figure 28)

<400> SEQUENCE: 18

```
Met Thr Phe Ser Glu Leu Ile Asp Ala Leu Arg Arg Asp Pro Arg Ser
1               5                   10                  15

Val Thr Ile Pro Ala Glu Trp Ser Gln Gly Arg Ala Cys Phe Gly Gly
            20                  25                  30

Leu Met Ala Ala Leu Thr Tyr Glu Ala Met Arg Ala Gln Val Pro Glu
            35                  40                  45

Gly Arg Pro Val Arg Ser Leu Ala Ile Thr Phe Val Gly Pro Ala Ala
50                  55                  60

Pro Gly Val Pro Ile Ala Phe Glu Val Asp Thr Leu Arg His Gly Lys
65                  70                  75                  80

Ala Val Ser Gln Val Leu Gly Arg Ala Met Gln Asn Gly Gln Val Met
            85                  90                  95

Thr Leu Ile Gln Gly Ser Phe Gly Ala Pro Arg Glu Ser Met Ile Thr
            100                 105                 110

Val Ala Ala Glu Ala Ala Pro Val Leu Lys Pro Val Asp Gln Cys Pro
            115                 120                 125

Glu Leu Pro Phe Ala Ser Gly Val Met Pro Asp Tyr Leu Arg Phe Met
            130                 135                 140

Asp Ile Arg Trp Ala Leu Gly Gly Met Pro Phe Ser Asn Thr Arg Ser
145                 150                 155                 160

Pro Ala Ile Gly Gly Tyr Val Arg Phe Arg Asp Thr Pro His Ala Thr
                165                 170                 175

Pro Met Ser Glu Ala His Ile Leu Ala Leu Val Asp Thr Trp Pro Pro
            180                 185                 190

Ala Val Leu Pro His Leu Asp Lys Pro Ala Pro Gly Ser Ser Leu Thr
            195                 200                 205

Trp Thr Ile Glu Phe Val Gln Pro Gln Pro Ser Leu Asp Thr Leu Gln
            210                 215                 220

Trp Cys Ser Tyr Arg Ala Val Ile Glu His Ala Arg Asp Gly Tyr Gly
225                 230                 235                 240

His Thr Ala Ala Ala Leu Trp Ser Pro Asp Gly Glu Leu Ile Ala Ile
                245                 250                 255

Ser Arg Gln Thr Val Thr Val Phe Gly
            260                 265
```

<210> SEQ ID NO 19
<211> LENGTH: 264
<212> TYPE: PRT
<213> ORGANISM: Pseudomonas fluorescens Pf0-1
<220> FEATURE:
<223> OTHER INFORMATION: Amino acid sequence of acyl-CoA thioesterase
      (protein_id="ZP_00264181.1) (figure 29)

<400> SEQUENCE: 19

```
Met Arg Phe Cys Asp Leu Ile Asp Ala Val Arg Arg Gln Pro Glu Val
1               5                   10                  15

Thr Ile Pro Ala Glu Trp Gly Gln Gly Arg Ala Ser Phe Gly Gly Leu
            20                  25                  30

Val Ala Ala Leu Gln Phe Glu Val Met Arg Thr Lys Val Pro Thr Asp
        35                  40                  45

Arg Pro Val Arg Ser Leu Ala Ile Thr Phe Val Gly Pro Val Glu Pro
    50                  55                  60

Glu Val Pro Val Ser Phe Glu Val Glu Val Leu Arg Glu Gly Lys Ala
65                  70                  75                  80

Val Ser Gln Val Leu Gly Arg Ala Val Gln Asn Gly Gln Val Val Thr
                85                  90                  95

Met Val Gln Gly Ser Phe Gly Ala Ser Arg Pro Ser Glu Val Ala Val
            100                 105                 110

Glu Ala Tyr Pro Ala Pro Glu Met Lys His Trp Asp Asp Cys Gln Glu
        115                 120                 125

Leu Pro Tyr Ile Lys Gly Val Thr Pro Glu Phe Met Arg His Leu Ala
    130                 135                 140

Met Arg Trp Ser Val Gly Gly Met Pro Phe Thr Gly Asn Gln Ser Arg
145                 150                 155                 160

Leu Met Gly Gly Trp Val Arg Leu Arg Gly Asp Val Lys Glu Glu Ser
                165                 170                 175

Val Asn Glu Ala His Leu Leu Ala Leu Val Asp Ala Trp Pro Pro Ala
            180                 185                 190

Leu Leu Pro Tyr Leu Lys Lys Pro Ala Pro Gly Ser Thr Leu Thr Trp
        195                 200                 205

Thr Ile Glu Phe Val Gln Pro Leu Arg Asp Leu Ser Thr Leu Asp Phe
    210                 215                 220

Cys Gln Tyr Leu Ala Asp Ile Glu Tyr Ala Ala Asp Gly Tyr Gly His
225                 230                 235                 240

Val Ala Ala Lys Leu Trp Ser Ala Lys Gly Glu Leu Ile Ala Met Ser
                245                 250                 255

Arg Gln Thr Val Thr Ile Phe Ala
            260
```

<210> SEQ ID NO 20
<211> LENGTH: 264
<212> TYPE: PRT
<213> ORGANISM: Idiomarina loihiensis L2TR
<220> FEATURE:
<223> OTHER INFORMATION: Amino acid sequence of tesB-like acyl-CoA thioesterase (protein_id=AAV81497.1) (figure 30)

<400> SEQUENCE: 20

```
Met Asn Phe His Thr Ala Val Glu Gln Ile Val Ala Asp Lys Asn Asn
1               5                   10                  15

Gln Val Ile Glu Leu Pro Ser Gly Trp Ala Gln Gly Arg Ala Phe Phe
            20                  25                  30

Gly Gly Phe Ser Gly Ala Leu Ala Ala Gln Phe Leu Leu Lys Gln Phe
        35                  40                  45

Pro Ile Glu Tyr His Leu Arg Ser Met Ser Ile Ser Phe Val Ala Pro
    50                  55                  60

Ala Glu Pro Gly Glu Ala Glu Leu Asn Tyr Arg Ile Leu Arg Glu Gly
65                  70                  75                  80
```

-continued

```
Lys Ser Val Ile Gln Val Ala Val Glu Leu Gln Gln Gly Gln Ile
                85                  90                  95

Met Leu Ser Cys Leu Ala Ser Leu Gly Lys Gly Arg Ser Thr Val
            100                 105                 110

Thr Val Val Ser Glu Thr Pro Pro Asp Leu Lys Thr Ile Asn Asp Gly
        115                 120                 125

Pro Gly Leu Pro Glu Ala Asp Ile Val Pro Glu Phe Ala Lys Asn Phe
130                 135                 140

Asp Tyr Arg Ile Thr Ser Gly Gly Met Pro Phe Ser Gly Gln Pro Gly
145                 150                 155                 160

Arg Thr Phe Gly Gly Trp Ile Arg Phe Arg Glu Glu Gln Pro Leu
            165                 170                 175

Thr Thr Ala Thr Ile Leu Ala Leu Val Asp Ala Trp Pro Pro Ala Val
            180                 185                 190

Leu Pro His Leu Asp Ser Pro Ala Pro Ala Ser Ser Leu Thr Trp Thr
            195                 200                 205

Ile Glu Phe Pro Asp Ile Pro Leu Gln Ser Phe Ser Ser His Asp Trp
210                 215                 220

Phe Gln Tyr Glu Ala Phe Ile Glu His Ala Glu Asn Gly Tyr Gly His
225                 230                 235                 240

Ser Arg Ala Gly Leu Trp Ser Glu Lys Gly Glu Leu Leu Ala Ile Ser
            245                 250                 255

Arg Gln Thr Phe Thr Val Phe Ala
            260

<210> SEQ ID NO 21
<211> LENGTH: 267
<212> TYPE: PRT
<213> ORGANISM: Acinetobacter sp. ADP1
<220> FEATURE:
<223> OTHER INFORMATION: Amino acid sequence of putative acyl-CoA
      thioesterase II (protein_id=CAG67294.1) (figure
      31)

<400> SEQUENCE: 21

Met Ser Asp Ala Met Pro Leu Asp Gln Thr Leu Glu Gln Leu Thr Gln
1               5                   10                  15

Asp Glu Trp Ile Asp Ile Pro Gln Gly Trp Ser Gln Gly Arg Thr Ile
            20                  25                  30

Tyr Gly Gly Leu Val Ala Gly Leu Leu Met His Lys Ala Leu Ser Val
        35                  40                  45

Met Asn Asp Glu Ser Lys Asn Leu Leu Ser Thr Ser Ile Thr Phe Val
50                  55                  60

Gly Pro Val Asn Glu Gly Arg Val Arg Leu Thr Val Glu Ile Leu Arg
65                  70                  75                  80

Gln Gly Lys Ser Val Thr Thr Ile Glu Ala Arg Leu Trp Gln Asp Gln
                85                  90                  95

Ala Val Gln Thr Ile Leu Ile Ala Ser Phe Gly Gln Pro Arg Ser Ser
            100                 105                 110

Glu Ile Phe Val Leu Asn Leu Pro Glu Ala Pro Asp Tyr Leu Ser Pro
        115                 120                 125

Glu Gln Phe Ser Arg Met Pro Phe Val Lys Met Met Pro Glu Cys Tyr
130                 135                 140

Gln Gln Phe Asp Leu Arg Trp Ala Glu Gly His Tyr Pro Met Thr Gln
145                 150                 155                 160

Gln Ala Pro Asp Phe Gly Gly Trp Cys Arg Tyr Asp Ile Gln Lys His
            165                 170                 175
```

```
Ser Pro Arg Ala Leu Asn Val Ala Asp Leu Leu Ile Leu Met Asp Ile
            180                 185                 190

Trp Pro Pro Gly Val Leu Pro Met Phe Gln Thr Ile Ala Pro Ala Ser
        195                 200                 205

Ser Leu Thr Trp His Leu Thr Phe Val Arg Pro Val Ala Tyr Glu Leu
    210                 215                 220

His Asp Trp Phe Lys Tyr Gln Val Val Thr Gln His Ala Ala Phe Gly
225                 230                 235                 240

Tyr Ala Thr Glu Tyr Ala His Leu Trp Asp Ala Gln Asn Arg Leu Ile
                245                 250                 255

Ala Ile Ser Arg Gln Thr Val Thr Val Phe Ala
            260                 265

<210> SEQ ID NO 22
<211> LENGTH: 262
<212> TYPE: PRT
<213> ORGANISM: Caulobacter crescentus CB15
<220> FEATURE:
<223> OTHER INFORMATION: Amino acid sequence of hypothetical protein
      CC2472 (protein_id="NP_421275.1") (figure 32)

<400> SEQUENCE: 22

Met Thr Leu Tyr Thr Asp Leu Val Ala Ala Ile Ala Ser Thr Glu Thr
1               5                   10                  15

Gly Phe Ser Ala His Val Ser Asp Asp Trp Lys Gln Gly Arg Thr Thr
            20                  25                  30

Tyr Gly Gly Leu Ser Gly Ala Leu Cys Val Glu Ala Ala Leu Arg Ala
        35                  40                  45

Phe Pro Glu Ala Pro Pro Leu Arg Ser Ala Gln Phe Ala Phe Val Gly
    50                  55                  60

Pro Ala Ala Gly Glu Leu Ala Ile Ser Val Arg Pro Leu Arg Gln Gly
65                  70                  75                  80

Lys Ser Thr Leu Phe Val Ala Val Asp Leu Ile Gly Glu Gln Gly Val
                85                  90                  95

Ala Thr His Gly Val Leu Thr Phe Gly Ala Ala Arg Thr Ser Ala Ile
            100                 105                 110

Ser Tyr Glu Glu Val Leu Cys Pro Pro Val Ala Pro Ala Gly Ala Cys
        115                 120                 125

Glu Leu Phe Phe Pro Glu Asn Arg Gln Gly Ala Pro His Phe Ser Ala
    130                 135                 140

Gln Phe Glu Val Arg Lys Ala Gly Gly Thr Arg Pro Leu Ala Gly Gly
145                 150                 155                 160

Glu Pro Glu Tyr Leu Leu Trp Ile Arg His Arg Asp Pro Ala Ala Thr
                165                 170                 175

Ser Ile Ser Ala Leu Val Ala Leu Ala Asp Met Pro Pro Pro Pro Ala
            180                 185                 190

Met Ala Leu Phe Pro Gln Phe Gly Pro Ile Ser Thr Met Thr Trp Ser
        195                 200                 205

Leu Asp Ile Val Gly Leu Pro Glu Ala Asp Asp Gly Trp Arg Leu
    210                 215                 220

Leu Arg Thr Arg Ala Glu Thr Ile Gly Asp Gly Tyr Ser Thr Gln Glu
225                 230                 235                 240

Met His Leu Trp Asp Ala Lys Gly Arg Pro Leu Val Leu Ala Arg Gln
                245                 250                 255

Asn Val Ala Ile Phe Val
            260
```

```
<210> SEQ ID NO 23
<211> LENGTH: 258
<212> TYPE: PRT
<213> ORGANISM: Erythrobacter litoralis HTCC2594
<220> FEATURE:
<223> OTHER INFORMATION: Amino acid sequence of hypothetical protein
      ELI0992 (protein_id=ZP_00375750.1) (figure 33)

<400> SEQUENCE: 23
```

Met Ser Val Ser Asp Leu Arg Ala Pro Ile Thr Ser Glu Gly Gly Ala
1               5                   10                  15

Val Thr Leu Pro Ala Asp Lys Trp Leu Gln Gly Arg Thr Leu Phe Gly
            20                  25                  30

Gly Ala Ser Ala Leu Val Ala Tyr Thr Ala Ala Val Arg Ala Phe Pro
        35                  40                  45

Asp Leu Pro Pro Leu Arg Ala Ala Gln Ile Gly Phe Val Ala Pro Val
    50                  55                  60

Gly Lys Asp Val Glu Thr Arg Ala Ala Met Val Arg Gln Gly Arg Asn
65                  70                  75                  80

Val Ala Gln Val Arg Ser Glu Leu Leu Val Glu Gly Lys Val Ala Leu
                85                  90                  95

Thr Ala Phe Trp Leu Phe Gly Thr Gly Arg Glu Ala Asn Ala Val His
            100                 105                 110

Ala Ala Ala Lys Ala Asp Pro Trp Pro Gly Ala Pro Glu Glu Asn Asp
        115                 120                 125

Ser Ala Met Thr Asp Lys Gly Pro Pro Phe Ile Val Asn Asn Phe Asp
    130                 135                 140

Ile Arg Arg Ala Gln Glu Thr Gln Gly Pro Gly Glu Pro Ile Val Arg
145                 150                 155                 160

Arg Trp Phe Arg Leu Thr Asp Arg Gly Glu Leu Asp Arg Val Ser Glu
                165                 170                 175

Leu Ile Leu Val Gly Asp Thr Leu Pro Pro Gly Ala Met Arg Ala Met
            180                 185                 190

Gln Arg Gln Gly Pro Ile Ser Ser Ile Asn Trp Ser Phe Asn Ile Leu
        195                 200                 205

Asp Ala Glu Leu Gly Thr Arg Asp Gly Trp Trp Leu Gly Glu Thr Ala
    210                 215                 220

Ser Gln His Ala Gly Ala Gly Tyr Ser Ser Glu Arg Leu Arg Leu Trp
225                 230                 235                 240

Asn Ala Asp Gly Val Gln Val Met Asp Gly Leu Gln Ser Val Ala Val
                245                 250                 255

Phe Gly

```
<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Primer (OTR
      End) used in Example 1

<400> SEQUENCE: 24
ggccgcactt gtgtataaga gtcag                                               25

<210> SEQ ID NO 25
<211> LENGTH: 25
<212> TYPE: DNA
<213> ORGANISM: Artificial Sequence
```

```
<220> FEATURE:
<223> OTHER INFORMATION: Description of Artificial Sequence: Primer (1TR
      End) used in Example 1

<400> SEQUENCE: 25
gcggccagat ctgatcaaga gacag                                           25

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer
      1086F used in Example 1

<400> SEQUENCE: 26
ttactggctt cgcaggaatg g                                               21

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Primer
      IntSM160 used in Example 1

<400> SEQUENCE: 27
cttggcaccc agcatgcgcg agcagg                                          26

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer
      1087F used in Example 3

<400> SEQUENCE: 28
cagtgatggc tatggtcaaa g                                               21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer
      1087R used in Example 3

<400> SEQUENCE: 29
ctttgatcag tccggcaaaa c                                               21

<210> SEQ ID NO 30
<211> LENGTH: 3902
<212> TYPE: DNA
<213> ORGANISM: Alcanivorax borkumensis
<220> FEATURE:
<223> OTHER INFORMATION: Nucleotide sequences of the genes tesB-like
      (Abo_1044) and plsC (Abo_1045) consisting of an operon in
      Alcanivorax borkumensis, with Tn5 inserted at position 588.

<400> SEQUENCE: 30
ggcttcgcag gaatggtaaa taaagcaccg caaattcaaa acacgcagaa gtgagagacc     60
atgacattcg atgagattct agccacgatt gatggccagg gtaacgccac gtttccagaa    120 gggtggggc agggccggac cttatttggt ggcctggtgg gggcggtgct gtttgaacat    180
ttagaaaaaa ccgtggctcg cgggaggttt ctacgtagtt tttctctctc ttttgtcgcc    240
```

```
cctgcggtgc cgggtccggt ggcactagac gagactgtgt ttcgggaagg caaatccgtt    300
atgcaggcca tggtctccgc ccgtcaagga gggcaggtgg tggcggttat gttggccagc    360
tttggggcca gtcgccaatc cagtgtagtg gtagaagggc catcggcccc agtgatgaaa    420
tctccagagc agagtatttc ggtaccgttt atcaaaggat tgacgccgga ttttttttcc    480
cattttaata tccattacgc agaaggcatg ccgccgttca gtggcagttc tgagcccgat    540
tacggtggtt acatggggtt tactgtgccg ccggaaacca tgagcacctg tctcttgatc    600
agatctggcc acctaggccg aattcccggg gatccggtga ttgattgagc aagctttatg    660
cttgtaaacc gttttgtgaa aaattttta aataaaaaa ggggacctct agggtcccca     720
attaattagt aatataatct attaaaggtc attcaaaagg tcatccaccg gatcacctta    780
ccaagccctc gctagattgt taatgcgat gttgcgatta cttcgcccaa ctattgcgat    840
aacaagaaaa gcgccttca tgatatatct cccaatttg tgtagggctt attatgcacg      900
cttaaaaata taaaagcga cttgacctga tagtttggct gtgagcaatt atgtgcttag    960
tgcatctaac gcttgagtta accgcgccgc gaagcggcgt cggcttgaac gaattgttag   1020
acattatttg ccgactacct tggtgattcg cctttcacgt agtggacaaa atcaaccaac   1080
tgatctgcgc gagcttcacg ctgccgcaag catcagggcg caagggctgc taaaggaagc   1140
ggaacacgta gaaagccagt ccgcagaaac ggtgctaccc cggatgaatg tcagctactg   1200
ggctatctgg acaagggaaa acgcaagcgc aaagagaaag aggtagcttg cagtgggctt   1260
acatgacgat agctagactg gcggtttta tggacagcaa gcgaaccgga attgccagct   1320
ggggcgccct ctggtaaggt tgggaagccc tgcaaagtaa actggatggc tttcttgccg   1380
ccaaggatct gatggcgcag gggatcaaga tctgatcaag agacaggatg aggatcgttt   1440
cgcatgattg aacaagatgg attgcacgca ggttctccgg ccgcttgggt ggagaggcta   1500
ttcggctatg actgggcaca acagacaatc ggctgctctg atgccgccgt gttccggctg   1560
tcagcgcagg ggcgcccggt tcttttgtc aagaccgacc tgtccggtgc cctgaatgaa   1620
ctgcaggacg aggcagcgcg gctatcgtgg ctggccacga cgggcgttcc ttgcgcagct   1680
gtgctcgacg ttgtcactga agcgggaagg gactggctgc tattgggcga agtgccgggg   1740
caggatctcc tgtcatctca ccttgctcct gccgagaaag tatccatcat ggctgatgca   1800
atgcggcggc tgcatacgct tgatccggct acctgcccat tcgaccacca agcgaaacat   1860
cgcatcgagc gagcacgtac tcggatggaa gccggtcttg tcgatcagga tgatctggac   1920
gaagagcatc aggggctcgc gccagccgaa ctgttcgcca ggctcaaggc gcgcatgccc   1980
gacggcgagg atctcgtcgt gacccatggc gatgcctgct tgccgaatat catggtggaa   2040
aatggccgct tttctggatt catcgactgt ggccggctgg gtgtggcgga ccgctatcag   2100
gacatagcgt tggctacccg tgatattgct gaagagcttg gcggcgaatg ggctgaccgc   2160
ttcctcgtgc tttacggtat cgccgctccc gattcgcagc gcatcgcctt ctatcgcctt   2220
cttgacgagt tcttctgagc gggactctgg ggttcgaaat gaccgaccaa gcgacgccca   2280
acctgccatc acgagatttc gattccaccg ccgccttcta tgaaaggttg gcttcggaa    2340 tcgtttccg ggacgccggc tggatgatcc tccagcgcgg ggatctcatg ctggagttct   2400
tcgcccaccc cgggctcgat cccctcgcga gttggttcag ctgctgcctg aggctggacg   2460
acctcgcgga gttctaccgg cagtgcaaat ccgtcggcat ccaggaaacc agcagcggct   2520
atccgcgcat ccatgccccc gaactgcagg agtgggagg cacgatggcc gctttggtcg   2580
acccggacgg gacggatcag tgagggtttg caactgtggg tcaaggatct ggatttcgat   2640
```

```
cacggcacga tcatcgtcgg gagggcaagg gctccaagga tcgggccttg atgttaccga    2700
gagcttggta cccagtctgt gtgagcaggg gaattgatcc ggtggatgac cttttgaatg    2760
acctttaata gattatatta ctaattaatt ggggacccta gaggtcccct ttttatttt    2820 aaaaattttt tcacaaaacg gtttacaagc ataaagcttg ctcaatcaat caccggatcc    2880
ccgggaattc gtcgacaagc tgcggccgcc taggccgtgg ccgaacttgt gtataagagt    2940
cagcgcagcg ctgattgcat tggtggatac ctgggcgcct tcagttttac ctctgctcaa    3000
agggccagca cccgccagtt ccttgacctg gaccatggag ctcttggatg accctagtgt    3060
ccactcgccg gagactttat ggcaatatcg ggtaaacacg gaccaatgca gtgatggcta    3120
tggtcaaagt caggcggtgg tttgggatgc tgcgggtaag gctgtggcgt tgagtcgaca    3180 aaccttacg gtatttgcat gaaatcggaa ctggtgccac tcacggcgcg gactttaggt    3240
aagcaagtgc ctcgtcgtgg gcactggctg ttggcggcgc tagggcggct gattttgact    3300
gttatggggt ggcgtattgt tggtgatttg cccgatacgc ctcgggcagt tttggcggtg    3360
gcgccacaca cgtcgaacat agacggggtc attggtatca gtgctattca gtctttgcgc    3420
ttggatgtgc gcttcatggg taagcacacg ttgtttaaag gtcgtcttgg gcggttcatg    3480
tactggctgg gcggcatccc tgtgaatcga gaaagtgcca gggatgtggt ggaccagacg    3540
acgtcggtga tgggggaaac accatttggg cttgggctaa cgccggaggg gacgcgtaaa    3600
ggcgccaagc gttggaaaac cgggttttac cgtattgctg agcaaatgca ggtgccgatt    3660
gtcgtgttag gtttctgtta ccggcgccgg caggtccgga ttgtagattg ctttctgccg    3720
acgggcgata ttgatgctga tatggcgcga atgaccgcgt cgttggcgga tattgttccg    3780
cgcaaacctg cgcagttatc cgccccgctg aaagcggaaa agctgctcg cggcattgat    3840 tgattcagac gttggcagtt ttgccggact gatcaaggag atgctggcgg tgctgggcgg    3900
at                                                                    3902
```

<210> SEQ ID NO 31
<211> LENGTH: 3142
<212> TYPE: DNA
<213> ORGANISM: Alcanivorax borkumensis
<220> FEATURE:
<223> OTHER INFORMATION: Nucleotide sequence of tesB-like acyl-CoA thioesterase from Alcanivorax borkumensis (Abo_1044), with Tn5 inserted at position 558.

<400> SEQUENCE: 31

```
atgacattcg atgagattct agccacgatt gatggccagg gtaacgccac gtttccagaa     60 gggtggggc agggccggac cttatttggt ggcctggtgg gggcggtgct gtttgaacat    120
ttagaaaaaa ccgtggctcg cgggaggttt ctacgtagtt tttctctctc ttttgtcgcc    180
cctgcggtgc cgggtccggt ggcactagac gagactgtgt tcgggaagg caaatccgtt    240 atgcaggcca tggtctccgc ccgtcaagga gggcaggtgg tggcggttat gttgccagc    300 tttggggcca gtcgccaatc cagtgtagtg gtagaagggc catcggcccc agtgatgaaa    360
tctccagagc agagtatttc ggtaccgttt atcaaaggat tgacgccgga tttttttcc    420 catttaata tccattacgc agaaggcatg ccgccgttca gtggcagttc tgagcccgat    480
tacggtggtt acatggggtt tactgtgccg ccggaaacca tgagcaccgc agcgctgatt    540
gcattggtgg ataccgctg tctcttgatc agatctggcc acctaggccg aattcccggg    600
gatccggtga ttgattgagc aagctttatg cttgtaaacc gttttgtgaa aaaatttta    660 aaataaaaaa ggggacctct agggtcccca ttaattagt aatataatct attaaaggtc    720
```

-continued

```
attcaaaagg tcatccaccg gatcaccttg ccaagccctc gctagattgt taatgcggat    780
gttgcgatta cttcgcccaa ctattgcgat aacaagaaaa gcgcctttca tgatatatct    840
cccaattttg tgtagggctt attatgcacg cttaaaaata ataaaagcga cttgacctga    900
tagtttggct gtgagcaatt atgtgcttag tgcatctaac gcttgagtta accgcgccgc    960
gaagcggcgt cggcttgaac gaattgttag acattatttg ccgactacct tggtgattcg   1020
cctttcacgt agtggacaaa atcaaccaac tgatctgcgc gagcttcacg ctgccgcaag   1080
catcagggcg caagggctgc taaaggaagc ggaacacgta gaaagccagt ccgcagaaac   1140
ggtgctaccc cggatgaatg tcagctactg ggctatctgg acaagggaaa cgcaagcgc    1200 aaagagaaag aggtagcttg cagtgggctt acatgacgat agctagactg gcggttttta   1260
tggacagcaa gcgaaccgga attgccagct ggggcgccct ctggtaaggt tgggaagccc   1320
tgcaaagtaa actggatggc tttcttgccg ccaaggatct gatggcgcag gggatcaaga   1380
tctgatcaag agacaggatg aggatcgttt cgcatgattg aacaagatgg attgcacgca   1440
ggttctccgg ccgcttgggt ggagaggcta ttcggctatg actgggcaca acagacaatc   1500
ggctgctctg atgccgccgt gttccggctg tcagcgcagg ggcgcccggt tcttttgtc    1560 aagaccgacc tgtccggtgc cctgaatgaa ctgcaggacg aggcagcgcg gctatcgtgg   1620
ctggccacga cgggcgttcc ttgcgcagct gtgctcgacg ttgtcactga agcgggaagg   1680
gactggctgc tattgggcga agtgccgggg caggatctcc tgtcatctca ccttgctcct   1740
gccgagaaag tatccatcat ggctgatgca atgcggcggc tgcatacgct tgatccggct   1800
acctgcccat tcgaccacca agcgaaacat cgcatcgagc gagcacgtac tcggatggaa   1860
gccggtcttg tcgatcagga tgatctggac gaagagcatc aggggctcgc gccagccgaa   1920
ctgttcgcca ggctcaaggc gcgcatgccc gacggcgagg atctcgtcgt gacccatggc   1980
gatgcctgct tgccgaatat catggtggaa aatggccgct tttctggatt catcgactgt   2040
ggccggctgg gtgtggcgga ccgctatcag gacatagcgt tggctacccg tgatattgct   2100
gaagagcttg gcggcgaatg ggctgaccgc ttcctcgtgc tttacggtat cgccgctccc   2160
gattcgcagc gcatcgcctt ctatcgcctt cttgacgagt tcttctgagc gggactctgg   2220
ggttcgaaat gaccgaccaa gcgacgccca acctgccatc acgagatttc gattccaccg   2280
ccgccttcta tgaaaggttg gcttcggaa tcgttttccg gacgccggc tggatgatcc    2340 tccagcgcgg ggatctcatg ctggagttct tcgcccaccc cgggctcgat cccctcgcga   2400
gttggttcag ctgctgcctg aggctggacg acctcgcgga gttctaccgg cagtgcaaat   2460
ccgtcggcat ccaggaaacc agcagcggct atccgcgcat ccatgccccc gaactgcagg   2520
agtggggagg cacgatggcc gctttggtcg acccggacgg gacggatcag tgagggtttg   2580
caactgtggg tcaaggatct ggatttcgat cacggcacga tcatcgtcgg gagggcaagg   2640
gctccaagga tcgggccttg atgttaccga gagcttggta cccagtctgt gtgagcaggg   2700
gaattgatcc ggtggatgac cttttgaatg acctttaata gattatatta ctaattaatt   2760 ggggaccta gaggtcccct ttttatttt aaaattttt tcacaaaacg gtttacaagc     2820
ataaagcttg ctcaatcaat caccggatcc ccgggaattc gtcgacaagc tgcggccgcc   2880
taggccgtgg ccgaacttgt gtataagagt cagggcgcct tcagttttac ctctgctcaa   2940
agggccagca cccgccagtt ccttgacctg gaccatggag ctcttggatg acctagtgt    3000 ccactcgccg gagactttat ggcaatatcg ggtaaacacg gaccaatgca gtgatggcta   3060
```

```
tggtcaaagt caggcggtgg tttgggatgc tgcgggtaag gctgtggcgt tgagtcgaca   3120
aacctttacg gtatttgcat ga                                            3142
```

EXTRACELLULAR POLYHYDROXYALKANOATES PRODUCED BY GENETICALLY ENGINEERED MICROORGANISMS

CROSS REFERENCE TO RELATED APPLICATIONS

The present application is a National Stage Application claiming the priority of co-pending PCT Application No. PCT/EP2006/007888 filed Aug. 9, 2006, which in turn, claims priority from European Application Serial No. 05017308.7, filed Aug. 9, 2005. Applicants claim the benefits of 35 U.S.C. §120 as to the PCT application and priority under 35 U.S.C. §119 as to the said European application, and the entire disclosures of both applications are incorporated herein by reference in their entireties.

The present invention is in the field of biosynthesis of polyhydroxyalkanoates (PHA). The invention relates to a genetically engineered microorganism having at least one gene involved in the metabolism, preferably in the production, of polyhydroxyalkanoates (PHA). This microorganism is useful in commercial production of polyhydroxyalkanoates. The present invention further relates to a method for the production of polyhydroxyalkanoates (PHA).

Polyhydroxyalkanoates (PHA) are polymers that are biodegradable and biocompatible thermoplastic materials (polyesters of 3-hydroxy fatty acids), produced from renewable resources, with a broad range of industrial and biomedical applications (Williams and Peoples, 1996). Polyhydroxyalkanoates (PHA) are synthesized by a broad range of bacteria and have been extensively studied due to their potential use to substitute conventional petrochemical plastics to protect the environment from harmful effects of plastic wastes.

PHA can be divided into two groups according to the length of their side chains and their biosynthetic pathways. Those with short side chains, such as PHB, a homopolymer of (R)-3-hydroxybutyric acid units, are crystalline thermoplastics, whereas PHA with long side chains are more elastomeric. The former have been known for about seventy years (Lemoigne and Roukhelman, 1925), whereas the latter materials were discovered relatively recently (deSmet et al., 1983, J. Bacteriol. 154: 870-78). Before this designation, however, PHA of microbial origin containing both (R)-3-hydroxybutyric acid units and longer side chain (R)-3-hydroxyacid units from 5 to 16 carbon atoms had been identified (Wallen, Rohweder, 1974, Environ. Sci. Technol. 8: 576-79). A number of bacteria which produce copolymers of (R)-3-hydroxybutyric acid and one or more long side chain hydroxyacid units containing from 5 to 16 carbon atoms have been identified (Steinbuchel, Wiese, 1992, Appl. Microbiol. Biotechnol. 37: 691 97; Valentin et al., 1992, Appl. Microbiol. Biotechnol. 36: 507-14; Valentin et al., Appl. Microbiol. Biotechnol. 1994, 40: 710-16; Abe et al., 1994, Int. J. Biol. Macromol. 16: 115-19; Lee et al., 1995, Appl. Microbiol. Biotechnol. 42: 901-09; Kato et al., 1996, Appl. Microbiol. Biotechnol. 45: 363-70; Valentin et al., 1996, Appl. Microbiol. Biotechnol. 46: 261-67; U.S. Pat. No. 4,876,331). These copolymers can be referred to as PHB-co-HX (wherein X is a 3-hydroxyalkanoate or alkanoate or alkenoate of 6 or more carbons). A useful example of specific two-component copolymers is PHB-co-3-hydroxyhexanoate (PHB-co-3HH) (Brandi et al., 1989, Int. J. Biol. Macromol. 11: 49-55; Amos & McInerey, 1991, Arch. Microbiol. 155: 103-06; U.S. Pat. No. 5,292,860).

However, although PHAs have been extensively studied because of their potential use as renewable resource for biodegradable thermoplastics and biopolymers (as mentioned above) and have been commercially developed and marketed (Hrabak, O. 1992), their production costs are much higher than those of conventional petrochemical-based plastics, thus presenting a major obstacle to their wider use (Choi and Lee 1997). As described above, many bacteria produce PHA, e.g. *Alcaligenes eutrophus, Alcaligenes latus, Azotobacter vinlandii, Pseudomonas acitophila, Pseudomonas oleovarans, Eschericha coli, Rhodococcus eutropha, Chromobacterium violaceum, Chromatium vinosum, Alcanivorax borkumensis* etc. All PHA producing bacteria known in the art produce intracellular PHA and accumulate it in PHA granules (Steinbüchel, 1991). The main aspect which renders PHA production expensive and therefore unfavorable as compared to petrochemical-based plastic, is the difficulty to recover produced PHA from within the bacterial cells where it is accumulated. In order to reduce the total production costs of PHA the development of an efficient recovery process was considered to be necessary generally aiming at cell disruption (Lee 1996) by
   i) an appropriate solvent,
   ii) hypochlorite extraction of PHA and/or
   iii) digestion of non-PHA cellular materials.

However, at an industrial scale, all methods known in the art require large amounts of chemical reagents and/or enzymes which is an obstacle to reducing the recovery cost. Therefore, alternative strategies for PHA recovery are in urgent need.

The object of the present invention is to provide a system permitting production of commercially significant levels of PHA while reducing the costs for recovering produced PHA.

This technical problem is solved by the invention, especially in providing a microorganism that complies with the aforementioned requirements and is applicable in said system.

The invention relates in its first embodiment to a genetically engineered microorganism having at least one modification in at least one gene encoding for a protein involved in the metabolism of polyhydroxyalkanoate(s) (PHA) or, preferably, in at least one gene encoding for a protein, which interferes in the metabolism of the microorganism with the production of PHA, wherein the at least one modification causes extracellular deposition, e.g. excretion, of polyhydroxyalkanoate(s) (PHA), preferably medium or long chain polyhydroxyalkanoate(s) (PHA), produced by the microorganism, preferably in/into the culture medium. Preferably, the microorganism comprises one of the nucleic acid sequences shown in FIGS. 11, 12, 14, 16 and 18 to 25 (SEQ ID NOs: 1, 2, 4, 6, and 8 to 15 respectively) or a functional fragment or variant thereof. More preferably, the microorganism may comprise nucleic acids 180 to 680, preferably 230 to 640, more preferably 310 to 550, most preferably 350 to 510, according to one of the nucleic acid sequences shown in FIGS. 11, 12, 14, 16 and 18 to 25 (SEQ ID NOs: 1, 2, 4, 6, and 8 to 15), or a functional fragment or variant thereof.

It has been found by the inventors that a genetically engineered microorganism according to the invention produces extracellular PHA by extracellularly depositing, e.g. excreting PHA (produced intracellularly) in/into the culture medium. The deposition, e.g. excretion of PHA by a microorganism has not been described before in the art. Preferably, the microorganism of the present invention produces large amounts of PHA, preferably overproduces PHA, and deposits a large proportion of its PHA product in the extracellular medium, unlike the microorganisms known in the art. Extracellular deposition, e.g. excretion, and overproduction of large amounts PHA into the culture medium was achieved by modifying at least one gene encoding a polypeptide involved in the metabolism of PHA or, preferably by introducing at least one modification in a gene encoding a polypeptide (enzyme) interfering with the production of PHA. The term "polypeptide" according to the invention also encompasses the terms "peptide", "protein" or "enzyme".

Various genes encoding polypeptides are involved in the metabolism of PHA. Several of these genes are specified in Table 1 as represented by FIG. 5. Thus, a gene according to the invention encompasses any gene encoding a polypeptide which is involved in PHA metabolism, preferably in PHA production. Preferably, such gene encodes (without being restricted to) PHA synthase, poly(3-hydroxyalkanoate)synthase, enyol-CoA hydratase, and PHB synthase.

Other enzymes, which are also involved in the fatty acid metabolism, e.g. fatty acid synthesis or beta-oxidation (poly (3-hydroxybutyrate)depolymerase, acyl-CoA transferase, reductase, or thiolase), may be modified as well. However, these enzymes do not specifically influence PHA synthesis and are, therefore, less preferred for a modification allowing to increase PHA synthesis.

Preferably, the set of genes required for PHA production is not compromised in a microorganism of the invention. Any modification introduced into any of the PHA production genes (see above) is preferably intended not to reduce, but to enhance their enzymatic activity. Thereby, the microorganism according to the invention is allowed to provide a higher yield of PHA than microorganisms known in the art.

In contrast, a microorganism according to the invention contains most preferably modifications in any genes encoding for polypeptides which compromise the production of PHA. In particular, a microorganism according to the invention is modified in a gene encoding_enzymes which cleave Acyl-CoA molecules by a thioesterase function, e.g. Acyl-CoA thioesterases. Depending on the specific microorganisms one or more Acyl-CoA thioesterases are acting on the fatty acid metabolism. Acyl-CoA thioesterases were especially studied in *E. coli* possessing two of such enzymes called acyl-CoA thioesterase I (encoded by tesA gene) and acyl-CoA thioesterase II (encoded by tesB gene). Thioesterase I exhibits specificity towards C12 to C18 acyl-CoA esters (Bonner, W M et al., 1972, J. Biol. Chem. 247, 3123-3133), while thioesterase II cleaves C6 to C18 acyl-CoA esters as well as β-hydroxyacyl-CoA esters of chain length C12 to C18 (Barnes et al., 1970, The Journal of Biological Chemistry, vol. 245, No. 12, issue of Jun. 25, 3122-3128). TesA is implicated in chain termination of de novo biosynthesis of fatty acids and mediates acyl-ACP intermediates from the fatty acid de novo biosynthesis pathway to fatty acid β-oxidation in *E. coli* (Klinke, S Q et at., 1999, Appl. Environ. Microbiol. 65: 540-548). Up to now, little was known on physiological role of tesB in bacterial metabolism.

A very recent report described that thioesterase II plays an important role in 3-hydroxyalkanoic acid (3-HAA) production (Zweng, Z et al., 2004, Appl. Environ. Microbiol. 70(7): 3807-3813) by cleaving 3-hydroxyacyl-CoA thioester bonds thereby converting them into free 3-HAA. According to the invention, it was found that various microorganisms express thioesterases which act with a high specific activity on the cleavage of 3-hydroxyacyl-CoAs which forms the building block of PHA synthesis. These thioesterases allow to release free 3-HAAs. However, the conversion to 3-HAA is a reaction which competes with the synthesis of PHA by PHA-synthase, which acts on the same cellular intermediate (namely 3-hydroxyacyl-CoAs). According to the invention, it was found that (i) the release of free 3-HAAs and the synthesis of PHA are interfering metabolic pathways and (ii) that functional knock-out of the specific thioesterase, herein termed tesB-like thioesterase, provides for deposition of PHA in the extracellular medium. A functional knock-out mutation in a tesB-like gene (as described below in more detail) was identified to increase the intracellular amount of 3-hydroxyacyl-CoA in a number of microorganism, thereby guiding the metabolism of 3-hydroxyacyl-CoA (as PHA precursor) towards PHA synthesis (see FIG. 8).

As explained above, the present invention is based on the general finding that (knock-out) modifications of thioesterases using (R)-3-OH-acyl-CoA as substrate allow PHA producing microorganisms to deposit PHA in the extracellular medium. While e.g. in *Alkanivorax, Pseudomonas putida, Pseudomonas aeruginosa, Pseudomonas syringae, Pseudomonas fluorescens, Acinetobacter* sp., *Caulobacter crescentus* the thioesterase found to act specifically on (R)-3-OH-acyl-CoA, is acyl-CoA thioesterase tesB-like, other PHA producing microorganism being based on a slightly different metabolism use other thioesterase, e.g. acyl-CoA thioesterase tesB or tesA, to produce 3-HAA.

In any case, a modification of an thioesterase specifically using (R)-3-OH-acyl-CoA to produce 3-HAA is most preferably expected to either reduce the thioesterase activity, e.g. of acyl-CoA thioesterase tesB-like, considerably, e.g. by at least 50%, more preferably by at least 60%, even more preferably by at least 80%, more preferably by at least 90%. In a particularly preferred embodiment, the enzymatic activity of this thioesterase, e.g. acyl-CoA thioesterase tesB-like, is completely switched off.

The present invention also encompasses tesB-like homologs of proteins as disclosed herein (and as well their encoding nucleic acids), particularly of thioesterases. In the context of the present invention tesB-like homologs of proteins as disclosed herein is meant to include any protein or peptide sequence, occurring in a different microorganism than a tesB-like homolog of proteins as disclosed herein, which preferably show a (significant) homology to this tesB-like protein and display similar or even identical biological function. A (significant) homology to a tesB-like protein as shown herein may be easily determined by a skilled person using method well known in the art, e.g. methods for determining sequence identities as also disclosed herein or by activity assays.

According to the finding of the present invention Alkanivorax is characterized by two tesB thioesterases, namely acyl-CoA thioesterase tesB-like specifically acting on (R)-3-OH-acyl-CoA to produce 3-HAA and acyl-CoA thioesterase tesB, which is involved in the production of fatty acids. By performing homology searches (BLAST searches) in several PHA producing bacteria the inventors have screened for other microorganisms showing the same or a similar metabolic structure as in Alkanivorax (with a homologue of the highly specific acyl-CoA thioesterase tesB-like and another thioesterase (tesB)).

Both types of thioesterases being present in *Alcanivorax borkumensis* SK2 are also expressed in a number of closely related PHA producing gamma-proteobacteria (e.g., *Pseudomonas putida, P. aeruginosa, P. aeruginosa, P. syringae, P. fluorescens, Idiomarina loihiensis, Acinetobacter* sp., *Caulobacter crescentus*). The homologues of the Alkanivorax tesB-like protein are named differently in the other microorganisms, e.g. as tesB-like thioesterase, putative acyl-CoA thioesterase II or hypothetical protein. However, it is to be understood that the term "tesB-like" is intended to encompass all these thioesterases of the aforementioned microorganism with deviating nomenclature. These homologues of the Alkanivorax tesB-like thioesterase are presented in Table 4

(see Table 4 of FIG. 10). The presence of two thioesterases in Alkanivorax and the other aforementioned microorganisms, namely the tesB and tesB-like proteins, is explained by the present inventors by different functions of tesB and tesB-like proteins. Most likely, the tesB protein exclusively acts on C6 to C18 acyl-CoA derivatives, whereas the tesB-like protein exclusively cleaves hydroxyacyl-CoAs. This conclusion was supported by an earlier study of tesB protein showing that unlike similar thioesterase II in *E. coli* (Barnes et al., supra), tesB thioesterase II of PHA-producing *Rhodobacter sphaeroides* (Wieczorek, R A et al., 1996, FEMS Microbiology Letters 135: 23-30) is not able to hydrolyze 3-hydroxyacyl-CoA substrates (Seay, T et al., 1982, Biochemistry May 6, 25(9): 2480-2485).

In a preferred embodiment, the microorganism of the present invention typically contains at least one modified gene as outlined above, wherein the modified gene is integrated into its chromosome.

The modification of at least one of said genes encoding a protein involved in PHA metabolism and/or, preferably, the degradation of (R)-3-OH-acyl-CoA is achieved by inserting a mutation in the nucleic acid sequence of the gene using genetic engineering techniques. The term "genetically engineered" (or genetically modified) means the artificial manipulation of a microorganism of the invention, its gene(s) and/or gene product(s) (polypeptide). Subsequently, the modification (mutation) was confirmed by sequence analysis (see e.g. nucleic acid and amino acid sequences of FIGS. 11 to 14 and 15 to 33, SEQ ID NOs: 1-4 and 5-23, respectively, as well as Examples).

The term "modification" encompasses any manipulation and mutation of a microorganism of the invention, especially of at least one gene of said microorganism of the invention. Preferably, the modification results in an alteration of the nucleic acid sequence(s) of said at least one gene and is typically expressed on the amino acid sequence level accordingly or may be due to a modification in the regulatory regions, e.g. promotor regions of the gene. Preferably, the modification resulting in an alteration of said nucleic acid sequence(s) is carried out by addition, substitution, deletion or insertion of one or more nucleotide(s). Furthermore, the modification may encompass one or more additional copies of a gene in a microorganism and/or (complete) deletion of a gene. Deletion may also be due to a disruption of the gene by recombination or insertion of e.g. a transposon. In a preferred embodiment, a modification within a microorganism according to the present invention causes a complete or partial inactivation of at least one gene encoding a protein which is involved in the metabolism interfering with the production of PHA (e.g. by biochemically converting intermediates of the PHA synthesis pathway), more preferably a thioesterase, even more preferably a thioesterase, which degrades intermediates of the PHA synthesis pathway, and most preferably a thioesterase, which converts (specifically) (R)-3-OH-acyl-CoA to 3-HAA. In the most preferred embodiment of the present invention the microorganism is defective with regard to the tesB-like thioesterase (Alkanivorax) or a homologue thereof (in other microorganisms). The defective character may be due to various modification on the genetic level or may be due to posttranscriptional modifications reducing or abolishing the enzymatic activity of the relevant thioesterase.

Additionally, modifications in one or more of the genes involved in the PHA synthesis may occur in the microorganism according to the invention. These modifications may be directed to PHA synthase, poly(3-hydroxyalkanoate)synthase, enyol-CoA hydratase, and/or PHB synthase and/or other enzymes involved in the fatty acid metabolism. Genes encoding for enoyl-CoA hydratase in Alcanivorax are e.g. ABO 2240; ABO_0526; ABO_1238; ABO_0987; ABO_0148; or ABO_1645. Enoyl-CoA hydratase links beta-oxidation with PHA biosynthesis catalyzing production of 3-hydroxy-acyl-CoA from enoyl-CoA, an intermediate of beta-oxidation. 3-hydroxy-acyl-CoA is a precursor of PHA and is incorporated by phaC synthase to PHA. There are two genes encoding PHA synthases in Alcanivorax: ABO_2214 and ABO_1418. PHA synthases catalyze the crucial last step in biosynthesis of PHA. Generally, the enzymatic activity of these enzymes is enhanced due to the modification(s) introduced.

According to the invention the genetically engineered microorganism has at least one modification in at least one gene encoding a protein which is involved in the metabolism interfering with the production of PHA and, optionally, at least one modification of a gene involved in PHA metabolism. Thus, it is possible that the microorganism has only one modification in one gene encoding a protein which is involved in the metabolism interfering with the production of PHA. However, it is also possible that the microorganism has more than one (two or more) modification(s) in the same gene or in two (or more) different genes involved in the relevant metabolism of the microorganism according to the invention. In this case, it is possible that the more than one modification causes different results or phenotypes. For example, one of these modifications results in PHA excretion whereas another modification results in PHA overproduction (as mentioned below).

Moreover, it is also possible that the microorganism according to the present invention has more than one modification in different genes with differing functions, namely (at least) one modification occurs in (at least) one gene encoding a protein which is involved in the metabolism interfering with the production of PHA, whereas (at least) one other modification occurs in (at least) one gene which is involved in PHA metabolism. In addition, further genes may be modified, e.g. genes encoding for a protein involved in secretion mechanisms. In such a case, it is also possible that (at least) one of these modifications results in (increased) PHA excretion whereas (at least) one other modification results in PHA overproduction (as mentioned below).

Several suitable genetic engineering technique known in the art can be used to generate a microorganism of the invention. In general, genes from any source can be broken into pieces and modified in various ways, using microorganisms and their enzymes or transposable elements as molecular tools. According to the present invention, it is even possible to construct at least one completely artificial gene which either involved in the metabolism of PHA by a microorganism of the invention (e.g. increasing the amount of PHA produced) and/or involved e.g. in the inhibition of 3-HAA production using genetic engineering techniques. Once the desired gene has been selected or created, it can be inserted into a microorganism of the invention where it can be expressed to produce the desired gene products. For example, a wide range of genetic engineering methods are based on molecular cloning. In molecular cloning, a DNA fragment from essentially any type of genetic element composed of double-stranded DNA is recombined with a vector and introduced into a suitable host. Commonly employed cloning vectors include, e.g., plasmids and bacteriophages (e.g., plasmid pBR322, bacteriophage lambda, also see below). Molecular cloning can be divided in single steps:

1. isolation and fragmentation of the source DNA (e.g. genomic DNA, cDNA, synthetic DNA etc.)
2. joining DNA fragments to a cloning vector with DNA ligase and
3. introduction and maintenance in a host organism (microorganism), e.g., by transformation.

Thereby, the microorganism of the invention may e.g. contain an artificial or native gene (operably coupled to a strong promoter), which expresses a protein of the PHA synthesis pathway in excess, thereby increasing the amount of PHA pathway intermediates. As a result, PHA is produced in larger amounts than naturally. The additional gene is inserted into the cell and may be located on a separate DNA molecule, e.g. a vector (e.g. a plasmid) or my be incorporated into the chromosome of the cell.

Another preferred technique to alter a nucleic acid sequence relates to oligonucleotide site-directed mutagenesis whereby a specific base pair in a gene can be changed to another base pair (see, e.g., Comack B, CURRENT PROTOCOLS IN MOLECULAR BIOLOGY, 8.01-8.5.9, Ausubel F, et al., eds. 1991). In this technique an oligonucleotide, whose sequence contains a mutation of interest, is synthesized as described supra. This oligonucleotide is then hybridized to a template containing the wild-type nucleic acid sequence. In a preferred embodiment of this technique, the template is a single-stranded template. Particularly preferred are plasmids which contain regions such as the f1 intergenic region. This region allows the generation of single-stranded templates when a helper phage is added to the culture harboring the phagemid. After annealing of the oligonucleotide to the template, a DNA-dependent DNA polymerase is used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding nucleic acid sequence may be placed immediately adjacent to whichever transcriptional or translational regulatory elements are employed by the practitioner. The construction protocols utilized for *E. coli* can be followed to construct analogous vectors for other organisms, merely by substituting, if necessary, the appropriate regulatory elements using techniques well known to skilled artisans.

An especially preferred technique according to the invention relates to transposon mutagenesis, a type of random recombination. This procedure usually involves breakage reactions at the ends of the mobile DNA segments embedded in chromosomes and the attachment of those ends at one of many different non-homologous target DNA sites. It does not involve the formation of heteroduplex DNA. Transposons can be used as mutagenic agents without the use of chemical or physical agents. Transposons (also called transposable elements) can be integrated in the chromosome (e.g. of a bacterium) at various locations and causes mutations (mutations are defined as inherited or artificial changes in the base sequence of nucleic acids and/or in the amino acid sequence of peptides or polypeptides), wherein an insertion within a gene generally results in the loss of gene function. Thus, they provide facile means of creating mutants throughout the chromosome. The most convenient element for transposon mutagenesis is one containing an antibiotic resistance gene. Clones containing the transposon can then be selected by isolation of antibiotic-resistance colonies. Two transposons widely used for mutagenesis are Tn10, which contains a marker for tetracycline resistance, and Tn5, which confers neomycin and kanamycin resistance. Accordingly, a preferred embodiment relates to a microorganism of the invention, wherein the at least one modification is performed by transposon mutagenesis, preferably based on miniTn5 kanamycin element (miniTn5 Km element) (sequences see FIGS. 14 and 15; SEQ ID NOs: 4 and 5, respectively), more preferably miniTn5 streptomycin element (miniTn Str/Sp element) (see Example 1).

In a preferred embodiment of the present invention, the microorganism contains a modification, which causes polar effects subsequent to transposon insertion, preferably Tn-5 insertion, on the gene downstream to the modified gene as described below.

Another useful technique relates to conservative site-specific recombination involving the production of very short heteroduplex joint and therefore requiring a short DNA sequence that is the same on both donor and recipient DNA molecules. In this pathway, breakage and joining occur at two special sites, one on each participating DNA molecule. The double-stranded molecule obtained is inserted into a cloning host by transformation and mutants are selected. Depending on the orientation of the two recombination sites, DNA integration, DNA excision or DNA inversion can occur. Conservative site-specific recombination is especially usable to turn genes on or off.

As mentioned above, the at least one modification of at least one gene encoding a protein which is involved in the metabolism interfering with the production of PHA and/or a gene encoding a protein involved in PHA metabolism leads to extracelluar deposition, e.g. excretion, of polyhydroxyalkanoate(s) (PHA), preferably medium or long chain polyhydroxyalkanoate(s) (PHA), produced by the microorganism, preferably into the surrounding medium. Thus, microorganism of the invention typically deposits, e.g. excretes, polyhydroxyalkanoates (PHA), preferably medium or long chain polyhydroxyalkanoates (PHA), preferably into the surrounding natural or culture medium. According to the invention the term "deposition" or "deposited" means that the microorganism releases the (intracellular) produced PHA, preferably into the surrounding medium which is a culture medium containing all necessary components and suitable conditions (nutrients, buffer, pH, temperature) for existence and growth of the microorganism. The deposition may be due to an active process of living cells ("excretion") and/or due to the release of PHA from microorganisms dying subsequent to PHA (over)production. A typically polyester of hydroxyacid units (PHA) contains side chain hydroxyacid units [(R)-3-hydroxyacid units] from 5 to 16 carbon atoms. The term "long chain PHA" is intended to encompass PHA containing at least 12, preferably at least 14 carbon atoms per monomer (molecule), whereas 5 to 12 carbon atoms are intended to be meant by "medium chain PHA".

According to the invention, overproduction of PHA by the microorganism of the invention has been shown (see FIGS. 1, 4, 6 and 7). Thus, microorganisms having at least one modification of at least one gene encoding a protein which is involved in the metabolism interfering with the production of PHA, in particular a modification leading to a (partially) defective thioesterase, more particularly to a (partially) thioesterase using (R)-3-OH-acyl-CoA as a substrate with high specificity show generally (in addition to deposition of PHA in the culture medium) an overproduction of polyhydroxyalkanoate(s) PHA, preferably medium and/or long chain polyhydroxyalkanoates (PHA). The term "overproduction" means a PHA production by a microorganism of the invention which is at least 5 times, preferably at least 10 times, more preferably at least 15 times, more preferably at least 25 times, even more preferably at least 40 times, even more preferably at least 50 times, most preferably at least 60 times, most preferably at least 80 times, even most preferably at least 100 times higher than the PHA production of the corresponding wild type microorganism. Wild type microorganism means a PHA producing microorganism which is not genetically engineered and which genes are not artificially modified (mutated). Wild type microorganisms produce normal levels of PHA, but do not show deposition properties. In addition, the microorganism according to invention may contain at least one modification in a gene encoding a protein which is involved in PHA synthesis. This modification may be due to e.g. overexpression of the protein by a modified promoter or another modified regulatory element of the PHA synthesis gene or by additional copies of the PHA synthesis gene (achieved by e.g. transformation of the microorganism) or by a mutation within the coding region of the gene, which increases the activity and/or specificity of the PHA synthesis enzyme.

In general, the term "microorganism" means a large and diverse group of microscopic organisms that exist as single cells or cell clusters of procaryotic (e.g. bacteria, cyanobacteria) and eucaryotic (e.g. protozoa, fungi) microorganisms. A preferred microorganism according to the present invention is a PHA producing bacterium. The inventive microorganism to be used according to the present invention is preferably selected from the group consisting of PHA producing bacteria *Alcanivorax borkumensis*, *Pseudomonas putida*, *Pseudomonas aeruginosa*, *Pseudomonas syringae*, *Pseudomonas fluorescens*, *Idiomarina loihiensis*, *Acinetobacter* sp., *Caulobacter crescentus*. Nevertheless, any other PHA producing microorganism, e.g., *Alcaligenes eutrophus*, *Alcaligenes latus*, *Azotobacter vinlandii*, *Pseudomonas acitophila*, *Pseudomonas oleovarans*, *Rhodococcus eutropha*, *Chromobacterium violaceum*, *Chromatium vinosum* may be used as well. Moreover, any microorganism, which does not naturally produce PHA, may be used according to the invention, if such microorganism comprises an expression vector which comprises a gene cluster or a corresponding expression cassette, which allows to express the enzymes needed for PHA production, in particular PHA synthase, poly(3-hydroxyalkanoate)synthase, enyol-CoA hydratase, and/or PHB synthase, and contains at least one modification as disclosed above. Such an expression vector can be introduced into a microorganism, in particular into a cell of said microorganism, e.g., *Escherichia coli*, by any suitable method, e.g. by transfection, transduction, transformation etc. (see below).

An especially preferred microorganism according to the present invention is an oligotrophic bacterium, more preferably halophilic oligotroph bacterium, even more preferably marine oil-degrading bacterium, especially of the strain *Alcanivorax*, preferably *Alcanivorax borkumensis*, more preferably *Alcanivorax borkumensis* SK2. *A. borkumensis* is a marine oil-degrading bacterium widely distributed in the aquatic environments. It is a moderately halophilic oligotroph bacterium which is able to use essentially only petroleum hydrocarbons as carbon and energy sources. *A. borkumensis* is of particular interest because it is mostly found as predominant species in oil polluted sea water (Harayama et al., 1999; Kasai et al., 2001; 2002; Syutsubo et al., 2001) and, accordingly, has key applications for bioremediation purposes. For oligotrophic marine bacteria including *Alcanivorax* oil pollution constitutes temporary conditions of nutrient abundance, characterized by high C/N ratio. Under such conditions the microorganism will store excess of carbon for the use as energy source when lack of nitrogen will not more be a limiting factor. These conditions of high C/N ratio indeed favor microbial intracellular storage inclusions. Correspondingly, carbon excess allows PHA producing bacterial species to be accumulated in form of polyhydroxyalkanoate (PHA) granules (Steinbüchel 1991). Previously, it was described that *A. borkumensis* was not able to produce PHA (Yakimov et all. 1998). However, culturing conditions were not favorable for PHA accumulation due to relatively high nitrogen concentration in the culture medium (5 g/l). According to the invention, the complete genome of *A. borkumensis* was sequenced. Functional analysis of *A. borkumensis* genome revealed the presence of genes encoding proteins for polyhydroxyalkanoate (PHA) production (as shown by homology studies with other organisms). Therefore, according to the invention, it was shown that *A. borkumensis* is a PHA producing bacterium. Further amino acid sequence alignments of the proteins revealed low sequence homology with the proteins involved in PHA synthesis metabolism in other bacterial species (see FIG. 5, Table 1) suggesting a characteristic metabolic root of PHA production in *A. borkumensis*.

As mentioned above, a microorganism of the present invention may typically contain at least one modified gene encoding a protein interfering with PHA production, preferably a thioesterase, more preferably a thioesterase synthesizing 3-HAA encoding a protein involved in the metabolism of PHA synthesis. However, the invention provides also a nucleic acid sequence which constitutes a gene encoding a protein involved in the metabolism of polyhydroxyalkanoate(s) (PHA), wherein the gene has at least one modification causing excretion of polyhydroxyalkanoate(s) PHA, preferably long chain polyhydroxyalkanoates (PHA), produced by the microorganism of the present invention. Preferably, the modified nucleic acid sequence of the invention is based on a wild type gene selected from the group consisting of PHA synthase, PHB synthase, acyl-CoA transferase, enyol-CoA hydratase, reductase, thiolase and acyl-CoA thioesterase. On the other hand, the present invention provides a gene modified by at least one modification, preferably rendering the enzymatic activity of the encoded enzyme defective, whereby the gene is acyl-CoA thioesterase tesB-like, preferably acyl-CoA thioesterase tesB-like of *Alcanivorax borkumensis*, more preferably acyl-CoA thioesterase tesB-like of *Alcanivorax borkumensis* SK2 or homologues of this enzyme in other microorganisms, especially as shown by table 4 (FIG. 10).

An especially preferred microorganism of the present invention has been deposited according to the Budapest Treaty on the International Recognition of the Deposit of Microorganisms for the Purpose of Patent Procedure at Deutsche Sammlung von Mikroorganismen and Zellkulturen GmbH (DSMZ), Mascheroder Weg 1b, 38124 Braunschweig, Germany with the identification reference SK2 C9 mutant and the Accession Number DSM17483.

A particularly preferred embodiment relates to a nucleic acid sequence comprising or consisting of one of the nucleic acid sequences shown in FIGS. 11, 12, 16 and 18 to 25 (SEQ ID NOs: 1, 2, 6 and 8 to 15, respectively) or a functional fragment or variant thereof.

The nucleic acid sequence of the invention can be DNA comprising the coding sequence and eventually further sequences. The nucleic acid molecule can be double stranded or single stranded; single stranded RNA or DNA can be either the coding (sense) strand or the non-coding (antisense) strand. If desired, the nucleic acid sequence can include additional non-coding sequences such as non-coding 3'- and 5'-sequences (including regulatory sequences, for example). All nucleic acid sequences, unless designated otherwise, are written in the direction from the 5' end to the 3' end. The term "nucleic acid sequence" also includes a fragment or variant thereof as described below. Furthermore, the nucleic acid sequence of the invention can be fused to a nucleic acid sequence comprising or consisting of, for example, a marker sequence, a leader sequence or a nucleic acid sequence which encodes a polypeptide to assist, e.g., in isolation or purification of the polypeptide. Representative sequences include, but are not limited to those which encode a glutathione-S-transferase (GST) fusion protein, a poly-histidine (e.g., His6), hemagglutinin, HSV-Tag, for example.

The term "functional" fragment or variant of a nucleic acid sequence relates to a nucleic acid sequence of the invention which is able to constitute a typically modified gene encoding for a protein involved in the metabolism of PHA, or a gene, encoding for a protein, which interferes in the metabolism of the microorganism with the production of PHA, and/or encodes a biologically active (e.g., a protein involved in the metabolism of PHA, or a protein, which interferes in the metabolism of the microorganism with the production of PHA) polypeptide of the invention as described below.

Additionally, in the context of the present invention, nucleic acid sequences may be used herein, which encode a protein, which provides for deposition of PHA in the extracellular medium, wherein the protein competes with the synthesis of PHA by PHA-synthase in a microorganism. These nucleic acid sequences may thus be termed herein "dysfunctional" nucleic acid sequences. "Dysfunctional" nucleic acid sequences according to the invention may comprise native nucleic acid sequences according to FIGS. 16 and 18 to 25 (SEQ ID NOs: 6 and 8 to 15, respectively) or encode native polypeptides sequences according to FIGS. 17 and 26 to 33 (SEQ ID NOs: 7 and 16 to 23, respectively), wherein these sequences have been interrupted by transposon inserts (e.g. as exemplified in FIGS. 14 and 15, SEQ ID NOs: 4 and 5, respectively) as disclosed above for nucleic acid sequences and the corresponding genes. Furthermore, "dysfunctional" nucleic acid sequences according to the invention may comprises nucleic acid sequences according to FIGS. 11 and 12 (SEQ ID NOs: 1 and 2, respectively), which have been interrupted by transposon inserts.

The term "fragment" of a nucleic acid sequence is intended to encompass a portion of a nucleic acid sequence described herein which is from at least about 25 contiguous nucleotides to at least about 50 contiguous nucleotides, preferably at least about 60 contiguous nucleotides, more preferably at least about 120 contiguous nucleotides, more preferably at least about 180 contiguous nucleotides, more preferably at least about 250 contiguous nucleotides, more preferably at least about 410 contiguous nucleotides or longer in length. In this context, shorter fragments according to the invention are useful as probes and also as primer. Particularly preferred primers and probes selectively hybridize to the nucleic acid sequence encoding the polypeptides described herein. A primer is a fragment of a nucleic acid sequence which functions as an initiating substrate for enzymatic or synthetic elongation. A probe is a nucleic acid sequence which hybridizes with a nucleic acid sequence of the invention, a fragment or a complementary nucleic acid sequence thereof. Fragments which encode polypeptides according to the invention that retain function as described above are particularly useful.

Hybridization can be used herein to analyze whether a given fragment or gene corresponds to the microorganism of the invention and thus falls within the scope of the present invention. Hybridization describes a process in which a strand of a nucleic acid sequence joins with a complementary strand through base pairing. The conditions employed in the hybridization of two non-identical, but very similar, complementary nucleic acids varies with the degree of complementary of the two strands and the length of the strands. Such conditions and hybridization techniques are well known by a person skilled in the art and can be carried out following standard hybridization assays (see e.g., Sambrook J, Maniatis T (2001) supra). Consequently, all nucleic acid sequences which hybridize to the nucleic acid sequence or the functional fragments or functional variants thereof according to the invention are encompassed by the invention.

A variant of a nucleic acid sequence means a nucleic acid sequence which is derived from a nucleic acid sequence of the invention by addition, substitution, deletion or insertion of one or more nucleic acid(s) retaining the characteristic function of said nucleic acid sequence as described above. Such nucleic acid sequence can exhibit altered properties in some specific aspect (e.g. increased or decreased expression rate). Beside that, skilled artisans will recognize that the amino acids of polypeptides of the invention, as described below, can be encoded by a multitude of different nucleic acid triplets because most of the amino acids are encoded by more than one nucleic acid triplet due to the degeneracy of the genetic code. Because these alternative nucleic acid sequences would encode the same amino acid sequence, the present invention also comprises those alternate nucleic acid sequences.

A variant of a nucleic acid sequence according to the invention has substantial identity with the nucleic acid sequences described herein. Particularly preferred are nucleic acid sequences which have at least about 30%, preferably at least about 40%, more preferably at least about 50%, even more preferably at least about 60%, yet more preferably at least about 80%, still more preferably at least about 90%, and even more preferably at least about 95% identity with nucleic acid sequences described herein.

To determine the percent identity of two nucleic acid sequences in the above mentioned context, the sequences can be aligned for optimal comparison purposes (e.g., gaps can be introduced in the sequence of a first nucleic acid sequence). The nucleotides at corresponding nucleotide positions can then be compared. When a position in the first sequence is occupied by the same nucleotide as the corresponding position in the second sequence, then the molecules are identical at that position. The percent identity between two sequences is a function of the number of identical positions shared by the sequences. Therefore, the determination of percent identity of two sequences can be accomplished using a mathematical algorithm. A preferred, non-limiting example of a mathematical algorithm utilized for the comparison of two sequences is the algorithm of Karlin et al. (1993), PNAS USA, 90:5873-5877. Such algorithm is incorporated into the NBLAST program which can be used to identify sequences having the desired identity to nucleic acid sequences of the invention. To obtain gapped alignments for comparison purposes, Gapped BLAST can be utilized as described in Altschul et al. (1997), Nucleic Acids Res, 25:3389-3402. When utilizing BLAST and Gapped BLAST programs, the default parameters of the respective programs (e.g., NBLAST) can be used. The described method of determination of the percent identity of two can be also applied to amino acid sequences.

The production of fragments or variants of a nucleic acid sequence of the invention can be carried out following standard methods which are well known by a person skilled in the art (see e.g., Sambrook J, Maniatis T (2001) supra). In general, the preparation of such functional fragments or variants of a nucleic acid sequence can be achieved by modifying (altering) a DNA sequence which encodes a polypeptide of the invention and amplifying the DNA sequence with suitable means, e.g., by PCR technique. Those modifications (mutations) of the nucleic acid sequences may be generated by genetic engineering techniques as described above. The isolation of a functional fragment or functional variant of a nucleic acid sequence can be carried out using standard methods as screening methods (e.g., screening of a genomic DNA library) followed by sequencing or hybridization (with a suitable probe, e.g., derived by generating an oligonucleotide of desired sequence of the target nucleic acid) and purification procedures, if appropriate.

The present invention also encompasses gene products of the nucleic acid sequence of the invention. Gene products according to the invention not only relate to the transcripts accordingly RNA, preferably mRNA, but also to alleles, polypeptides or proteins or enzymes, particularly, in purified form. Preferably the gene product is a polypeptide encoded by a nucleic acid sequence of the invention. Preferably, the inventive polypeptide comprises one of the amino acid sequences shown in FIGS. 13, 17 and 26 to 33.

A "functional" polypeptide according to the invention means that the polypeptide can be used to produce deposited, e.g. excreted, PHA, preferably in combination with other polypeptides involved in the metabolism of PHA. Preferably an overproduction of PHA is also achieved by functional polypeptides of the PHA synthesis pathway. Methods for measuring and analyzing production, excretion and/or overproduction of substances, like PHA, are well known in the art (see e.g., Sambrook J, Maniatis T (2001) Molecular Cloning: A laboratory manual, Cold Spring Harbor Laboratory Press, Cold Spring Habor, N.Y.) and are also described by this invention, e.g. Examples 3 to 8, FIGS. 1, 3, 4 to 6). Without being limited thereto, "functional" polypeptides according to the invention may comprises native polypeptides sequences according to FIGS. 17 and 26 to 33.

Additionally, in the context of the present invention, polypeptides may be used herein, which provide for deposition of PHA in the extracellular medium, particularly by competing with the synthesis of PHA by PHA-synthase in a microorganism, and thus may be termed herein "dysfunctional" polypeptides, e.g. tesB-like proteins as defined herein. Such competition may occur, as explained above, due to thioesterases which act with a high specific activity on the cleavage of 3-hydroxyacyl-CoAs which forms the building block of PHA synthesis. These thioesterases allow to release free 3-HAAs. However, the conversion to 3-HAA is a reaction which competes with the synthesis of PHA by PHA-synthase, which acts on the same cellular intermediate (namely 3-hydroxyacyl-CoAs). As explained above, it was found according to the invention, that (i) the release of free 3-HAAs and the synthesis of PHA are interfering metabolic pathways and (ii) that functional knock-out of the specific thioesterase, herein termed tesB-like thioesterase, provides for deposition of PHA in the extracellular medium. "Dysfunctional" polypeptides according to the invention may comprises native polypeptides sequences according to FIGS. 17 and 26 to 33 (SEQ ID NOs: 7 and 16 to 23, respectively) or as encoded by nucleic acid sequences according to FIGS. 16 and 18 to 25, SEQ ID NOs: 6 and 8 to 15, respectively), wherein these sequences have been interrupted by transposon inserts (e.g. as exemplified in FIGS. 14 and 15, SEQ ID NOs: 4 and 5, respectively) as disclosed above for nucleic acid sequences and the corresponding genes. Furthermore, polypeptides according to the invention may comprises polypeptides sequences as encoded by the nucleic acid sequences according to FIGS. 11 and 12 (SEQ ID NOs: 1 and 2, respectively), which have been interrupted by transposon inserts.

The production of polypeptides of the invention is well known and can be carried out following a number of different standard methods which are well known by a person skilled in the art (see e.g., Sambrook J, Maniatis T (2001) supra), e.g., by solid phase peptide synthesis or recombinant methods. Both methods are described in U.S. Pat. No. 4,617,149, the entirety of which is herein incorporated by reference. The principles of solid phase chemical synthesis of polypeptides are well known in the art and are described by, e.g., Dugas H. and Penney C. (1981), Bioorganic Chemistry, pages 54-92. For examples, peptides may be synthesized by solid-phase methodology utilizing an Applied Biosystems 430A peptide synthesizer (commercially available from Applied Biosystems, Foster City, Calif.) and synthesis cycles supplied by Applied Biosystems. Essential protected amino acids, such as t-butoxycarbonyl-protected amino acids, and other reagents are commercially available from many chemical supply houses. The isolation of polypeptides of the invention can be carried out using standard methods like separation from the culture medium by centrifugation, filtration or chromatography and precipitation procedures (see, e.g., Sambrook J, Maniatis T (2001) supra).

The polypeptide(s) of the invention can also be fused to at least one second moiety. The at least second moiety can be an amino acid, oligopeptide or polypeptide and can be linked to the polypeptide of the invention at a suitable position, for example, the N-terminus, the C-terminus or internally. Linker sequences can be used to fuse the polypeptide of the invention with at least one other moiety/moieties. According to one embodiment of the invention, the linker sequences preferably form a flexible sequence of 5 to 50 residues, more preferably 5 to 15 residues. In a preferred embodiment the linker sequence contains at least 20%, more preferably at least 40% and even more preferably at least 50% Gly residues. Appropriate linker sequences can be easily selected and prepared by a person skilled in the art. Additional moieties may be linked to the inventive sequence, if desired. If the polypeptide is produced as a fusion protein, the fusion partner (e.g, HA, HSV-Tag, His6) can be used to facilitate purification and/or isolation. If desired, the fusion partner can then be removed from polypeptide of the invention (e.g., by proteolytic cleavage or other methods known in the art) at the end of the production process.

The invention also provides a vector comprising the nucleic acid sequence of the invention. The terms "construct", "recombinant construct" and "vector" are intended to have the same meaning and define a nucleotide sequence which comprises beside other sequences one or more nucleic acid sequences (or functional fragments or functional variants thereof) of the invention. A vector can be used, upon transformation into an appropriate cell (host cell) to cause expression of the nucleic acid. The vector may be a plasmid, a phage particle or simply a potential genomic insert. Once transformed into a suitable host, the vector may replicate and function independently of the host genome, or may, under suitable conditions, integrate into the genome itself.

The aforementioned term "other sequences" of a vector relates to the following: In general, a suitable vector includes an origin of replication, for example, Ori p, colE1 Ori, sequences which allow the inserted nucleic acid sequence to be expressed (transcribed and/or translated) and/or a selectable genetic marker including, e.g., a gene coding for a fluorescence protein, like GFP, or a gene which confer resistance to antibiotics, such as the p-lactamase gene from Tn3, the kanamycin-resistance gene from Tn903 or the chloramphenicol-resistance gene from Tn9.

The term "plasmid" means an extrachromosomal usually self-replicating genetic element. Plasmids are generally designated by a lower "p" preceded and/or followed by letters and numbers. The starting plasmids herein are either commercially available, publicly available on an unrestricted basis or can be constructed from available plasmids in accordance with the published procedures. In addition, equivalent plasmids to those described are known to a person skilled in the art. The starting plasmid employed to prepare a vector of the present invention may be isolated, for example, from the appropriate E. coli containing these plasmids using standard procedures such as cesium chloride DNA isolation.

A vector according to the invention encompasses a (recombinant) DNA cloning vector as well as a (recombinant) expression vector. Preferred vectors according to the invention are E. coli pBR322, XL-Blue MRF' and pBK-CMV, bacteriophage lambda etc. A DNA cloning vector refers to an autonomously replicating agent, including, but not limited to, plasmids and phages, comprising a DNA molecule to which one or more additional nucleic acid sequences of the invention have been added. An expression vector relates to any DNA cloning vector recombinant construct comprising a nucleic acid sequence of the invention operable linked to a suitable control sequence capable of effecting the expression and to control the transcription of the inserted nucleic acid sequence of the invention in a suitable host. Operable linked means that the nucleic acid sequence is linked to a control sequence in a manner which allows expression (e.g., transcription and/or translation) of the nucleic acid sequence. Transcription means the process whereby information contained in a nucleic acid sequence of DNA is transcribed to complementary RNA sequence.

Aforementioned control sequences are well known in the art and are selected to express the nucleic acid sequence of the invention and to control the transcription. Such control sequences include, but are not limited to a polyadenylation signal, a promoter (e.g., natural or synthetic promotor) or an enhancer to effect transcription, an optional operator sequence to control transcription, a locus control region or a silencer to allow a tissue-specific transcription, a sequence encoding suitable ribosome-binding sites on the mRNA, a sequence capable to stabilize the mRNA and sequences that control termination of transcription and translation. These control sequences can be modified, e.g., by deletion, addition, insertion or substitution of one or more nucleic acids, whereas saving their control function. Other suitable control sequences are well known in the art and are described, for example, in Goeddel (1990), Gene Expression Technology: Methods in Enzymology 185, Academic Press, San Diego, Calif.

Promoters for use in bacterial systems also will contain a Shine-Dalgarno sequence operably linked to the DNA encoding the desired polypeptides.

Useful expression vectors, for example, may consist of segments of chromosomal, non-chromosomal and synthetic DNA sequences such as various known variants of SV40 and known bacterial plasmids, e.g., plasmids from E. coli including col E1, pBK, pCR1, pBR322, pMb9, pUC 19 and their variants, wider host range plasmids, e.g., RP4, phage DNAs e.g., the numerous variants of phage lambda, e.g., NM989, and other DNA phages, e.g., M13 and filamentous single stranded DNA phages and vectors derived from combinations of plasmids and phage DNAs, such as plasmids which have been modified to employ phage DNA or other expression control sequences. Expression techniques using the expression vectors of the present invention are known in the art and are described generally, for example, in Sambrook J, Maniatis T (2001) supra.

Preferably, a vector of the invention, especially an expression vector, comprises a gene cluster comprising a modified gene as defined above, e.g. a gene having at least one modification in at least one gene encoding for a protein involved in the metabolism of polyhydroxyalkanoate(s) (PHA) or, preferably, in at least one gene encoding for a protein, which interferes in the metabolism of the microorganism with the production of PHA, wherein the at least one modification causes extracellular deposition, e.g. excretion, of polyhydroxyalkanoate(s) (PHA), preferably medium or long chain polyhydroxyalkanoate(s) (PHA), produced by the microorganism, preferably in/into the culture medium. Such an expression vector can be introduced in any suitable microorganism, as mentioned above, to generate an inventive microorganism producing and excreting PHA. Such gene cluster typically comprises all genes which are necessary or relevant in the metabolism of PHA. Consequently, also encompassed by the invention is an inventive microorganism comprising aforementioned (expression) vector which comprises said gene cluster.

The invention also provides a cell (also: host cell) comprising a vector or a nucleic acid (or a functional fragment, or a functional variant thereof) according to the invention. A cell (host cell) means a cell of any microorganism described herein which is useful according to the present invention). Furthermore, a cell or host cell means a cell which has the capacity to act as a host and expression vehicle for a nucleic acid or a vector according to the present invention. Preferably, the cell is a prokaryotic cell. Cells comprising (for example, as a result of transformation, transfection or tranduction) a vector or nucleic acid as described herein include, but are not limited to, bacterial cells (e.g., A. borkumensis, E. coli). The choice of a particular cell depends to some extent on the particular expression vector used to drive expression of the nucleic acids of the present invention.

A vector can be introduced into a cell (host cell) using any suitable method (e.g., transformation, electroporation, transfection using calcium chloride, rubidium chloride, calcium phosphate, DEAE dextran or other substances, microprojectile bombardment, lipofection, infection or transduction). Transformation relates to the introduction of DNA (nucleic acid sequence) into an organism so that the DNA is replicable, either as an extrachromosomal element or by chromosomal integration. Methods of transforming bacterial hosts are well known in the art. Numerous methods, such as nuclear injection, protoplast fusion or by calcium treatment are summarized in Sambrook J, Maniatis T (2001) supra. Transfection refers to the taking up of a vector by a cell (host cell) whether or not any coding sequences are in fact expressed. Successful transfection is generally recognized when any indication or the operation or this vector occurs within the cell.

Another aspect of the invention relates to a method for producing polyhydroxyalkanoates (PHA) comprising the following steps:

cultivating a microorganism or a cell of the invention and
recovering polyhydroxyalkanoates (PHA) from the culture medium.

Standard methods for cultivating a microorganism or a cell under suitable conditions are well known in the art. See, e.g. below under Examples, Materials and also Sambrook J, Maniatis T (2001) supra.

PHA can be isolated from the culture medium by conventional procedures including separating the cells from the medium by centrifugation or filtration, precipitating or filtrating the components (PHA) of the supernatant, followed by purification, e.g., by chromatographic procedures. e.g., ion exchange chromatography, affinity chromatography or similar art recognized procedures (see also Example 4).

Another aspect of the invention relates to the use of a microorganism, a polypeptide, a nucleic acid, a vector and/or a cell of the invention for the production and deposition, e.g. excretion, and/or overproduction of polyhydroxyalkanoates (PHA), especially medium and/or long chain polyhydroxyalkanoates (PHA).

In summary, the invention relates to a genetically engineered microorganism having at least one modification in at least one gene encoding for a protein involved in the metabolism of polyhydroxyalkanoate(s) (PHA) or, preferably, in at least one gene encoding for a protein, which interferes in the metabolism of the microorganism with the production of PHA, wherein the at least one modification causes extracellular deposition, e.g. excretion, of polyhydroxyalkanoate(s) (PHA), preferably medium and/or long chain polyhydroxyalkanoate(s) (PHA), produced by the microorganism, preferably in/into the culture medium. Transposon mutagenesis, based on miniTn5 Str/Sp element (see Example 1) as well as miniTn5 Km element, was used for introducing the at least one modification into at least one gene encoding for a protein, which interferes in the metabolism of the microorganism with the production of PHA. Subsequently, a screening for miniTn5 mutants deficient in biofilm formation, as measured by a deficiency of attachment of mutant cells to plastic surfaces, was performed (see Example 2). A mutant (hereinafter indicated with "C9" or "C9 mutant") was isolated showing a clear deficiency in biofilm formation due to excessive production of secreted polymeric material, later identified as PHA (see Example 4).

According to the invention production and deposition, e.g. excretion, of PHA, by applying an inventive genetically engineered microorganism, e.g., as derived from *A. borkumensis*, as well as intracellular PHA accumulation in form of granula by these microorganisms, especially by *A. borkumensis*, was confirmed by chemical analysis. It has been analyzed that by use of these genetically engineered microorganism microorganisms, especially *A. borkumensis*, grown e.g., on octadecane under conditions of a high C to N ratio, a mixture of different PHA (hydroxyhexanoate, hydroxyoctanoate, hydroxydecanoate, hydroxydodecanoate) can be produced in form of intracellular granula as storage material. Beyond that, the isolation and characterization of genetically engineered microorganisms having at least one modification, particularly in at least one gene encoding for a protein, which interferes in the metabolism of the microorganism with the production of PHA, wherein the at least one modification causes extracellular deposition, was achieved. This invention will bypass the problem of costly recovery of intracellular produced PHA and will lead to a higher yield of PHA.

The following Figures and Examples are thought to illustrate the invention. They should not be constructed to limit the scope of the invention thereon. All references cited by the disclosure of the present application are hereby incorporated in their entirety by reference.

In another embodiment enzymes are provided, which provide for production of 3-HAA as defined above. Such enzymes include, without being limited thereto, any enzymes derived from *Alkanivorax, Pseudomonas putida, Pseudomonas aeruginosa, Pseudomonas syringae, Pseudomonas fluorescens, Acinetobacter* sp., *Caulobacter crescentus* the thioesterase and being capable of producing 3-HAA.

The present invention furthermore provides the use of these enzymes, which provide for production of 3-HAA as defined above, and/or their encoding nucleic acids, for producing PHA, preferably medium or long chain polyhydroxyalkanoate(s) PHA. Such enzymes may be transfected into microorganisms as outlined above, e.g. as a vector or as a (naked)nucleic acid, or in the form of a protein, e.g. as a fusion with cell penetrating peptides, using methods, known in the art.

FIGURES

FIG. 1 shows PHA production in wild type *A. borkumensis* SK2 (hereinafter also referred to as "SK2" or "SK2 wild type") and mutant *A. borkumensis* SK2 (hereinafter also referred to as "C9 mutant") on either 2% pyruvate or 1.5% octadecane as carbon source. Cells and corresponding supernatants were checked for PHA content, indicated in g/l. The production of Pha was in the following order: C9 mutant supernatant octadecane>C9 mutant supernatant pyruvate>SK2 wild type cells+supernatant octadecane>SK2 wild type cells+supernatant pyruvate. The amount of Pha isolated from C9 mutant cells grown on either pyruvate or octadecane was too low for quantification (third and fifth probe in the diagram). C9 mutants grown on pyruvate produced almost 10 times more PHA than SK2 wild type grown on pyruvate. Moreover, C9 mutants grown on octadecane produced almost 10 times more PHA than SK2 wild type grown on octadecane. Therefore, according to the invention, a genetically engineered microorganism is provided that deposits, e.g. excretes, and overproduces PHA.

FIG. 2 shows electron microscopic images of ultrathin sections of *A. borkumensis* SK2 strain. Cells were cultivated in ONR7a containing 1.5% (w/v) octadecane and 0.27 g/l of $NH_4Cl$ (storage conditions) and harvested in stationary phase of growth. These ultrathin sections prepared from the cells confirmed presence of intracellular granula.

FIG. 3 shows scanning electron microscopy images (FIGS. 3A and 3B) and electron microscopic images (FIGS. 3C and D) of SK2 wild type cells and C9 mutant cells, grown on *Permanox* hydrophobic slides covered with octadecane. FIGS. 3A and 3C show results for SK2 wild type cells. FIGS. 3B and 3D show results for C9 mutant cells confirming the production of extracellular PHA and the excretion of PHA into the surrounding culture medium, respectively. Although both images contain rod-shaped cells, it is obvious that C9 mutant cells are embedded in extracellular network of some deposited, e.g. excreted material, whereas the SK2 wild type cells are not. These results support the hypothesis that C9 mutant strain is involved in the production of some polymeric extracellular material proved by chemical analysis to be PHA. Further EM images of shadow casting technique of SK2 wild type and C9 mutant cells grown on octadecane in storage conditions provided additional support for the hypothesis that the PHA produced by the mutant strain is deposited, e.g. excreted in the culture medium. The EM pictures for the shadow-casted cells of the C9 mutant strain revealed the perforations on the surface of the C9 mutant cells which are probably involved in excretion of intracellular produced PHA.

FIG. 4 shows in a diagram the comparison of growth characteristics of C9 mutants and SK2 wild type. As can be seen. C9 mutant did have growth characteristics comparable with SK2 wild type when pyruvate was used as a carbon source. In case of octadecane C9 mutant even showed better growth compared with SK2 wild type. SK2 wild type had some deficiency in growth on octadecane in these conditions compared with C9 mutant. The explanation for this could be that the high intracellular PHA content inhibits cell division of SK2 wild type. Cell counts also show the domination in growth on octadecane for C9 mutant (data not shown) which under the conditions of high C/N ratio releases the synthesized PHA into the medium and is still able for cell division. In conclusion, the microorganism according to the invention is absolutely usable for biotechnological, commercial and industrial purposes.

FIG. 5 shows Table 1 representing the results of in silico analysis of sequences data of the genes for polyhydroxyalkanoate production and mobilization in *A. borkumensis* SK2.

FIG. 6 shows Table 2 representing the analysis of PHA and its composition.

To confirm that the substance deposited, e.g. excreted by wild type *A. borkumensis* SK2 (hereinafter also referred to as "SK2" or "SK2 wild type") and mutant *A. borkumensis* SK2 (hereinafter also referred to as "C9 mutant") is in fact PHA, further chemical analysis were conducted and revealed the presence of PHA. The cells were grown on either pyruvate or octadecane as carbon and energy source in PHA accumulating conditions (PHA storage conditions), i.e., high C/N ratio (C:N ratio 100:1) and were separated from the medium. Cells and corresponding supernatants were checked for PHA content. Pha from C9 mutant and SK2 wild type cells or supernatants were purified by sodium hypochlorite digestion and subsequent solvent extraction with acetone/diethylether (Solaiman et al., 1999). The production of Pha was in the following order:

C9 mutant supernatant octadecane>C9 mutant supernatant pyruvate>SK2 wild type cells+supernatant octadecane>SK2 wild type cells+supernatant pyruvate.

Figure 1:
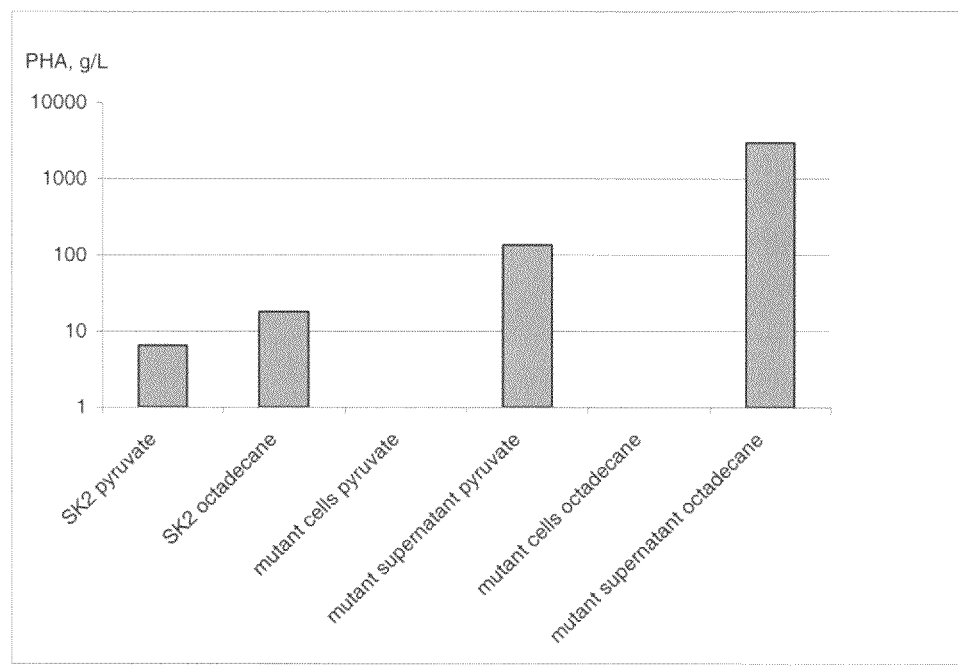

The amount of Pha isolated from C9 mutant cells grown on either pyruvate or octadecane was too low for quantification (see also FIG. 1). SK2 wild type cells grown on octadecane produced almost 3 times more PHA compared with the cells grown on pyruvate (18 mg/l vs. 6.5 mg/l). The amount of PHA isolated from C9 mutant supernatant grown on octadecane produced 22 times more PHA compared with the cells grown on pyruvate (2,960 mg/l vs. 134 mg/l).

Figure 2:
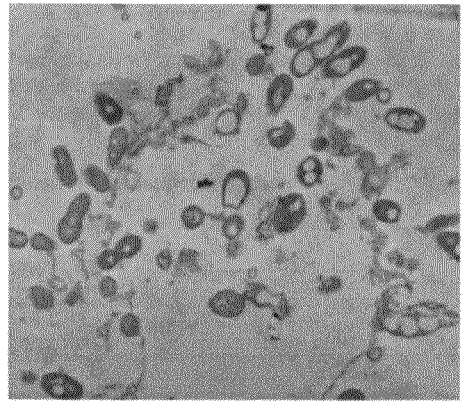
Figure 3:
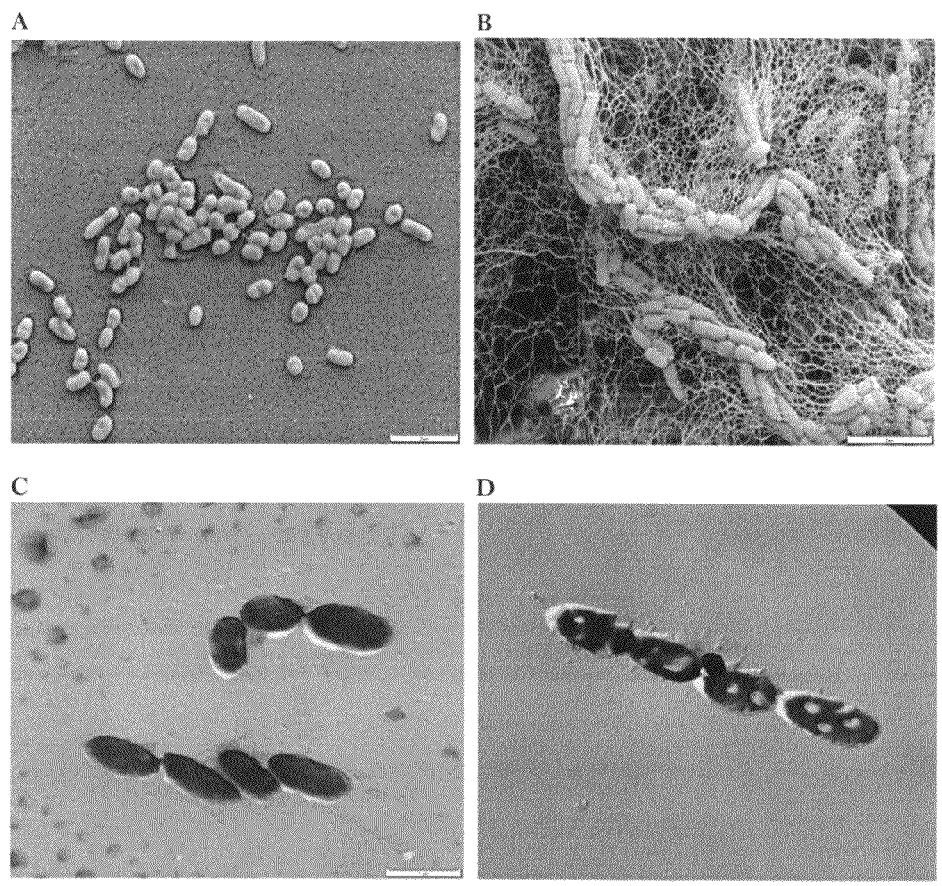
Figure 4:
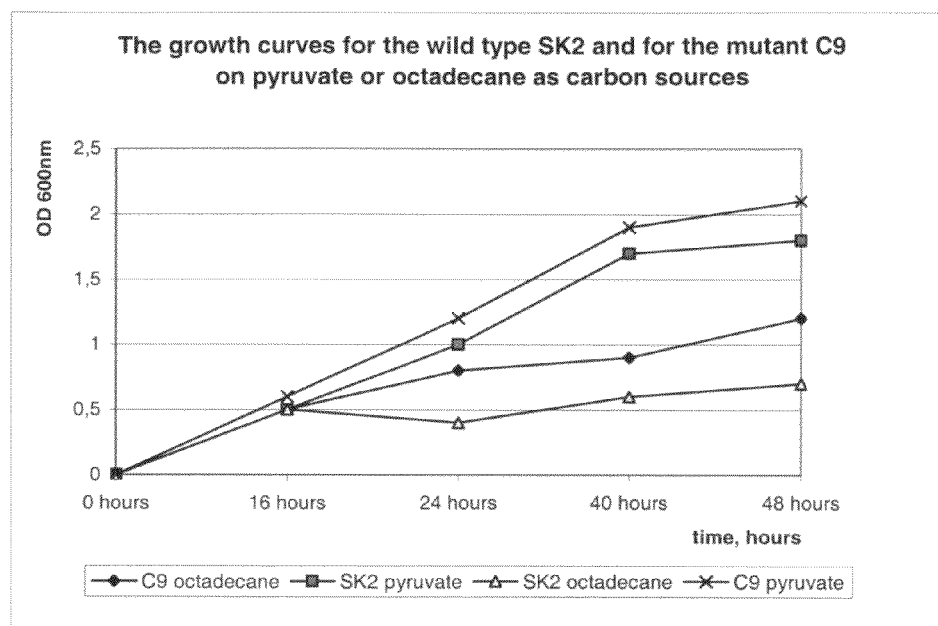

As shown in Table 2, the amount of PHA produced by SK2 wild type was rather low (6.5 mg/l on pyruvate and 18 mg/l on octadecane) and was dependent on the carbon source with more PHA produced on alkanes. The PHA produced by SK2 wild type was consisting of hydroxyhexanoate (C6), hydroxyoctanoate (C8), hydroxydecanoate (C10) and hydroxydodecanoate (C12) with hydroxydecanoate as the dominant monomer compound. Thus, it was shown despite previous findings (Yakimov et al. 1998) that under conditions of high C/N ratio *Alcanivorax borkumensis* SK2 strain produces a mixture of polyhydroxyalkanoates mostly from alkanes. Moreover, later growth of *A. borkumenis* SK2 under high C/N ratio indeed showed granula visible under light microscope consisting of PHA (see also FIG. 2).

Table 2 also shows that PHA of SK2 wild type were accumulated inside the cells (no extracellular production), whereas the all PHA produced by C9 mutant was deposited, e.g. excreted to the medium cells (extracellular production). The monomer repeat-unit composition and molecular mass of the polymer (from all the batches) were determined by gas chromatography/mass spectroscopic analysis and gel permeation chromatography, respectively.

FIG. 7 shows Table 3 representing the molecular weights of PHA from *A. borkumensis*. Results for C9 mutant supernatants growing on pyruvate and octadecane and for SK2 wild type growing on pyruvate and octadecane are shown. The *A. borkumensis* SK2 polymer had repeat unit composition ranging from C6 to C12. The molecular weight of the polymers varied from 180,000 to 540,000 Da (up to 2500 monomers per molecule). This corresponds to a monomer repetition of 1,027 to 2,246 units, depending on the polymer. Similar composition and/or molecular weight was observed for C9 mutant, although the PHA molecular weights of the components were slightly lower in SK2 wild type cells. The molecular weight of the monomers also was not dependent on the carbon source. These data strongly suggest that the mutation affected the way of PHA production, but not the composition of the produced polymer.

Figure 8:
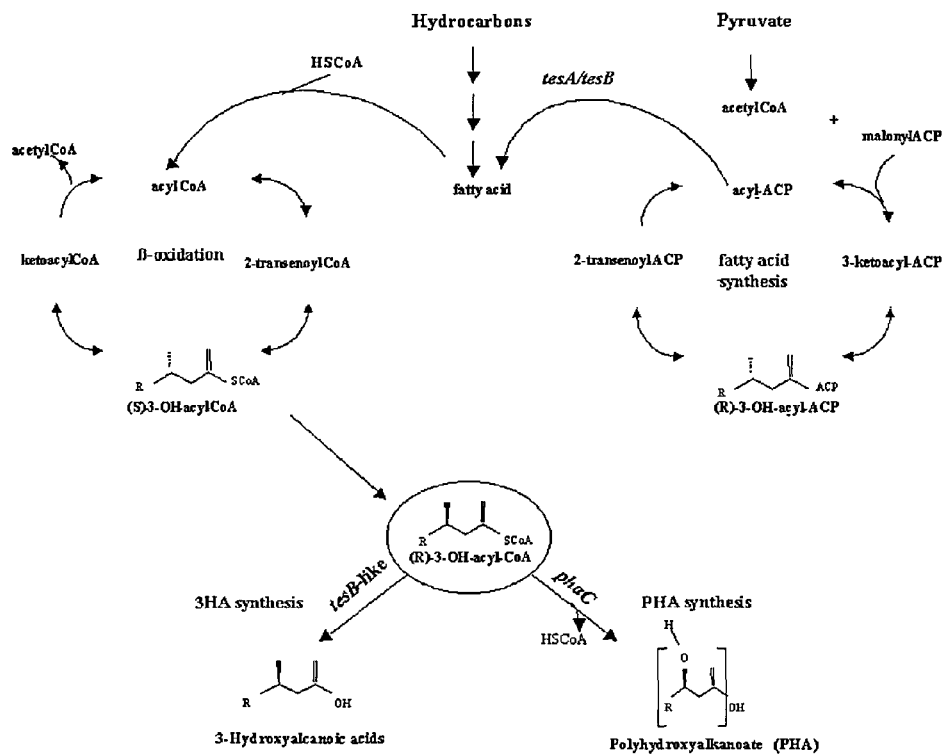

FIG. 8 shows a scheme of the hypothetical pathway of PHA biosynthesis in *A. borkumensis* SK2 grown on hydrocarbons/pyruvate (Modified version of Klinke et al. 1999 Hypothetical pathway of MCL PHA biosynthesis of PHA polymerase- and thioesterase I-containing *E. coli* JMU193 grown on gluconate). Hydrocarbons are degraded via terminal oxidation step by consequent action of a monooxygenase, alcohol dehydrogenase and aldehyde dehydrogenase resulting in free fatty acids which are activated by acyl-CoA synthase and enter b-oxidation in form of acyl-CoA. The (S)-3-OH-acyl-CoA produced in beta oxidation are isomerised into (R)-3-OH-acyl-CoAs by action of an isomerase. Pyruvate enters fatty acid biosynthesis in form of acetyl-CoA. Acyl-ACP produced in fatty acid biosynthesis is converted to free fatty acids by action of tesA and tesB. Tree fatty acids produced in fatty acid biosynthesis are activated by acyl-CoA synthase and entered beta-oxidation cycle. (R)-3-OH-acyl-CoAs produced in beta-oxidation are used for biosynthesis for either 3-hydroxyalkanoic acids (3-HAA) via action of tesB-like acyl-CoA thioesterase and/or polyhydroxyalkanoate acids (PHA) via action of phaC synthase. The mutation in the tesB-like acyl-CoA thioesterase abolishes production of 3-HAA and results in uncontrolled production of PHA.

Thus, in other words, according to the invention, the mutation of tesB-like gene abolishing release of free 3-HAA from 3-HAA-CoA, would contribute to increasing the pool of the PHA precursor 3-hydroxyacyl-CoA, leading to uncontrolled PHA formation and its following excretion.

FIG. 9 shows the operon structure of the two genes tesB-like and "putative acetyltransferase" forming a single operon.

The determination of the site of insertion of the transposon (see Example 1) revealed that mini-Tn5 is inserted in acyl-CoA thioesterase tesB-like gene (Abo__1044), which is one of the genes which encodes a protein which interferes with metabolism/production/synthesis of PHA, and likely to disrupt function of the gene, thus inactivating the gene. The tesB-like gene is followed by a downstream 1-acyl-sn-glycerol-3-phosphate acyltransferase "putative acetyltransferase" gene (Abo__1045). The ORF of "putative acetyltransferase" gene comprises 645 bp, exhibiting an overlap of 3 bp with the last codon of the preceding ORF of tesB-like gene and is predicted to encode a 214-amino-acid protein with a predicted molecular mass of 23.7 kDa. TesB-like gene and "putative acetyltransferase" gene are arranged in one operon as shown in FIG. 9.

To assess that the PHA excretion and overproduction phenotype, as described herein, was the result of the modification (mutation) in a gene encoding a protein which interferes with metabolism/production/synthesis of PHA, especially tesB-like acyl-CoA thioesterase gene, and to estimate the possibility of polar effect of the transposon mutation on the downstream gene, a site-directed mutant of the downstream gene was constructed and its phenotype compared with C9 mutant (see Example 3). To construct the knockout mutant the wild type copy of this gene was amplified and cloned in a vector that does not replicate in *A. borkumensis*. A Str resistance cassette was inserted into a unique site inside of this gene and the resulted construct was used to replace the wild type copy of the gene. The results were confirmed by light microscopy and chemical analysis of the culture medium (data not shown). They showed that the knockout mutant was deposited, e.g. excreted PHA in the medium which means that the mini-Tn5 insertion had polar effect on "putative acetyltransferase" gene. Therefore, taking into account the known positive contribution of tesB-like into PHA production, the PHA excretion and overproduction phenotype can beside tesB-like inactivation also be caused by a polar effect of the Tn-5 insertion on the downstream "putative acetyltransferase" gene.

FIG. 10 represents Table 4 showing acyl-CoA thioesterase proteins of several closely related gram-negative bacteria encoded by genes homologous of the tesB-like gene of *Alcanivorax borkumensis* SK2 (Abo_1044). These data are results of corresponding homology searches (BLAST searches) of putative acyl-CoA thioesterase proteins. As can be seen from Table 4 the tesB-like protein nominated differently, namely as putative acyl-CoA thioesterase II, hypothetical protein or tesB-like thioesterase. Bacteria of these searches were the species *Pseudomonas putida* KT2440 (SEQ ID NO: 8), *Pseudomonas aeruginosa* PA01 (SEQ ID NO: 9), *Pseudomonas syringae* pv B728a (SEQ ID NO: 10), *Pseudomonas fluorescens* PfO-1 (SEQ ID NO: 11), *Idiomarina loihiensis* L2TR (SEQ ID NO: 12), *Acinetobacter* sp. ADP1 (SEQ ID NO: 13) and *Caulobacter crescentus* CB15 (SEQ ID NO: 14). However, it is to be understood that the terms "tesB-like", "tesB-like gene" and/or "tesB-like protein" and description thereof is intended to relate to all these mentioned different nominations. The proteins presented in Table 4 show a high homology to the tesB-like gene of *A. borkumensis* SK2 (Abo_1044).

FIG. 11 shows nucleic acid sequences of the two genes tesB-like (Abo_1044). (underlined) and "putative acetyltransferase" (Abo_1045) forming a single operon (SEQ ID NO: 1). The first line is the region upstream from the tesB-like gene. The start codon of the tesB-like gene is atg and marked in bold letters. The Tn5 insertion took place at position 527 within tesB-like gene and marked with II. Downstream from the tesB-like gene is the "putative acetyltransferase" gene. There is overlap in 3 bp of the end of tesB-like (Abo_1044), and the start site of "putative acetyltransferase" (Abo_1045).

FIG. 12 shows the nucleic acid sequence of tesB-like of *A. borkumensis* (SEQ ID NO: 2). The Tn5 insertion took place at position 557 and is indicated with II. Start and stop codons are marked in bold letters.

FIG. 13 shows the amino acid sequence of tesB-like of *A. borkumensis* (SEQ ID NO: 3)

FIG. 14 shows the nucleic acid sequence of miniTn5 Km element (SEQ ID NO: 4)

FIG. 15 shows the amino acid sequence of neomycin phosphotransferase responsible for neomycin and kanamycin resistance (SEQ ID NO: 5).

FIG. 16 shows the nucleic acid sequence of "putative acetyltransferase" of *A. borkumensis* (SEQ ID NO: 6). Start and stop codons are marked in bold letters.

FIG. 17 shows the amino acid sequence of "putative acetyltransferase" of *A. borkumensis* SE ID NO: 7).

FIG. 18 shows the nucleic acid sequence of putative acyl-CoA thioesterase II of *Pseudomonas putida* KT2440 (SEQ ID NO: 8).

FIG. 19 shows the nucleic acid sequence of hypothetical protein PA2871 of *Pseudomonas aeruginosa* PAO (SEQ ID NO: 9).

FIG. 20 shows the nucleic acid sequence of acyl-CoA thioesterase II, putative, of *Pseudomonas syringae* pv B728a (SEQ ID NO: 10).

FIG. 21 shows the nucleic acid sequence of acyl-CoA thioesterase of *Pseudomonas fluorescens* PfO-1 (SEQ ID NO: 11).

FIG. 22 shows the nucleic acid sequence of tesB-like acyl-CoA thioesterase of *Idiomarina loihiensis* L2TR (SEQ ID NO: 12).

FIG. 23 shows the nucleic acid sequence of putative acyl-CoA thioesterase II of *Acinetobacter* sp. ADP1 (SEQ ID NO: 13).

FIG. 24 shows the nucleic acid sequence of hypothetical protein CC2472 of *Caulobacter crescentus* CB15 (SEQ ID NO: 14).

FIG. 25 shows the nucleic acid sequence of hypothetical protein ELI0992 of *Erythrobacter litoralis* HTCC2594 (SEQ ID NO: 15).

FIG. 26 shows the amino acid sequence of putative acyl-CoA thioesterase II of *Pseudomonas putida* KT2440 (SEQ ID NO: 16).

FIG. 27 shows the amino acid sequence of hypothetical protein PA2871 of *Pseudomonas aeruginosa* PA01 (SEQ ID NO: 17).

FIG. 28 shows the amino acid sequence of acyl-CoA thioesterase II, putative, of *Pseudomonas syringae* pv B728a (SEQ ID NO: 18).

FIG. 29 shows the amino acid sequence of acyl-CoA thioesterase of *Pseudomonas fluorescens* PfO-1 (SEQ ID NO: 19).

FIG. 30 shows the amino acid sequence of tesB-like acyl-CoA thioesterase of *Idiomarina loihiensis* L2TR (SEQ ID NO: 20).

FIG. 31 shows the amino acid sequence of putative acyl-CoA thioesterase II of *Acinetobacter* sp. ADP1 (SEQ ID NO: 21).

FIG. 32 shows the amino acid sequence of hypothetical protein CC2472 of *Caulobacter crescentus* CB15 (SEQ ID NO: 22).

FIG. 33 shows the amino acid sequence of hypothetical protein ELI0992 of *Erythrobacter litoralis* HTCC2594 (SEQ ID NO: 23).

EXAMPLES

Materials

Bacterial Strains, Media and Growth Conditions

*A. borkumensis* SK2 was used as the wild type for all experiments. The bacteria were grown at 30° C. in modified ONR7a medium (Yakimov et al 1998) where 0.27 g/l of $NH_4Cl$ was used as the source of nitrogen instead of $KNO_3$. Pyruvate (2%) or octadecane (1.5%) were used as a carbon and energy source.

*E. coli* was grown at 37° C. in Luria-Bertani medium supplemented with streptomycin (50 µg/ml), chloramphenicol (12.5 µg/ml), kanamycin (50 µg/ml), nalidixic acid (10 µg/ml) as necessary. Plasmids were introduced into *A. borkumensis* by conjugation with *E. coli* strain S17-1.

Example 1

Mini-Tn5 Mutagenesis

Transposon mutagenesis was based on miniTn5 Str/Sp element (and miniTn5 Km element) developed by de Lorenzo et al (1998). *A. borkumensis* SK2 was grown at 30° C. on ONR7a media till stationary phase of growth, the cells were centrifuged. The donor and helper cultures of *E. coli* were grown overnight at 37° C. on LB with either streptomycin or chloramphenicol respectively, washed with fresh LB and centrifuged. The pellets of *A. borkumensis* and *E. coli* donor and helper strains were mixed in proportion 4:1:1 and placed on a membrane filter on a plate with LB agar and salts ($Na_2HPO_4.2H_2O$, 0.45 g/l; $NaNO_3$, 2.5 g/l; NaCl, 11.5 g/l; KCl, 0.38 g/l; $CaCl_2.2H_2O$, 0.7 g/l) and 2% pyruvate as carbon and energy source. The plate was incubated for 24 hours at 30° C. The cells were then washed with 10 mM $MgSO_4$ and the transconjugants were selected on ONR7a with nalidixic acid and streptomycin.

mini-Tn5 insertion sites of the strains were determined by inverse PCR as described previously (Ochman et al 1988). Shortly, total DNA of mutants was isolated and digested with ClaI which does not cut mini-Tn5 element. The resulted DNA fragments were circularised and the flanking regions of the inserted mini-Tn5 were amplified with two primers: OTR End (GGC CGC ACT TGT GTA TAA GAG TCA G) (SEQ ID NO: 24) and 1TR End (GCGGCC AGA TCT GAT CAA GAG ACA G) (SEQ ID NO: 25). The conditions for the PCR were: 94° C. for 1.5 min; 48° C. for 1 min; 70° C. for 4 min, 30 cycles. The PCR products were gel purified and used for automate DNA sequencing with BigDye terminators on an AB1 Prism 377 sequencer (AP Biosystems). To determine the precise site of transposon mutation for the tesB-/ike mutant we designed primers which would read the flanking regions of the disrupted gene: 1086F (ITA CTG GCT TCG CAG GAA TGG) (SEQ ID NO: 26) and IntSM160 (CTTGGC ACC CAG CAT GCG CGA GCA GG9) (SEQ ID NO: 27).

Example 2

Biofilm Formation Assay

In order to screen for mini-Tn5 mutants defective in biofilm formation, an assay described by O'Toole and Kolter (1998) was employed. This assay scores the ability of bacterial cells to adhere to the wells of 96-well microtitre dishes made of polyvinylchloride (PVC) plastic. The ONR7A medium (100 µl/well) was inoculated using replicator device. After inoculation, plates were incubated at 30° C. for 48 h, then 25 µl of a 1% solution of crystal violet (CV) was added to each well (this dye stains the cells but not the PVC), the plates were incubated at room temperature for approximately 15 min, rinsed thoroughly and repeatedly with water and scored for the formation of a biofilm.

Biofilm formation was quantified by the addition of 2×200 µl of 95% ethanol to each CV-stained microtitre dish well. CV-stained biofilm was solubilized in 200 µl of 95% ethanol, of which 125 ml were transferred to a new polysterene microtitre dish, and the adsorbance was determined with a plate reader at 600 nm (series 700 microplate reader; Cambridge Technology).

Example 3

Site-Directed Mutagenesis of "Putative Acetyltransferase" Gene

To analyze, if the phenotype observed with strain C9 was the result of tesB-like inactivation or of polar effect of the mini-transposon mutation on the downstream gene, a targeted "putative acetyltransferase" mutant was constructed. A 769 bp fragment of the downstream "putative acetyltransferase" gene was amplified from *A. borkumensis* SK2 DNA with primers 1087F: (CAGTGATGGCTATGGTCAAAG) (SEQ ID NO: 28) and 1087R: (CTTTGATCAGTCCGGCAAAAC) (SEQ ID NO: 29) and cloned into pCR 2.1 TOPO Cloning vector (Invitrogen) containing ampicillin resistance gene for counterselection. A Str-resistance cassette was excised from Tn5 Str/Sp plasmid (de Lorenzo et al., 1998) and inserted into the unique site inside of the gene. The non-functional "putative acetyltransferase" gene was then re-introduced into *A. borkumensis* SK2 genome by homologous recombination via conjugation. To confirm loss of vector associated DNA $Str^R$ colonies were then plated in parallel on ONR7A agar containing streptomycin, nalidixic acid and ONT7A agar containing ampicillin to identify isolates that had lost the $Amp^R$ marker associated with the TopoCloning vector. The growth characteristics and PHA accumulation of the knockout mutant were measured and compared with the mini-Tn5 mutant and the wild type.

Example 4

Chemical Analysis of PHA

To analyze the PHA released into the medium by the wild type *A. borkumensis* SK2 and by the mutant strain, the bacteria were cultured in ONR7a medium containing either 2% of pyruvate or 1.5% octadecane as carbon sources (storage conditions). The bacteria were incubated in a rotary shaker (100 rpm) at 30° C. until late stationary phase of growth. The bacteria were harvested by centrifugation (60' 12,000) and the supernatant and the pellet were collected separately, lyophilized and used for the subsequent chemical analysis of PHA.

Example 5

PHA Quantification

Aliquots of the cells and of the supernatant were washed with ice-cold water and dried overnight at 80° C. under vacuum. Polyhydroxyalkanoates (PHA) were purified from the cells by sodium hypochlorite digestion and subsequent solvent extraction with acetone/diethylether (Solamain et al., 1999).

Example 6

Gas Chromatography/Mass Spectroscopy

To determine the PHA composition, approximately 2 mg of PHA were let to react in a small flask with a mixture containing chloroforms:methanol:sulphuric acid (1:0.85:0.15 ml) for 2 h at 100° C. in thermostatically regulated bath. This method degrades PHA by methanolysis to its constituent β-hydroxycarboxylic acid methyl esters (FAME). After the reaction, 0.5 ml of destilled water was added and the tube was shaken for 1 min. After phase separation, the organic phase was removed, transferred into a vial and used for analysis. FAMEs were analyzed with gas chromatograph-mass spectrometer (GC/MS, model Varian 3400CX, Varian Chromatography Systems, Sugar Land, Tex., and VG Autospec spectrometer), equipped with a 30 m×0.25 mm HP-5 (5% diphenyl and 95% dimethylpolysiloxane) fused silica capillary column; flow rate 1 ml/min; sample input temperature to 230° C. at a rate of 8° C./min; interface temperature 250° C.; ion source temperature 175° C.; electron impact mode 70 eV; scanning from 45 to 450 amu at 0.5 s/scan. The degree of purity of the PHA samples taken for investigation was up to 99.5%. No trace amounts of proteins, carbohydrates and lipids were registered in them. See data in Table 1.

Example 7

Gel Permeation Chromatography

The samples of Example 6 were analyzed in a HPLC system with a Spectra-Physics pump and an Aminex HPX-87H column (Bio-Rad, Hercules, Calif.) under the following conditions: column temperature, 50° C.; gradient, isocratic; mobile phase, 5 mM sulfuric acid; flow rate, 0.5 ml/min; detector, light scattering. See data in Table 2.

Example 8

Electron Microscopy

Cells were cultivated in ONR7a containing 1.5% (w/v) octadecane and $NH_4Cl$ (storage conditions) and were harvested in the stationary phase of growth. Cells for scanning electron microscopy were grown in the same conditions with the only difference that octadecane was embedded on *Permanox* cell culture slides (Nalge Nunc). The cells were shadow-casted according to Golyshina et al. (2000), embedding and ultrathin sections were done as described by Yakimov et al. (1998) and scanning electron microscopy was performed as described by Lünsdorf et al. (2001).

REFERENCES

Abe et al. 1994. Int. J. Biol. Macromol, 16: 115-19;
Amos & McInerey, 1991, Arch. Microbiol. 155: 103-06
Bagdasarian, M., R. Lurz, B. Ruckert, F. C. H. Franklin, M. M. Bagdasarian, J. Frey, and K. N. Timmis. 1981. Gene 16:237-247.
Brandl et al., 1989, Int. J. Biol. Macromol. 11:49-55
Cho, H., and J. E. Cronan, Jr. 1995. J. Biol. Chem. 270:4216-4219.
Choi J., Lee., S. Y. 1997. Bioprocess Eng. 17: 335-342.
Cooper, C. L., Jackowski, S., and Rock C. O. 1987. J. Bacteriology, February, p. 605-611.
Cronan, J. E., Jr. 1968. J. Bacteriol. 95:2054-2061.
de Lorenzo V, Herrero M, Jakubzik U, Timmis K N. 1990. J Bacteriology November; 172(11):6568-72.
deSmet et al. 1983. J. Bacteriol. 154: 870-78
Harayama, S., Kishira, H., Kasai, Y., and Shutsubo, K. 1999. J. Mol. Microbiol. Biotechnol. 1: 63-70.
Hocking, P. J. & Marchessault, R. H. 1994. Biopolyesters. Regulation of phasin and granule formation *Chemistry and Technology of Biodegradable Polymers*, pp. 48-96. Edited by G. J. L. Griffin. London: Chapman & Hall.
Holmes, P. A., Lim, G. B. 1990. Separation process. U.S. Pat. No. 4,910,145.
Hrabak, O. 1992. FEMS Microbiol. Rev. 103:251-256.
Huijberts, G. N. M., T. C. de Rijk, P. de Waard, and G. Eggink. 1995. J. Bacteriol. 176: 1661-1666
Huijberts, G. N. M., G. Eggink, P. de Waard, G. W. Huisman, and B. Witholt. 1992. Appl. Environ. Microbiol. 58:536-544.
Golyshina, O. V., Pivovarova, T. A., Karavaiko, G-I., Kondrat'eva, T. F., Moore, E. R. B., Abraham, W.-R., Lünsdorf, H., Timmis, K. N., Yakimov, M. M., Golyshin, P. N. 2000. Int. J. System. Evol. Microbiol. 50: 997-1006.
Kasai, Y., Kishira, H., Syutsubo, K., and Harayama, S. 2001. Environ. Microbiol. 3: 246-255.
Kasai, Y., Kishira, H., Sasaki, T., Syutsubo, K., Watanabe, K., and Harayama, S. 2002. Environ. Microbiol. 4:141-147.
Kato et al., 1996, Appl. Microbiol. Biotechnol. 45: 363-70
Klinke, S., Q. Ren, B. Witholt, and B. Kessler. 1999. Appl. Environ. Microbiol. 65:540-548
Lai, J S., W. M. Philbrick, and H. C. Wu. 1980. J. Biol. Chem. 255:5384-5387.
Lai, J. S., and H. C. Wu. 1980. J. Bacteriology 144:451-453.
Lee et al., 1995, Appl. Microbiol. Biotechnol. 42: 901-09
Lee, S. Y. 1996. Biotechnol. Bioeng. 49: 1-14.
Lünsdorf, H., Strömpl, C., Osborn, A. M., Moore, E. R. B., Abraham, W. R. Timmis, K. N. 2001. Methods Enzymol., 336: 317-331.
Madison, L. L., and Huisman, G. W. 1999. Microbiol. Mol. Biol. Rev. 63:21-53.
Ochman H., Gerber A S, Hartl D L. 1988. Genetics. November, 120 (3):621-3.
Poirrier, Y., Ventre, G., Caldelari, D. 1999. Plant Physiology, December, Vol. 121, pp. 1359-1366.
O'Toole, R. Kolter. 1999. Molecular Microbiology. Volume 28, Issue 3, page 449-461.
Rock, C. O., Goelz, S. E., and Cronan, J. E., Jr. 1981. J. Biol. Chem. 256, 736-742.
Rock, C. O., and S. Jackowski. 1982. J. Biol. Chem. 257: 10759-10765.
Steinbüchel, A. "Polyhydroxyalkanoic acids", in: Biomaterials, D. Byrom, Ed., MacMillan Publishers, Basingstoke 1991, p. 123 ff.
Steinbuchel and Wiese. 1992. Appl. Microbiol. Biotechnol. 37: 691 97
Steinbuchel and Valentin. 1995. FEMS Microbiol. Lett. 28: 219-28).
Syutsubo, K., Kishira, H., and Harayama, S. 2001. Environ. Microbiol. 3: 371-379.
Valentin et al. 1992. Appl. Microbiol. Biotechnol, 36: 507-14.
Valentin et al. 1994. Appl. Microbiol. Biotechnol, 40: 710-16;
Valentin et al., 1996, Appl. Microbiol. Biotechnol. 46: 261-67
Wallen and Rohweder. 1974. Environ. Sci. Technol, 8: 576-79
Williams and Peoples. 1996. Chemtech 26, 38-44
Yakimov M M, Golyshin P N, Lang S, Moore E R, Abraham W R, Lunsdorf H, Timmis K N. 1998. Int. J. Syst. Bacteriol. April; 48:339-48.

The invention claimed is:

1. A genetically engineered *Pseudomonas putida* having at least one modification in at least one gene encoding a protein involved in the metabolism of polyhydroxyalkanoate(s) (PHA), wherein the protein is a thioesterase acting on (R)-3-OH-acyl-CoA as a substrate which competes with enzymes of the PHA synthesis pathway for intermediates of the PHA synthesis pathway, wherein the at least one modification causes deposition and/or overproduction of medium or long chain PHA relative to PHA production of the corresponding wildtype *Pseudomonas putida*, wherein the genetically engineered *Pseudomonas putida* further comprises a modification in the 1-acyl-sn-glycerol-3-phosphate acyltransferase gene which inactivates the gene.

2. The genetically engineered *Pseudomonas putida* of claim 1, wherein the thioesterase is acyl-CoA thioesterase tesB-like.

3. The genetically engineered *Pseudomonas putida* of claim 1, wherein the enzyme is encoded by a nucleic acid sequence comprising a nucleic acid sequence of SEQ ID NO: 4 or SEQ ID NO: 8 wherein the nucleic acid sequence is modified by the at least one modification.

4. The genetically engineered *Pseudomonas putida* of claim 1, wherein the at least one modification causes a complete or partial inactivation of the modified gene.

5. The genetically engineered *Pseudomonas putida* of claim 1, wherein the at least one modification is effected by a transposon insertion selected from the group consisting of Tn5 and Tn10 transposons.

6. The genetically engineered *Pseudomonas putida* of claim 1, wherein the at least one modification is effected by transposon mutagenesis.

7. The genetically engineered *Pseudomonas putida* of claim 1, wherein the gene is integrated into the chromosome of the *Pseudomonas putida*.

8. The genetically engineered *Pseudomonas putida* of claim 1, wherein the at least one modification is effected by Tn5 transposon insertion.

9. The genetically engineered *Pseudomonas putida* of claim 1, wherein the at least one modification is effected by a transposon Tn5 insertion in a gene downstream of the modified gene.

10. The genetically engineered *Pseudomonas putida* of claim 1, wherein the at least one modification is effected by transposon mutagenesis using a miniTn5 Km element (SEQ ID NO: 4).

11. The genetically engineered *Pseudomonas putida* of claim 1, wherein the at least one modification is effected by transposon mutagenesis using a miniTn5 Str/Sp element.

12. The genetically engineered *Pseudomonas putida* of claim 1, wherein the extracellular deposition or overproduction of polyhydroxyalkanoate(s) PHA, results in a PHA production which is at least 5 times higher than the PHA production of the corresponding wild type microorganism.

13. The genetically engineered *Pseudomonas putida* of claim 12, wherein the extracellular deposition or overproduction of a polyhydroxy alkanoate(s) PHA results in a PHA production which is at least 10 times higher than the PHA production of the corresponding wild type *Pseudomonas putida*.

14. The genetically engineered *Pseudomonas putida* of claim 12, wherein the extracellular deposition or overproduction of a polyhydroxy alkanoate(s) PHA results in a PHA production which is at least 40 times higher than the PHA production of the corresponding wild type *Pseudomonas putida*.

15. The genetically engineered *Pseudomonas putida* of claim 12, wherein the extracellular deposition or overproduction of a polyhydroxy alkanoate(s) PHA results in a PHA production which is at least 100 times higher than the PHA production of the corresponding wild type *Pseudomonas putida*.

* * * * *

UNITED STATES PATENT AND TRADEMARK OFFICE
CERTIFICATE OF CORRECTION

Page 1 of 1

PATENT NO. : 8,623,632 B2
APPLICATION NO. : 11/989909
DATED : January 7, 2014
INVENTOR(S) : Sabirova et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1043 days.

Signed and Sealed this
Ninth Day of June, 2015

Michelle K. Lee
*Director of the United States Patent and Trademark Office*